(12) United States Patent
Chanteux et al.

(10) Patent No.: US 11,578,136 B2
(45) Date of Patent: *Feb. 14, 2023

(54) COMPOSITIONS AND METHODS FOR TREATING CANCER

(71) Applicants: INNATE PHARMA, Marseilles (FR); OREGA BIOTECH, Ecully (FR)

(72) Inventors: Stéphanie Chanteux, Marseilles (FR); Nicolas Gourdin, Marseilles (FR); Carine Paturel, Marcy l'Etoile (FR); Ivan Perrot, Cassis (FR); Benjamin Rossi, Marseilles (FR)

(73) Assignees: INNATE PHARMA, Marseilles (FR); OREGA BIOTECH, Ecully (FR)

( * ) Notice: Subject to any disclaimer, the term of this patent is extended or adjusted under 35 U.S.C. 154(b) by 331 days.

This patent is subject to a terminal disclaimer.

(21) Appl. No.: 16/477,506

(22) PCT Filed: Mar. 16, 2018

(86) PCT No.: PCT/EP2018/056661
§ 371 (c)(1),
(2) Date: Jul. 11, 2019

(87) PCT Pub. No.: WO2018/167267
PCT Pub. Date: Sep. 20, 2018

(65) Prior Publication Data
US 2019/0389961 A1 Dec. 26, 2019

Related U.S. Application Data

(60) Provisional application No. 62/586,220, filed on Nov. 15, 2017, provisional application No. 62/471,994, filed on Mar. 16, 2017.

(51) Int. Cl.
| | |
|---|---|
| *C07K 16/28* | (2006.01) |
| *A61K 39/395* | (2006.01) |
| *A61K 45/06* | (2006.01) |
| *A61P 35/00* | (2006.01) |
| *G01N 33/574* | (2006.01) |

(52) U.S. Cl.
CPC ...... *C07K 16/2896* (2013.01); *A61K 39/3955* (2013.01); *A61K 45/06* (2013.01); *A61P 35/00* (2018.01); *G01N 33/57492* (2013.01); *C07K 2317/41* (2013.01); *C07K 2317/52* (2013.01); *C07K 2317/565* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 4,861,719 A | 8/1989 | Miller | |
| 5,202,238 A | 4/1993 | Fell et al. | |
| 5,204,244 A | 4/1993 | Fell et al. | |
| 5,225,539 A | 7/1993 | Winter et al. | |
| 5,229,275 A | 7/1993 | Goroff | |
| 5,278,056 A | 1/1994 | Bank et al. | |
| 5,530,101 A | 6/1996 | Queen et al. | |
| 5,565,332 A | 10/1996 | Hoogenboom | |
| 5,567,610 A | 10/1996 | Borrebaeck et al. | |
| 5,585,089 A | 12/1996 | Queen et al. | |
| 5,660,827 A | 8/1997 | Thorpe et al. | |
| 5,859,205 A | 1/1999 | Adair et al. | |
| 5,882,877 A | 3/1999 | Gregory et al. | |
| 5,994,524 A | 11/1999 | Matsushima et al. | |
| 6,013,516 A | 1/2000 | Verma et al. | |
| 6,018,032 A | 1/2000 | Koike et al. | |
| 6,127,175 A | 10/2000 | Vigne et al. | |
| 6,162,963 A | 12/2000 | Kucherlapati et al. | |
| 6,464,998 B1 | 10/2002 | Beuzard et al. | |
| 6,737,056 B1 | 5/2004 | Presta | |
| 8,865,653 B2 | 10/2014 | Zitvogel et al. | |
| 9,605,080 B2 | 3/2017 | Lonberg et al. | |
| 10,662,253 B2 | 5/2020 | Levy et al. | |
| 11,377,503 B2 | 7/2022 | Chanteux et al. | |

(Continued)

FOREIGN PATENT DOCUMENTS

| | | |
|---|---|---|
| EP | 0125023 | 11/1984 |
| EP | 0173494 A2 | 3/1986 |
| EP | 0239400 | 9/1987 |
| EP | 0519596 A1 | 12/1992 |
| EP | 0592106 A1 | 4/1994 |

(Continued)

OTHER PUBLICATIONS

Brummell et al, Biochemistry; 1993; vol. 32, pp. 1180-1187.*
Kobayashi et al. Protein Engineering; 1999; vol. 12, pp. 879-844.*
Brorson et al. J. Immunol; 1999; vol. 163, pp. 6694-6701.*
Coleman Research in Immunol; 1994; vol. 145; pp. 33-36.*
Rudikoff, et al. (Proc. Natl. Acad. Sci. USA, 79(6):1979-1983, 1982).*

(Continued)

*Primary Examiner* — Bridget E Bunner
*Assistant Examiner* — Fozia M Hamud
(74) *Attorney, Agent, or Firm* — Knobbe, Martens, Olson & Bear, LLP

(57) ABSTRACT

The present invention relates to antigen-binding compounds that inhibit the enzymatic activity of soluble human CD39. The invention also relates to cells producing such compounds; methods of making such compounds, and antibodies, fragments, variants, and derivatives thereof; pharmaceutical compositions comprising the same; methods of using the compounds to diagnose, treat or prevent diseases, e.g., cancer.

12 Claims, 12 Drawing Sheets
Specification includes a Sequence Listing.

(56) References Cited

U.S. PATENT DOCUMENTS

| | | | |
|---|---|---|---|
| 2005/0037382 A1 | 2/2005 | Robson et al. | |
| 2005/0158280 A1 | 7/2005 | Robson et al. | |
| 2006/0002932 A1 | 1/2006 | Vieweg | |
| 2006/0246006 A1 | 11/2006 | Johnson et al. | |
| 2009/0068202 A1 | 3/2009 | Chen et al. | |
| 2010/0303828 A1 | 12/2010 | Levy et al. | |
| 2013/0034559 A1 | 2/2013 | Queva et al. | |
| 2013/0156790 A1* | 6/2013 | Zitvogel ................. | A61N 5/10 435/6.12 |
| 2013/0273062 A1 | 10/2013 | Bensussan et al. | |
| 2016/0137747 A1 | 5/2016 | Levy et al. | |
| 2019/0062448 A1 | 2/2019 | Soros et al. | |
| 2019/0153113 A1 | 5/2019 | Bastid et al. | |
| 2019/0218304 A1 | 7/2019 | Chanteux et al. | |
| 2019/0218308 A1 | 7/2019 | Chanteux et al. | |
| 2020/0024357 A1 | 1/2020 | Chanteux et al. | |
| 2021/0032367 A1 | 2/2021 | Levy et al. | |
| 2021/0261686 A1 | 8/2021 | Bensussan et al. | |

FOREIGN PATENT DOCUMENTS

| | | |
|---|---|---|
| WO | WO 1987/002671 | 5/1987 |
| WO | WO 1987/005330 | 9/1987 |
| WO | WO 1991/009967 | 7/1991 |
| WO | WO 1994/019478 | 9/1994 |
| WO | WO 1995/014785 | 6/1995 |
| WO | WO 1996/002576 | 2/1996 |
| WO | WO 1996/022378 | 7/1996 |
| WO | WO 1997/010354 | 3/1997 |
| WO | WO 1998/045322 | 10/1998 |
| WO | WO 1999/058572 | 11/1999 |
| WO | WO 2003/052121 | 6/2003 |
| WO | WO 2003/101485 | 12/2003 |
| WO | WO 2006/111986 | 10/2006 |
| WO | WO 2006/121168 | 11/2006 |
| WO | WO 2007/005874 | 1/2007 |
| WO | WO 2009/014708 | 1/2009 |
| WO | WO 2009/095478 | 8/2009 |
| WO | WO 2009/101611 | 8/2009 |
| WO | WO 2009/114335 | 9/2009 |
| WO | WO 2010/077634 | 7/2010 |
| WO | WO 2011/066389 | 6/2011 |
| WO | WO 2011/066501 | 6/2011 |
| WO | WO 2012/065950 | 5/2012 |
| WO | WO 2012/085132 | 6/2012 |
| WO | WO 2012/087746 | 6/2012 |
| WO | WO 2012/145493 | 10/2012 |
| WO | WO 2012/168199 | 12/2012 |
| WO | WO 2013/019906 | 2/2013 |
| WO | WO 2015/049447 | 4/2015 |
| WO | WO 2015/085847 | 6/2015 |
| WO | WO 2015/164573 | 10/2015 |
| WO | WO 2016/055609 | 4/2016 |
| WO | WO 2016/073845 | 5/2016 |
| WO | WO 2016/075099 | 5/2016 |
| WO | WO 2016/081748 | 5/2016 |
| WO | WO 2016/131950 | 8/2016 |
| WO | WO 2017/064043 | 4/2017 |
| WO | WO 2017/089334 | 6/2017 |
| WO | WO 2017/098421 | 6/2017 |
| WO | WO 2017/100670 | 6/2017 |
| WO | WO 2017/120508 | 7/2017 |
| WO | WO 2017/153952 | 9/2017 |
| WO | WO 2017/157948 | 9/2017 |
| WO | WO 2018/094148 | 5/2018 |
| WO | WO 2018/167267 | 9/2018 |
| WO | WO 2018/237157 | 12/2018 |
| WO | WO 2019/027935 | 2/2019 |

OTHER PUBLICATIONS

Casset et al; Biochemical and Biophysical Research Communications, 2003; 307:198-205.*

Abe et al., "Increased_Foxp3+ CD4+ Regulatory T Cells with Intact Suppressive Activity but Altered Cellular Localization in Murine Lupus", Am. J. Path. (2008) 173(6): 1682-1692.
Allard et al., "The ectonucleotidases CD39 and CD73: novel checkpoint inhibitor targets", Immunol Rev. (Mar. 2017): 276(1):121-144.
Altschul et al., "Basic Local Alignment Search Tool", J Mol Biol. (1990) 215: 403-410.
Altschul et al., "Gapped BLAST and PSI-BLAST: a new generation of protein database search programs", Nucl Acids Res. (1997) 25(17): 3389-3402.
AMERSHAM Biosciences, "Antibody Purification—Handbook", Publication No. 18-1037-46, Edition AC, (2002) 112 pages.
Bastid et al., "ENTPD1/CD39 is a promising therapeutic target in oncology", Oncogene (2013) 32(14):1743-1751 [publ online Jul. 2, 2012].
Baudino et al., "Crucial role of aspartic acid at Position 265 in the CH2 Domain for Murnie IgG2a and IgG2b Fc-associated Effector Functions", J Immunol. (2008) 181: 6664-6669.
Beavis et al., "CD73: a potent suppressor of antitumor immune responses", Trends in Immunol. (2012) 33(5): 231-237.
Benussan et al., "Detection of membrane-bound HLA-G translated products with a specific monoclonal antibody", PNAS U.S.A., 1995, 92: 10292-10296.
Bluestone et al., "Natural versus adaptive regulatory T cells", Nat Rev Immunol. (2003) 3(3):253-257.
Bonnefoy et al., "CD39: A complementary target to immune checkpoints to counteract tumor-mediated immosuppression", Oncoimmunology. (2015) 4(5):e1003015.
Borsellino et al., "Expression of ectonucleotidase CD39 by Foxp3+ Treg cells: hydrolysis of extracellular ATP and immune suppression", (Aug. 2007) 110(4): 1225-1232.
Brady et al., "New Cosmid Vectors Developed for Eukaryotic DNA Cloning", Gene (1984) 27(2):223-232.
Bruhns, "Properties of mouse and human IgG receptors and their contribution to disease models," Blood, Jun. 2012, 119(24):5640-5649.
Buffon et al., "NTPDase and 5' ecto-nucleotidase expression profiles and the pattern of extracellular ATP metabolism in the Walker 256 tumor", Biochim Biophys Acta. (2007) 1770(8):1259-1265.
Burgers et al., "The challenges of HIV vaccine development", Best Pract Res Clin OBst Gyn. (2005) 19(2): 277-291.
Cabrera et al., "An Immunomodulatory Role for CD4+CD25+ Regulatory T Lymphocytes in Hepatitis C Virus Infection", Hepatol. (2004) 40(5): 1062-1071.
Caron et al., "Engineered humanized dimeric forms of IgG are more effective antibodies", J Exp Med. (1992) 176(4):1191-1195.
Carrillo et al., "The Multiple Sequence Alignment Problem in Biology", SIAM J Appl Math. (1988) 48(5): 1073-1082.
Carter et al., "Humanization of an anti-p185HER2 antibody for human cancer therapy", PNAS U.S.A. (1992) 89: 4285-4289.
Chardés et al., "Efficient amplification and direct sequencing of mouse variable regions from any immunoglobulin gene family", FEBS Lett. (1999) 452(3):386-394.
Chiappelli et al., "Neuroendocrine immunity in patients with Alzheimer's disease: toward translational epigenetics", Bioinformation (2007) vol. 2: 1-4.
Chothia et al., "Canonical Structures for the Hypervariable Regions of Immunoglobulins", J Mol Biol. (1987) 196: 901-917.
Clackson et al., "A Hot Spot of Binding Energy in a Hormone-Receptor Interface", Science (1995) 267: 383-386.
Clayton et al., "Cancer Exosomes Express CD39 and CD73, which suppress T Cells through Adenosine Production", J Immunol. (Jul. 2011) 187(2):676-683.
Cole et al., "The EBV-Hybridoma Technique and its Application in Human Lung Cancer" in *Monoclonal Antibodies and Cancer Therapy* Reisfeld et al. [Eds.] (1985) pp. 77-96.
Coligan et al. [Eds.], "Current Protocols in Immunology", John Wiley & Sons, Inc. (1991); TOC.
Connolly et al., "Female Mice Chimeric for Expression of the Simian Virus 40 Tag under Control of the *MISIIR* Promoter Develop Epithelial Ovarian Cancer", Cancer Res. (2003) 64(6):1389-1397.

(56) References Cited

OTHER PUBLICATIONS

Cote et al., "Generation of human monoclonal antibodies reactive with cellular antigens", Proc Natl Acad Sci USA (1983) 80:2026-2030.
Damle et al., "B-cell chronic lymphocytic leukemia cells express a surface membrane phenotype of activated, antigen-experienced B lymphocytes", Blood (2002) 99(11): 4087-4093.
Deaglio et al., "Adenosine generation catalyzed by CD39 and CD73 expressed on regulatory T cells mediates immune suppression", J Exp Med., (2007) 204(6):1257-1265.
Devereux et al., "A comprehensive set of sequence analysis programs for the VAX", Nucl Acid Res. (1984) 12(1): 387-395.
Downard K.M., "Contributions of mass spectrometry to structural immunology", J Mass Spectrom. (2000) 35: 493-503.
Dwyer et al., "CD39 and control of cellular immune responses", Purinergic Signal. (2007) 3(1-2):171-180.
Dwyer et al., "Expression of CD39 by Human Peripheral Blood CD$+CD25+ T Cells Denotes a Regulatory Memory Phenotype", Am J Transplantation (2010) 10: 2410-2420.
Dzhandzhugazyan et al., "Ecto-ATP diphosphohydrolase/CD39 is overexpressed in differentiated human melanomas", FEBS Lett. (1998) 430:227-230.
Edge et al., "Deglycosylation of glycoproteins by trifluoromethanesulfonic acid", Anal Biochem. (1981) 118(1):131-137.
Ehring H., "Hydrogen Exchange/Electrospray Ionization Mass Spectrometry Studies of Structural Features of Proteins and Protein/Protein Interactions", Analyt Biochem. (1999) 267: 251-259.
Engen et al., "Metrohm 792 Basic IC", Anal Chem. (2001) 73: 256A-265A.
Erdmann et al., "Activation of Th1 and Tc1 cell adenosine A2A receptors directly inhibits IL-2 secretion in vitro and IL-2-driven expansion in vivo", Blood (Jun. 2005) 105(12): 4707-4714.
European Journal of Immunology, Instructions to Authors, 2010, in 6 pages.
Fägerstam et al., "Detection of Antigen-Antibody Interactions by Surface Plasmon Resonance", J Mol Recogn. (1990) 3(5/6): 208-214.
Fredholm et al., "Adenosine, an endogenous distress signal, modulates tissue damage and repair", Cell Death Differ. (2007) 14(7):1315-1323.
Fujarewicz et al., "A multi-gene approach to differentiate papillary thyroid carcinoma from benign lesions: gene selection using support vector machines with bootstrapping," Endocr Relat Cancer. (2007) 14(3):809-826.
Gavilondo et al., "Antibody Engineering at the Millennium", BioTechniques (Jul. 2000) 29:128-145.
Gazzano-Santoro et al., "A non-radioactive complement-dependent cytotoxicity array for anti-CD20 monoclonal antibody", J Immunol Methods (1997) 202(2):163-171.
GENBANK Accession No. P49961; "Ectonucleoside triphosphate diphosphohydrolase 1 . . . ", Created: Oct. 1, 1996; 7 pages.
GENBANK Accession No. NP_001237; "Ectonucleoside triphosphate diphosphohydrolase 2 Isofpr, 2 [*Homo sapiens*]", Created: Jul. 2008; 3 pages.
GENBANK Accession No. NP_001238; "Ectonucleoside triphosphate diphosphohydrolase 2 Isoform 1 [*Homo sapiens*]", Created: Dec. 2015; 3 pages.
GENBANK Accession No. NP_001239.2; "Ectonucleoside triphosphate diphosphohydrolase 2 Isoform 1 [*Homo sapiens*]", Created: May 2014; 3 pages.
GENBANK Accession No. NP_001240.1; "Ectonucleoside triphosphate diphosphohydrolase 5 Isoform 1 Precursor [*Homo sapiens*]", Created: Jan. 2009; 3 pages.
GENBANK Accession No. U64863.1; "Human hPD-1 (hPD-1) mRNA, complete cds", Created: Oct. 12, 2005; 3 pages.
GENBANK Accession No. NP_002517; "Human CD73 preprotein (monomer)", Created: May 1, 2019; 4 pages.

Gerber et al., "Pharmacology and Pharmacodynamics of Bevacizumab as Monotherapy or in combination with Cytotoxic Therapy in Preclinical Studies", Cancer Res. 2005; 65(3):671-680.
Gillies et al., "A tissue-specific transcription enhancer element is located in the major intron of a rearranged immunoglobulin heavy chain gene", Cell (1983) 33(3):717-728.
Goding J.W., "Monoclonal Antibodies: Principles and Practice", 2nd Edition, Academic Press/Harcourt Brace Javanovich, Publishers (1986); Chapter 3, 47 pages.
Goede et al., "Induction of Inflammatory Angiogenesis by Monocyte Chemoattractant Protein-1", Int. J. Canc.(1999) 82: 765-770.
Gouttefangeas et al., "The CD29 molecule defines distinct cytotoxic subsets within alloactivated human CD8-positive cells", Eur J Immunol. 1992, 22:2681-2685.
Gouttefangeas et al., "Biochemical analysis and epitope mapping of mAb defining CD39"; in Schlossman, et al. [Eds.] *Leucocyte Typing V.* Oxford University Press, New York, 1995; pp. 383-385.
Green et al., "Antigen-specific human monoclonal antibodies from mice engineered with human Ig heavy and light chain YACs", Nature Genet. (1994) 7: 13-21.
Gribskov et al. [Eds.], "Sequence Analysis Primer", M Stockton Press (1991); TOC.
Griffin et al. [Eds.], "Computer Analysis of Sequence Data—Part I" in *Methods in Molecular Biology* Humana Press (1994); TOC.
Gu et al., "Human CD39hi regulatory T cells present stronger stability and function under inflammatory conditions", Cell Mol Immunol. (2017) 14: 521-528; publ. online Jul. 4, 2016.
Harlow et al. [Eds.] "Antibodies—A Laboratory Manual", Cold Spring Harbor Laboratory (1988); TOC.
Häusler et al., "CD39 is expressed by human ovarian carcinoma cell lines and inhibits immunological tumour defence", Presentation at the University Women's Hospital Würzburg, Germany; Obstetrics Gynaecology (2008) 68—PO—DOI: 10.1055/s-0028-1089305; Original in German; English Translations in 4 pages.
Häusler et al., "CD39 wird in vivo und in vitro von Ovarialkarzinomzellen experimiert und inhibiert die lytische Aktivität von NK Zellen", Geburtshilfe Frauenheilkd. (2009), 69—P106; DOI: 10.1055/s-0029-1225180; Abstract in 1 page.
Häusler et al., "Ovarian carcinoma cells suppress anti-tumoral immune responses by extracellular generation of adenosine via CD39 and CD73", Geburshilfe Frauenheilkd. (2009) 69—A042; DOI: 10.1055/s-0029-1238961; Original in German (Two Engl. Translations) in 5 pages.
Häusler et al., "Ectonucleotidases CD39 and CD73 on OvCA cells are potent adenosine-generating enzymes responsible for adenosine receptor 2A-dependent suppression of T cell function and NK cell cytotoxicity", Cancer Immunol Immunother. (2011) 60(10):1405-1418.
Hayes et al., "CD39 is a promising therapeutic antibody target for the treatment of soft tissue sarcoma", Am J Transl Res. (2015) 7(6): 1181-1188.
Hisaeda, H. "Regulatory T-cells in Infection Immunity" Experimental Med. (2007) 25(18): 2862-2867.
Hoskin et al., "Inhibition of T cell and natural killer cell function by adenosine and its contribution to immune evasion by tumor cells (Review)", Inter'l J Oncol. (2008) 32: 527-535.
Hou TJ., "Comparison of Multiple Comparison Methods for Identifying Differential Gene Expression in Simulated and Real Papillary Thyroid Cancer Microarray Data", Thesis, presented to the Faculty of the University of Texas School of Public Health (Aug. 2009) in 88 pages.
Huang et al., "NMR Identification of Epitopes of Lyme Disease Antigen OspA to Monoclonal Antibodies", J Mol Biol. (1998) 281(1): 61-67.
Jakobovits et al., "Germ-line transmission and expression of a human-derived yeast artificial chromosome", Nature (1993) 362: 255-258.
Jie et al., "Intratumoral regulatory T cells upregulate immunosuppressive molecules in head and neck cancer patients", (Oct. 2013) 1-7.
Jin et al., "CD73 on Tumor Cells Impairs Antitumor T-Cell Responses: A Novel Mechanism of Tumor-Induced Immune Suppression", Cancer Res. (2010) 70(6):2245-2255 and Addendum.

(56) References Cited

OTHER PUBLICATIONS

Jones et al., "Replacing the complementarity-determining regions in a human antibody with those from a mouse", Nature (1986) 321: 522-525.
Kabat et al., "Sequences of Proteins of Immunological Interest", 5th Ed. U.S. Department of Health and Human Services (NIH Publication No. 91-3242) (1991); TOC.
Kiselar et al., "Direct Identification of Protein Epitopes by Mass Spectrometry without immobilization of Antibody and Isolation of Antibody—Peptide Complexes", Anal Chem. (1999) 71(9): 1792-1801.
Kishore et al., "Expression of NTPDase1 and NTPDase2 in murine kidney: relevance to regulation of P2 receptor signaling", Am J Physiol Renal Physiol. (2005) 288(5):F1032-F1043.
Klimka et al., "Human anti-CD30 recombinant antibodies by guided phage antibody selection using cell panning", British J Cancer. (2000) 83(2): 252-260.
Knapp et al., "Crystal structure of the human ecto-5'-nucleotidase (CD73): insights into the regulation of purinergic signaling". Structure (2012) 20(12): 2161-2173.
Köhler et al., "Continuous cultures of fused cells secreting antibody of predefined specificity", Nature (1975) 256(5517):495-497.
Kondo et al., "Expression of CD73 and its ecto-5'-nucleotidase activity are elevated in papillary thyroid carcinomas", Histopathology (2006) 48(5):612-614.
Kröger et al., "Epitope-mapping of transglutaminase with parallel label-free optical detection", Biosens Bioelectr. (2002) 17: 937-944.
Künzli et a., "Upregulation of CD39/NTPDases and P2 receptors in human pancreatic disease", Am J Physiol Gastrointest Liver Physiol. (2007) 292(1):G223-230.
Kuwana et al., "Expression of Chimeric Receptor composed of Immunoglobulin-derived V regions and T-cell receptor-derived C regions", Biochem Biophys Res Commun. (1987) 149(3):960-968.
Leipert et al., "Investigation of the Molecular Recognition of Amino Acids by Cyclopeptides with Reflectometric Interference Spectroscopy", Angew Chem Int Ed. (1998) 37(23): 3308-3311.
Lesk A. [Ed], "Computational Molecular Biology—Sources and Methods for Sequence Analysis", Oxford University Press (1988); TOC.
Liyanage et al., "Prevalence of Regulatory T Cells is Increased in Periperal Blood and Tumor Microenvironment of Patients with Pancreas or Breast Adenocarcinoma", J Immunol. (2002) 169(5): 2756-2761.
Lonberg et al., "Antigen-specific human antibodies from mice comprising four distinct genetic modifications", Nature. (1994) 368: 856-859.
Maliszewski et al. "The CD39 lymphoid cell activation antigen—Molecular Cloning and Structural Characterization", J Immunol. (1994) 153(8):3574-3583.
Mandapathil et al., "Increased Ectonucleotidase Expression and Activity in Regulatory T Cells of patients with head and neck cancer", Clin Cancer Res. (2009) 15(20):6348-6357.
Mandapathil et al., "Targeting human inducible regulatory T cells (Tr1) in patients with cancer: blocking of adenosine-prostaglandin E2 cooperation", Expert Opin Biol Ther. (2011) 11(9):1203-1214.
Mariuzza et al., "The Structural Basis of Antigen-Antibody Recognition", Ann Rev Biophys Biophys Chem. (1987) 16:139-159.
Marshak-Rothstein et al., "Hybridoma proteins expressing the predominant idiotype of the antiazophenylarsonate response of A/J mice", PNAS (1980) 77(2): 1120-1124.
Mason et al., "Transcription cell type specificity is conferred by an immunoglobulin VH gene promoter that includes a functional consensus sequence", Cell (1985) 41(2):479-487.
Mazzanti et al., "Liver angiogenesis as a risk factor for hepatocellular carcinoma development in hepatitis C virus cirrhotic patients", World J. Gastroenterol. (2007) 13(37):5009-5014.
McCafferty et al., "Phage antibodies: filamentous phage displaying antibody variable domains", Nature. (1990) 348: 552-554.

Meyer et al., "Saturation Transfer Difference NMR Spectroscopy for Identifying Ligand Epitopes and Binding Specificities", E. Schering Res Found Workshop 44; in *Leucocyte Trafficking*; Springer Verlag (2004) pp. 149-167.
Meyer et al., "Expression of CD39 and CD73 as means of evading anti-tumor immune responses in lung cancer", J Immunol. (Apr. 2010) 184:100.7 (Abstract).
Michaud et al., "Autophagy-dependent anticancer immune responses induced by chemotherapeutic agents in mice", Science (2011) 334(6062):1573-1577.
Miyaji et al., "Expression of human beta-interferon in Namalwa KJM-1 which was adapted to serum-free medium", Cytotech. (1990) 3(2):133-140.
Mizukami et al., "Binding region for human immunodeficiency virus (HIV) and epitopes for HIV-blocking monoclonal antibodies of the CD4 molecule defined by site-directed mutagenesis", Proc Natl Acad Sci. USA (1988) 85:9273-9277.
Mizukami et al., "A new SV40-based vector developed for cDNA expression in animal cells", J Biochem (Tokyo) (1987) 101(5):1307-1310.
Möller et al., "Monitoring the expression of purinoceptors and nucleotide-metabolizing ecto-enzymes with antibodies directed against proteins in native conformation", Purinergic Signalling, 3(4):359-366 (2007).
Mor et al., "Identification of Aldolase as a Target Antigen in Alzheimer's Disease", J Immunol. (2005) 175: 3439-3445.
Morrison et al., "Chimeric human antibody molecules: Mouse antigen-binding domains with human constant region domains", Proc Natl Acad Sci USA (1984) 81:6851-6855.
Müller R., "Determination of Affinity and Specificity of Anti-Hapten Antibodies by Competitive Radioimmunoassay", Meth Enzymol. (1983) 92: 589-601.
Munkonda et al., "Characterization of a monoclonal antibody as the first specific inhibitor of human NTP diphosphohydrolase-3—Partial characterization of the inhibitory epitope and potential applications", FEBS J. (2009) 276: 479-496.
Neuberger et al., "Recombinant antibodies possessing novel effector functions", Nature (1984) 312:604-608.
Nice et al., "Mapping of the antibody- and receptor-binding domains of granulocyte colony-stimulating factor using an optical biosensor", J Chromatogr. (1993) 646: 159-168.
Nikolova et al., "CD39/Adenosine Pathway is involved in AIDS Progression", Plos Pathog. (2011) 7(7): e1002110; 14 pages.
O'Hare K. et al., "Transformation of mouse fibroblasts to methotrexate resistance by a recombinant plasmid expressing a prokaryotic dihydrofolate reductase", Proc Natl Acad Sci. USA (1981) 78(3):1527-1531.
Ohta et al., "A2A adenosine receptor protects tumors from antitumor T cells", PNAS U S A. (2006) 103(35):13132-13137.
Padlan, E.A., "A Possible Procedure for Reducing the Immunogenicity of Antibody Variable Domains while Preserving their Ligand-binding Properties", Mol Immunol (1991) 28(4/5):489-498.
Perrot et al., "Abstract 2718: Preclinical development of humanized CD39 and CD73 (IPH53) blocking antibodies targeting the ATP/adenosine immune checkpoint pathway for cancer immunotherapy", AACR Annual Meeting 2018, (Jul. 2018); DOI: 10.1158/1538-7445. AM2018-2718 in 2 pages.
Perry et al., "Increased CD39 expression on CD4+ T lymphocytes has clinical and prognostic significance in chronic lymphocytic leukemia", Ann Hematol. (2012) 91: 1271-1279.
Plückthun et al., "Mono- and Bivalent Antibody Fragments Produced in *Escherichia coli*: Engineering, Folding and Antigen Binding", Immunol Rev. (1992) 130: 151-188.
PNAS U.S.A., Information for Authors, Jan. 2013 in 5 pages.
Presta et al., "Antibody engineering", Curr Opin Struct Biol. (1992) 2: 593-596.
Presta et al., "Humanization of an Antibody Directed Against IgE", J Immunol. (1993) 151(5): 2623-2632.
Pulte et al., "CD39 activity correlates with stage and inhibits platelet reactivity in chronic lymphocytic leukemia", J Transl Med. (2007) 4:5-23.

(56) References Cited

OTHER PUBLICATIONS

Rawstron et al., "Chronic Lymphocytic Leukaemia (CLL) and CLL-Type Monoclonal B-Cell Lymphocytosis (MBL) Show Differential Expression of Molecules Involved in Lymphoid Tissue Homing", Cytometry B Clin Cytom. (2010) 78B(Suppl 1):S42-S46.
Remington J.R. *The Science and Practice of Pharmacy*, The Philadelphia College of Pharmacy and Science; 19th Edition (1995), TOC.
Riechmann et al., "Reshaping human antibodies for therapy", Nature (1988) 332:323-327.
Robson et al., "The E-NTPDase family of ectonucleotidases: Structure function relationships and pathophysiological significance", Purinergic Signal. (2006) 2(2):409-430.
Roguska et al., "Humanization of Murine Monoclonal Antibodies through Variable Domain Resurfacing", Proc Natl Acad Sci USA (1994) 91:969-973.
Ryan et al., "Preclinical Safety Evaluation of rhuMAbVEGF, an Antiangiogenic Humanized Monoclonal Antibody", Toxicol Pathol. (1999) 27(1): 78-86.
Saito et al., "Nuclear Magnetic Resonance Spectroscopy for the Study of B-Cell Epitopes", Methods. (1996) 9(3): 516-524.
Saunal et al., "Mapping of viral conformational epitopes using biosensor measurements" J Immunol Meth. (1995) 183: 33-41.
Schenk et al., "Monoclonal antibodies to rat Na+, K+-ATPase block enzymatic activity", Proc Natl Acad Sci. USA (1983) 80: 5281-5285.
Schetinger et al., "NTPDase and 5'-nucleotidase activities in physiological and disease conditions: new perspectives for human health", Biofactors. (2007) 31(2):77-98.
Schuetz et al., "Molecular Classification of Renal Tumors by Gene Expression Profiling", J Mol Diagnost. (2005) 7(2):206-218.
Shevach et al., "The lifestyle of naturally occurring CD4+ CD25+ Foxp3+ regulatory T cells", Immunol Rev. (2006) 212:60-73.
Shi et al., "Prevalence of the Mercurial-Sensitive ExtoATPase in Human Small Cell Lung Carcinoma: characterization and partial purification", Arch Biochem Biophys. (1994) 315(1):177-184.
Shitara et al., A new vector for the high level expression of chimeric antibodies in myeloma cells J Immunol Meth. (1994) 167(1-2):271-278.
Shopes B., A genetically engineered human IgG mutant with enhanced cytoloytic activity, J Immunol. (1992) 148(9):2918-2922.
Sims et al., "A Humanized CD18 Antibody Can Block Function without Cell Destruction", J Imunol. (1993) 151(4): 2296-2308.
Sitkovsky et al., "Adenosine A2A receptor antagonists: blockade of adenosinergic effects and T regulatory cells", Br J Pharmacol. (2008) 153(Suppl 1):S457-S464.
Skerra A. "Bacterial expression of immunoglobulin fragments", Curr Opin Immunol. (1993) 5: 256-262.
Smith D.W. [Ed.], "Biocomputing—Informatics and Genome Projects", Academic Press, Inc. (1994); TOC.
Sojar et al., "A chemical method for the deglycosylation of proteins", Arch Biochem Biophys. (1987) 259(1):52-57.
Stagg et al., "Extracellular adenosine triphosphate and adenosine in cancer", Ongogene (2010) 29:5346-5358.
Strohl et al., "Complete variable region sequence of a nonfunctionally rearranged kappa light chain transcribed in the nonsector P3-X63-Ag8.653 myeloma cell line", Nucl Acids Res. (1987) 15(6):2771.
Strohl W.R., "Optimization of Fc-medicated effector functions of monoclonal antibodies", Curr Opin Biotechnol. (2009) 20(6): 685-691.
Studnicka et al., "Human-engineered monoclonal antibodies retain full specific binding activity by preserving non-CDR complementarity-modulating residues", Prot Engin. (1994) 7(6):805-814.
Sun et al., "CD39/ENTPD1 Expression by CD4+Foxp3+ Regulatory T Cells Promotes Hepatic Metastatic Tumor Growth in Mice", Gastroenterology (2010) 139(3):1030-1040.
Syed et al., "Ectonucleotidase NTPDase3 is abundant in pancreatic beta-cells and regulates glucose-induced insulin secretion", Endocrin. Metabol. (2013) 305(10): E1319-1326.
Taylor et al., "Human immunoglobulin transgenes undergo rearrangement, somatic mutation and class switching in mice that lack endogenous IgM". Int Immunol. (1994) 6(4):579-591.
Thotakura et al., "Enzymatic Deglycosylation of glycoproteins", Meth Enzymol. (1987) 138:350-359.
Traverso et al., "Analysis of Regulatory T Cells in Patients Affected by Renal Cell Carcinoma", The Journal of Urology (2010) 183(4): Suppl. Abstract 365 in 2 pages.
Van Amelsfort et al., "CD4+CD25+ Regulatory T Cells in Rheumatoid Arthritis", Arth Rheum. (2004) 50(9): 2775-2785.
Verhoeyen et al., "Reshaping Human Antibodies: Grafting an Antilysozyme Activity", Science (1988) 239: 1534-1536.
Von Heijne G., "Sequence Analysis in Molecular Biology—Treasure Trove or Trivial Pursuit", Academic Press, Inc. (1987) TOC.
Urlaub et al., Isolation of Chinese hamster cell mutants deficient in dihydrofolate reductase activity, Proc Natl Acad Sci. USA (1980) 77(7):4216-4220.
Wang et al., "Identification of a Fab interaction footprint site on an icosahedral virus by cryoelectron microscopy and X-ray crystallography", Nature (1992) 355: 275-278.
Wang et al., "CD39 is an Exto-(Ca2+,Mg2+)-apyrase", J Biol Chem. (1996) 271(17):9898-9901.
Ward et al., "Binding activities of a repertoire of single immunoglobulin variable domains secreted from *Escherichia coli*", Nature (1989) 341: 544-546.
Wells J.A., "Binding in the growth hormone receptor complex", PNAS USA (1996) 93: 1-6.
Whiteside et al., "The role of the adenosinergic pathway in immunosuppression mediated by human regulatory T cells (Treg)", Curr Med Chem. (2011) 18(34):5217-5223.
Whiteside et al., "Disarming suppressor cells to improve immunotherapy", Cancer Immunol Immunother. (2012) 61(2):283-288.
Wu et al., "Multimerization of a chimeric anti-CD20 single-chain Fv-Fc fusion protein is mediated through variable domain exchange", Prot Engin. (2001) 14(12):1015-1033.
Wu, "RanBPM associates with CD39 and modulates ecto-nucleotidase activity," Biochem. J. (2006) 396(1): 23-30.
Yamaguchi et al., "Manipulation of Tumour Immunity Targeting CD25+ CD4+ regulatory T-cells", Experimental Med. (2007) 25(18): 2868-2874.
Young et al., "Co-inhibition of CD73 and A2AR Adenosine Signaling Improves Anti-tumor Immune Responses", Cancer Cell (Sep. 2016) 30(3):391-403.
Yeung et al., "*CD39L2*, A Gene encoding a human nucleoside diphosphatase, predominantly expressed in the heart", Biochem. (2000) 39: 12916-12923.
Zhang et al., "CD73: Anovel Target for Cancer Immunotherapy", Cancer Res. (2010), 70(16):6407-6411.
International Search Report and Written Opinion dated Jun. 4, 2009 in PCT/EP2009/051078.
International Search Report and Written Opinion dated Feb. 24, 2012 in PCT/EP2011/073659.
International Search Report and Written Opinion dated Apr. 3, 2017 in PCT/EP2016/078395.
International Search Report and Written Opinion dated Dec. 17, 2018 in corresponding PCT/EP2018/077217 (16 pages).
International Search Report and Written Opinion dated Feb. 4, 2019 for corresponding PCT/EP2018/081364 (18 pages).
U.S. Office Action dated Jul. 20, 2012 in U.S. Appl. No. 12/863,461, filed Jul. 19, 2010.
U.S. Response dated Aug. 14, 2012 in U.S. Appl. No. 12/863,461, filed Jul. 19, 2010.
U.S. Office Action dated Oct. 1, 2012 in U.S. Appl. No. 12/863,461, filed Jul. 19, 2010.
U.S. Response dated Jan. 31, 2013 in U.S. Appl. No. 12/863,461, filed Jul. 19, 2010.
U.S. Office Action dated Mar. 6, 2013 in U.S. Appl. No. 12/863,461, filed Jul. 19, 2010.
U.S. Response dated Jun. 19, 2013 in U.S. Appl. No. 12/863,461, filed Jul. 19, 2010.

(56) References Cited

OTHER PUBLICATIONS

U.S. Notice of Allowance dated Aug. 19, 2013 in U.S. Appl. No. 12/863,461, filed Jul. 19, 2010.
U.S. Response dated Nov. 14, 2013 in U.S. Appl. No. 12/863,461, filed Jul. 19, 2010.
U.S. Office Action dated Nov. 21, 2013 in U.S. Appl. No. 12/863,461, filed Jul. 19, 2010.
U.S. Response dated Feb. 19, 2014 in U.S. Appl. No. 12/863,461, filed Jul. 19, 2010.
U.S. Office Action dated Mar. 18, 2014 in U.S. Appl. No. 12/863,461, filed Jul. 19, 2010.
U.S. Response dated Jun. 18, 2014 in U.S. Appl. No. 12/863,461, filed Jul. 19, 2010.
U.S. Office Action dated Jul. 10, 2014 in U.S. Appl. No. 12/863,461, filed Jul. 19, 2010.
U.S. Response dated Sep. 18, 2014 in U.S. Appl. No. 12/863,461, filed Jul. 19, 2010.
U.S. Office Action dated Oct. 2, 2014 in U.S. Appl. No. 12/863,461, filed Jul. 19, 2010.
U.S. Response dated Feb. 20, 2015 in U.S. Appl. No. 12/863,461, filed Jul. 19, 2010.
U.S. Office Action dated Mar. 18, 2015 in U.S. Appl. No. 12/863,461, filed Jul. 19, 2010.
U.S. Response dated Aug. 18, 2015 in U.S. Appl. No. 12/863,461, filed Jul. 19, 2010.
U.S. Office Action dated Oct. 5, 2015 in U.S. Appl. No. 12/863,461, filed Jul. 19, 2010.
U.S. Response dated Jan. 21, 2016 in U.S. Appl. No. 12/863,461, filed Jul. 19, 2010.
U.S. Office Action dated Mar. 22, 2016 in U.S. Appl. No. 12/863,461, filed Jul. 19, 2010.
U.S. Response dated Jul. 21, 2016 in U.S. Appl. No. 12/863,461, filed Jul. 19, 2010.
U.S. Office Action dated Oct. 26, 2016 in U.S. Appl. No. 12/863,461, filed Jul. 19, 2010.
U.S. Response/AFCP dated Nov. 30, 2016 in U.S. Appl. No. 12/863,461, filed Jul. 19, 2010.
U.S. Advisory Action dated Dec. 27, 2016 in U.S. Appl. No. 12/863,461, filed Jul. 19, 2010.
U.S. Final Response/RCE dated Jan. 26, 2017 in U.S. Appl. No. 12/863,461, filed Jul. 19, 2010.
U.S. Office Action dated May 4, 2017 in U.S. Appl. No. 12/863,461, filed Jul. 19, 2010.
U.S. Response dated Oct. 3, 2017 in U.S. Appl. No. 12/863,461, filed Jul. 19, 2010.
U.S. Office Action dated Dec. 1, 2017 in U.S. Appl. No. 12/863,461, filed Jul. 19, 2010.
U.S. Response dated May 31, 2018 in U.S. Appl. No. 12/863,461, filed Jul. 19, 2010.
U.S. Office Action dated Jul. 30, 2018 in U.S. Appl. No. 12/863,461, filed Jul. 19, 2010.
U.S. Preliminary Amendment dated Jun. 20, 2013 in U.S. Appl. No. 13/996,097, filed Jun. 20, 2013.
U.S. Restriction Requirement dated May 8, 2014 in U.S. Appl. No. 13/996,097, filed Jun. 20, 2013.
U.S. Response to Restriction dated Jul. 8, 2014 in U.S. Appl. No. 13/996,097, filed Jun. 20, 2013.
U.S. Office Action dated Sep. 29, 2014 in U.S. Appl. No. 13/996,097, filed Jun. 20, 2013.
U.S. Response dated Mar. 2, 2015 in U.S. Appl. No. 13/996,097, filed Jun. 20, 2013.
U.S. Office Action dated May 1, 2015 in U.S. Appl. No. 13/996,097, filed Jun. 20, 2013.
U.S. Response dated Oct. 8, 2015 in U.S. Appl. No. 13/996,097, filed Jun. 20, 2013.
U.S. Office Action dated Aug. 16, 2016 in U.S. Appl. No. 13/996,097, filed Jun. 20, 2013.
U.S. Response dated Nov. 18, 2016 in U.S. Appl. No. 13/996,097, filed Jun. 20, 2013.
U.S. Office Action dated Dec. 20, 2016 in U.S. Appl. No. 13/996,097, filed Jun. 20, 2013.
U.S. Response dated Apr. 20, 2017 in U.S. Appl. No. 13/996,097, filed Jun. 20, 2013.
U.S. Office Action dated Jun. 8, 2017 in U.S. Appl. No. 13/996,097, filed Jun. 20, 2013.
U.S. Response dated Sep. 7, 2017 in U.S. Appl. No. 13/996,097, filed Jun. 20, 2013.
U.S. Office Action dated Dec. 13, 2017 in U.S. Appl. No. 13/996,097, filed Jun. 20, 2013.
U.S. Response dated Jun. 8, 2018 in U.S. Appl. No. 13/996,097, filed Jun. 20, 2013.
U.S. Office Action dated Sep. 17, 2018 in U.S. Appl. No. 13/996,097, filed Jun. 20, 2013.
Notice of Appeal filed Mar. 15, 2019 in U.S. Appl. No. 13/996,097, filed Jun. 20, 2013.
Appeal Brief filed Jun. 10, 2019 and Revision filed Jul. 8, 2019 in U.S. Appl. No. 13/996,097, filed Jun. 20, 2013.
Examiner's Answer on Appeal Brief dated Nov. 7, 2019 in U.S. Appl. No. 13/996,097, filed Jun. 20, 2013.
U.S. Office Action dated Mar. 8, 2017 in U.S. Appl. No. 14/939,650, filed Nov. 12, 2015.
U.S. Response dated Jun. 15, 2017 in U.S. Appl. No. 14/939,650, filed Nov. 12, 2015.
U.S. Office Action dated Aug. 2, 2017 in U.S. Appl. No. 14/939,650, filed Nov. 12, 2015.
U.S. Response dated Dec. 1, 2017 in U.S. Appl. No. 14/939,650, filed Nov. 12, 2015.
U.S. Office Action dated Mar. 8, 2018 in U.S. Appl. No. 14/939,650, filed Nov. 12, 2015.
U.S. Response dated Jun. 7, 2018 in U.S. Appl. No. 14/939,650, filed Nov. 12, 2015.
U.S. Office Action dated Jul. 19, 2018 in U.S. Appl. No. 14/939,650, filed Nov. 12, 2015.
U.S. Response dated Jan. 15, 2019 in U.S. Appl. No. 14/939,650, filed Nov. 12, 2015.
U.S. Office Action dated Aug. 6, 2019 in U.S. Appl. No. 14/939,650, filed Nov. 12, 2015.
U.S. Response dated Jan. 3, 2020 in U.S. Appl. No. 14/939,650, filed Nov. 12, 2015.
U.S. Notice of Allowance dated Jan. 16, 2020 in U.S. Appl. No. 14/939,650, filed Nov. 12, 2015.
European Notice of Opposition by AbbVie, Inc. dated Feb. 15, 2019 against EP Patent No. 2654789, granted May 30, 2018 (4 pages).
European Opposition Brief by AbbVie, Inc. dated Feb. 26, 2019 against EP Patent No. 2654789, granted May 30, 2018 (35 pages).
European Notice of Opposition by Tizona Therapeutics, Inc. dated Feb. 15, 2019 against EP Patent No. 2654789, granted May 30, 2018 (6 pages).
European Opposition Brief by Tizona Therapeutics, Inc. dated Feb. 26, 2019 against EP Patent No. 2654789, granted May 30, 2018 (25 pages).
European Notice of Opposition by D Young & Co LLP. dated Feb. 28, 2019 against EP Patent No. 2654789, granted May 30, 2018 (8 pages).
European Opposition Brief by D Young & Co LLP dated Feb. 28, 2019 against EP Patent No. 2654789, granted May 30, 2018 (53 pages).
European Notice of Opposition by Boult Wade Tennant LLP. dated Feb. 28, 2019 against EP Patent No. 2654789, granted May 30, 2018 (8 pages).
European Opposition Brief by Boult Wade Tennant LLP dated Feb. 28, 2019 against EP Patent No. 2654789, granted May 30, 2018 (25 pages).
Beyer et al., "Crystal structures of the pro-inflammatory cytokine interleukin-23 and its complex with a high-affinity neutralizing antibody." J Mol Biol. (2008) 382(4): 942-955.
Bowers et al., "Crystal structures of the pro-inflammatory cytokine interleukin-23 and its complex with a high-affinity neutralizing antibody." J Biol Chem. (2014) 289: 33557-33567.
Hato et al., "Molecular Pathways: The Immunogenic Effects of Platinum-Based Chemotherapeutics", Clin Cancer Res. (2014) 20(11): 2831-2837.

(56) References Cited

OTHER PUBLICATIONS

Jardine et al., "Rational HIV immunogen design to target specific germline B cell receptors." Science (2013) 340: 711-716.
Larsen et al., "Crystal structure of a cocaine-binding antibody." J Mol Biol. (2001) 311(1): 9-15.
Lévesque et al., "Specificity of the ecto-ATPase inhibitor ARL 67156 on human and mouse ectonucleotidases." Br. J. Pharmacol. (2007) 152: 141-150.
Nicoletto et al., "Phase II Study of Pegylated Liposomal Doxorubicin and Oxaliplatin in Relapsed Advanced Ovarian Cancer", Gynecol Oncol. (2006) 100(2): 318-323.
Teplyakov et al., "Antibody modeling assessment II. Structures and models." Proteins: Struct, Function Bioinfo. (2014) 82(8): 1563-1582.
Ultsch et al., "Structural basis of signaling blockade by anti-IL-13 antibody lebrikizumab." J Mol Biol. (2013) 425(8): 1330-1339.
Yegutkin et al., "Metabolism of circulating ADP in the bloodstream is mediated via integrated actions of soluble adenylate kinase-1 and NTPDase1/CD39 activities." FASEB J. (2012) 26(9): 3875-3883.
PTAB Decision on Appeal dated Oct. 29, 2020 in U.S. Appl. No. 13/996,097, filed Jun. 20, 2013.
U.S. Office Action dated May 11, 2020 in U.S. Appl. No. 15/778,202, filed May 22, 2018.
U.S. Response dated Jan. 25, 2021 in U.S. Appl. No. 15/778,202, filed May 22, 2018.
U.S. Office Action dated Feb. 5, 2021 in U.S. Appl. No. 15/778,202, filed May 22, 2018.
U.S. Response dated Jul. 6, 2021 in U.S. Appl. No. 15/778,202, filed May 22, 2018.
U.S. Office Action dated Jul. 15, 2021 in U.S. Appl. No. 15/778,202, filed May 22, 2018.
U.S. Response dated Nov. 29, 2021 in U.S. Appl. No. 15/778,202, filed May 22, 2018.
U.S. Office Action dated Dec. 14, 2021 in U.S. Appl. No. 15/778,202, filed May 22, 2018.
U.S. Office Action dated Apr. 7, 2021 in U.S. Appl. No. 16/370,726, filed Mar. 29, 2019.
U.S. Response dated Aug. 9, 2021 in U.S. Appl. No. 16/370,726, filed Mar. 29, 2019.
U.S. Office Action dated Oct. 12, 2021 in U.S. Appl. No. 16/370,726, filed Mar. 29, 2019.
U.S. Office Action dated Nov. 30, 2020 in U.S. Appl. No. 16/370,789, filed Mar. 29, 2019.
U.S. Response dated May 27, 2021 in U.S. Appl. No. 16/370,789, filed Mar. 29, 2019.
U.S. Office Action dated Jul. 27, 2021 in U.S. Appl. No. 16/370,789, filed Mar. 29, 2019.
U.S. Office Action dated Apr. 19, 2021 in U.S. Appl. No. 16/443,744, filed Jun. 17, 2019.
U.S. Response dated Jul. 20, 2021 in U.S. Appl. No. 16/443,744, filed Jun. 17, 2019.
U.S. Office Action dated Aug. 3, 2021 in U.S. Appl. No. 16/443,744, filed Jun. 17, 2019.
Patent Proprietor's Response dated Sep. 19, 2019 to AbbVie, Inc. Opposition in re EP 2654789, granted May 30, 2018 (30 pages).
Opposer's Reply to Patent Proprietor's Response dated Oct. 17, 2019 in re EP 2654789, granted May 30, 2018 (36 pages).
Bastid et al., Inhibition of CD39 Enzymatic Function at the Surface of Tumor Cells Alleviates Their Immunosuppressive Activity. Cancer Immunol Res. (2014) 3(3):254-265.
Drosopoulos et al., Site-directed mutagenesis of human endothelial cell ecto-ADPase/soluble CD39: requirement of glutamate 174 and serine 218 for enzyme activity and inhibition of platelet recruitment. Biochemistry (2000) 39(23):6936-6943.
Häusler et al., Anti-CD39 and anti-CD73 antibodies A1 and 7G2 improve targeted therapy in ovarian cancer by blocking adenosine-dependent immune evasion. Am J Transl Res. (2014) 6(2):129-139.
Mizumoto et al., CD39 is the dominant Langerhans cell-associated ecto-NTPDase: modulatory roles in inflammation and immune responsiveness. Nat Med. (2002) 8(4):358-365.
Perrot et al., Preclinical development of humanized CD39 (IPH52) and CD73 (IPH53) blocking antibodies targeting the ATP/Adenosine immune checkpoint pathway for cancer immunotherapy. AACR 2018 Innate Pharma, Retrieved from the Internet: URL: https://www.innate-pharma.com/sites/default/files/poster_cd39_cd73_bat.pdf. Poster; 1 page.
International Search Report and Written Opinion dated Aug. 23, 2018 for Application No. PCT/EP2018/056661, filed Mar. 16, 2018.
International Preliminary Report on Patentability dated Sep. 17, 2019 for Application No. PCT/EP2018/056661, filed Mar. 16, 2018.
CDC—Centers for Disease Control & Prevention, "What is Colorectal Cancer?", downloaded from https://www.cdc.gov/cancer/colorectal/basic_info/what-is-colorectal-cancer.htm#: on Feb. 17, 2022, 1 page.
Taylor et al., "Oxaliplatin salvage for recurrent ovarian cancer: A single institution's experience in patient populations with platinum resistant disease or a history of platinum hypersensitivity", Gyn Oncol. (Jul. 1, 2014) 134(1): 68-72.
U.S. Response dated Mar. 25, 2022 in U.S. Appl. No. 15/778,202, filed May 22, 2018.
U.S. Notice of Allowance dated Apr. 13, 2022 in U.S. Appl. No. 15/778,202, filed May 22, 2018.
U.S. Response dated Feb. 11, 2022 in U.S. Appl. No. 16/370,726, filed Mar. 29, 2019.
U.S. Notice of Allowance dated May 25, 2022 in U.S. Appl. No. 16/370,726, filed Mar. 29, 2019.
U.S. Response dated Jan. 27, 2022 in U.S. Appl. No. 16/443,744, filed Jun. 17, 2019.
U.S. Notice of Allowance dated Feb. 18, 2022 in U.S. Appl. No. 16/443,744, filed Jun. 17, 2019.

* cited by examiner

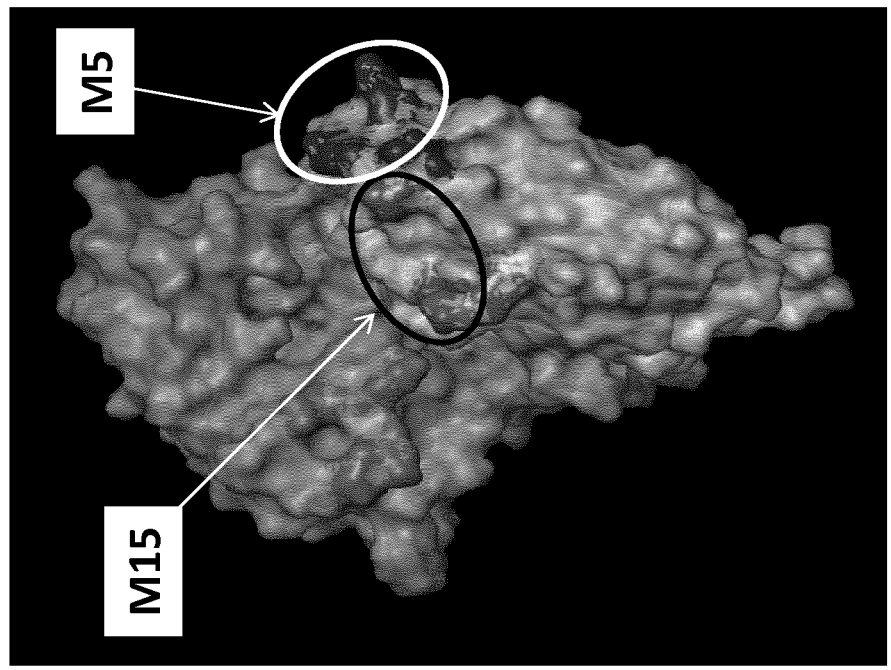
Figure 3A
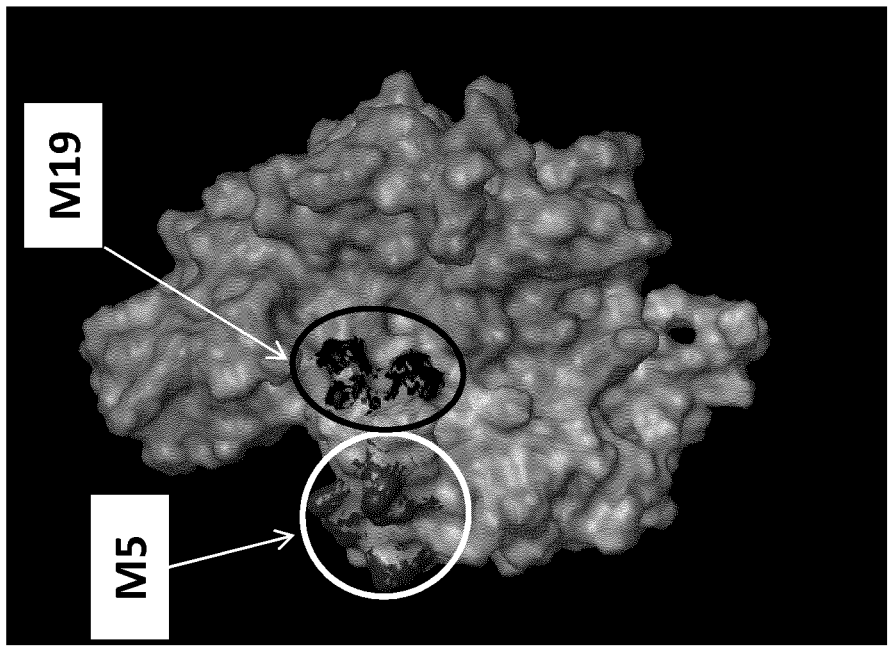

Figure 3B
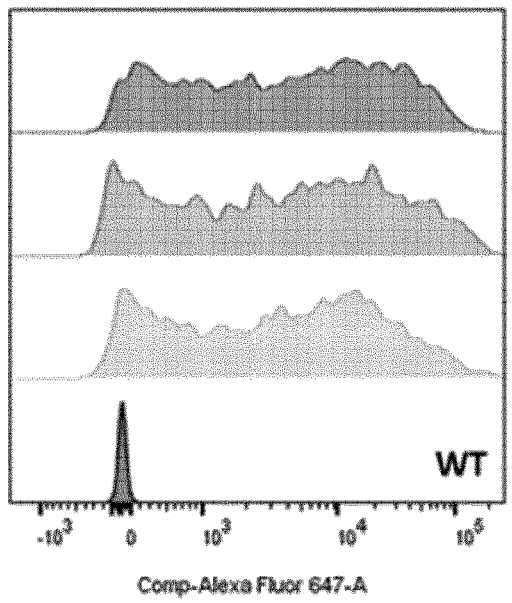
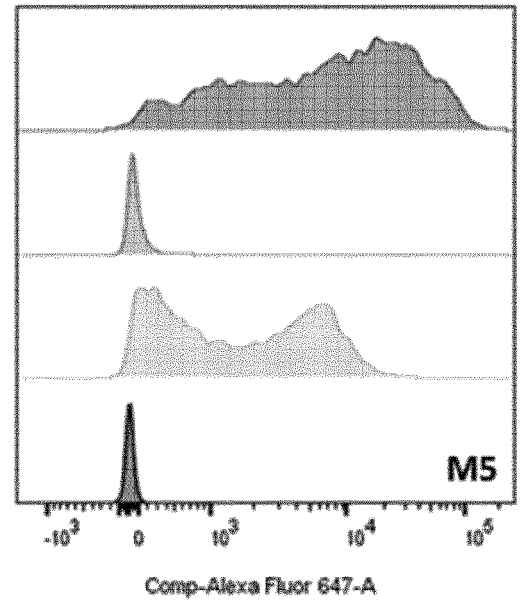
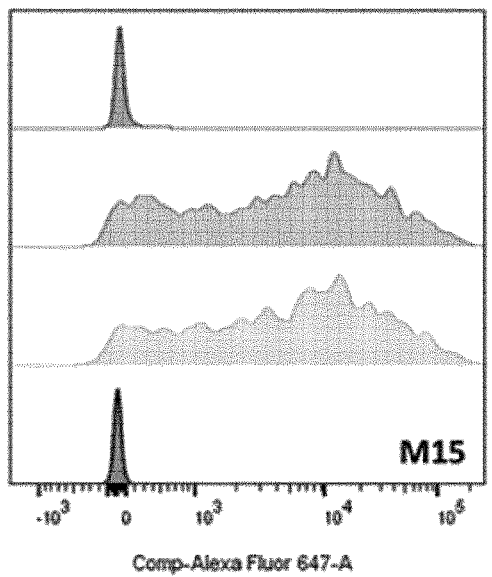
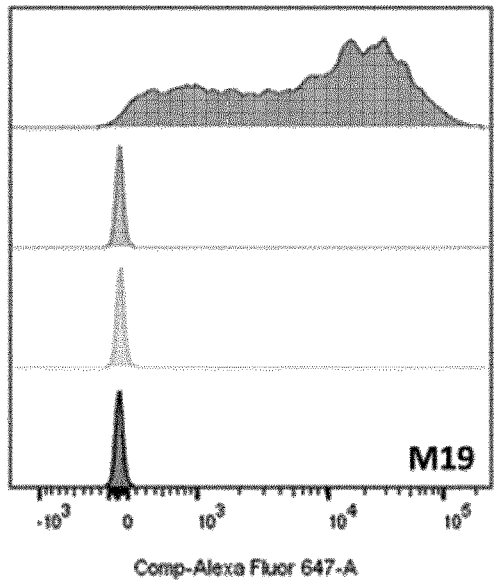

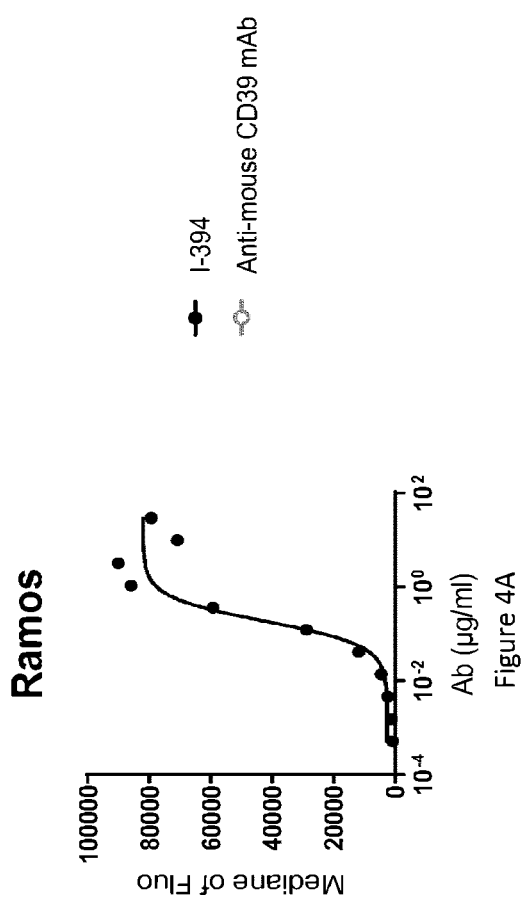
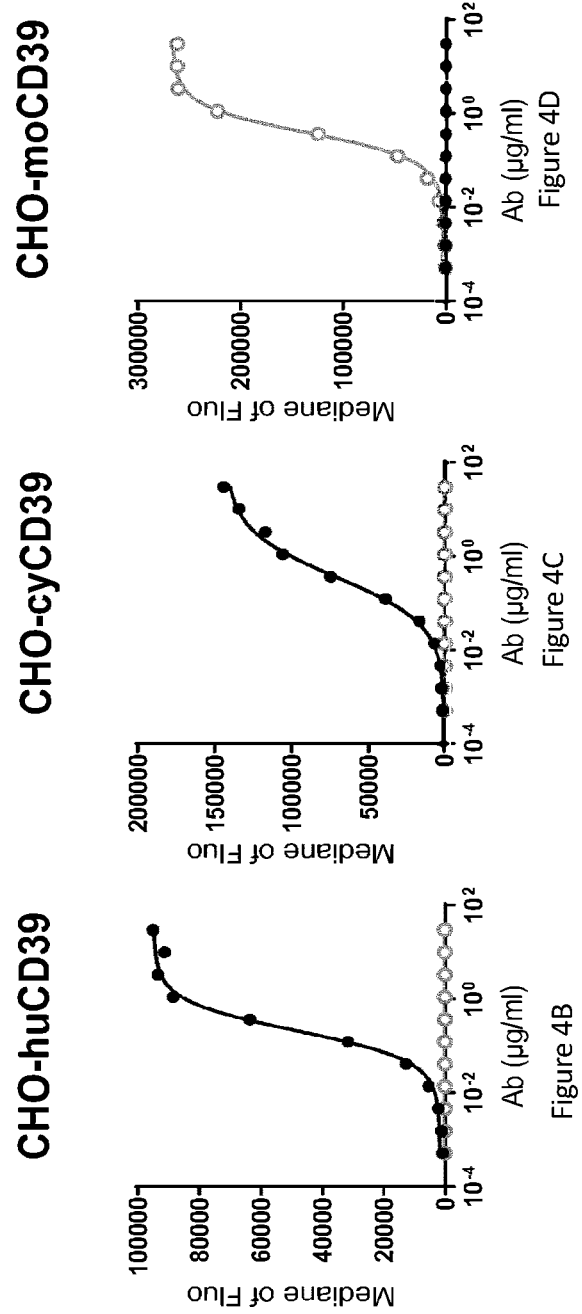

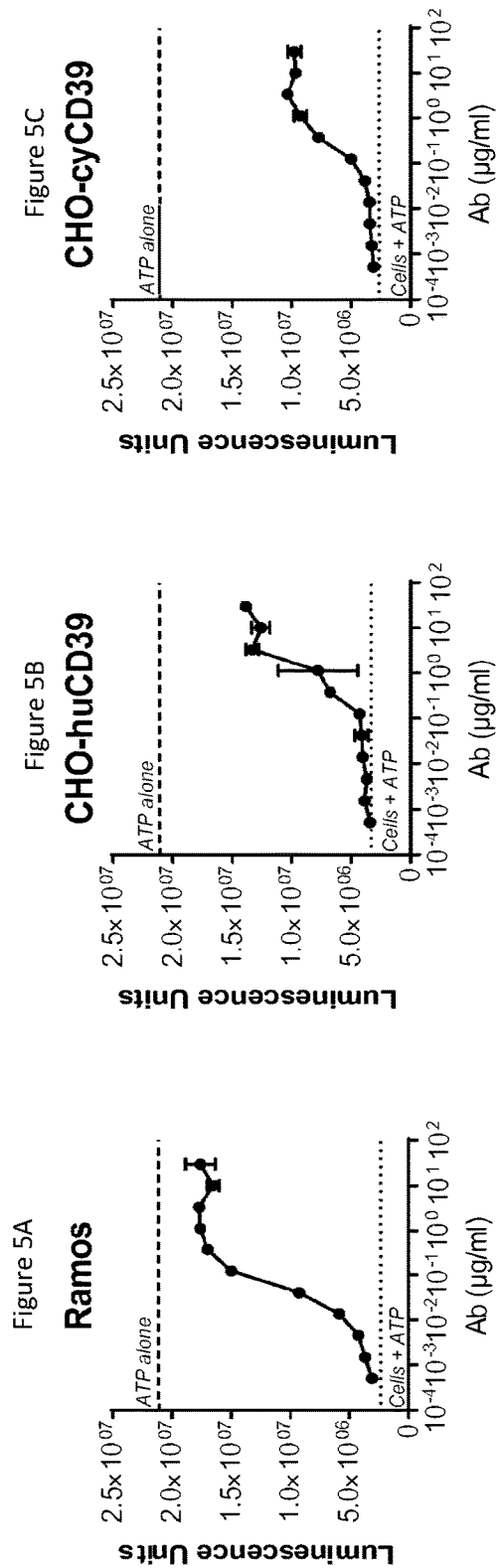

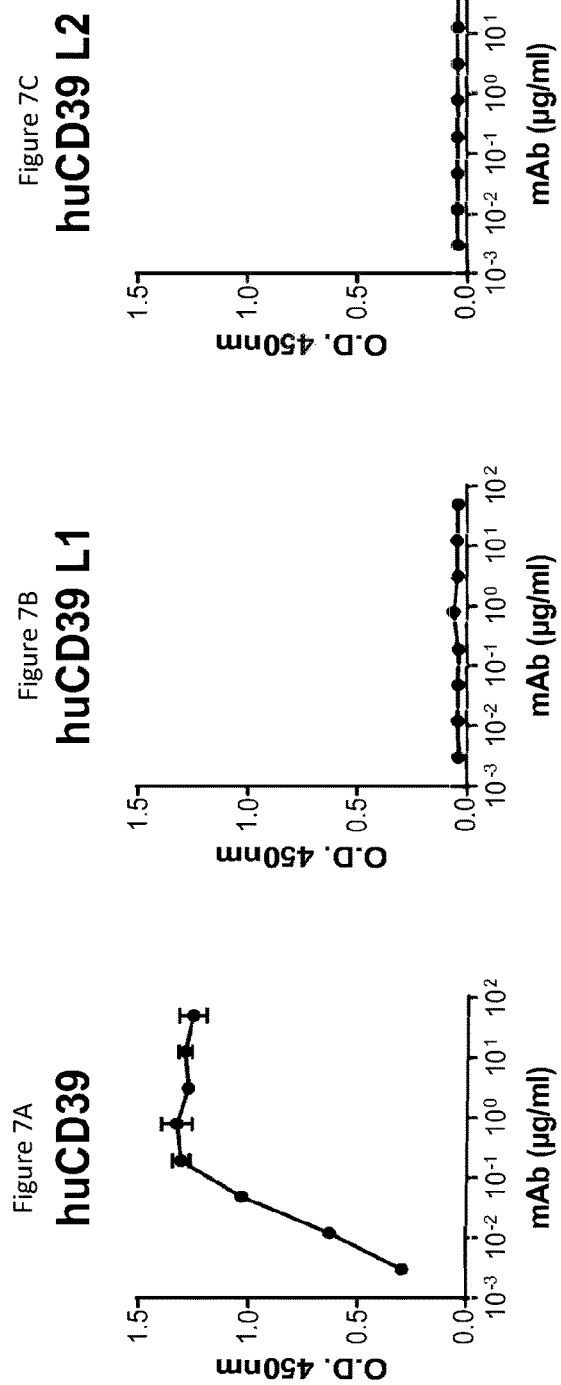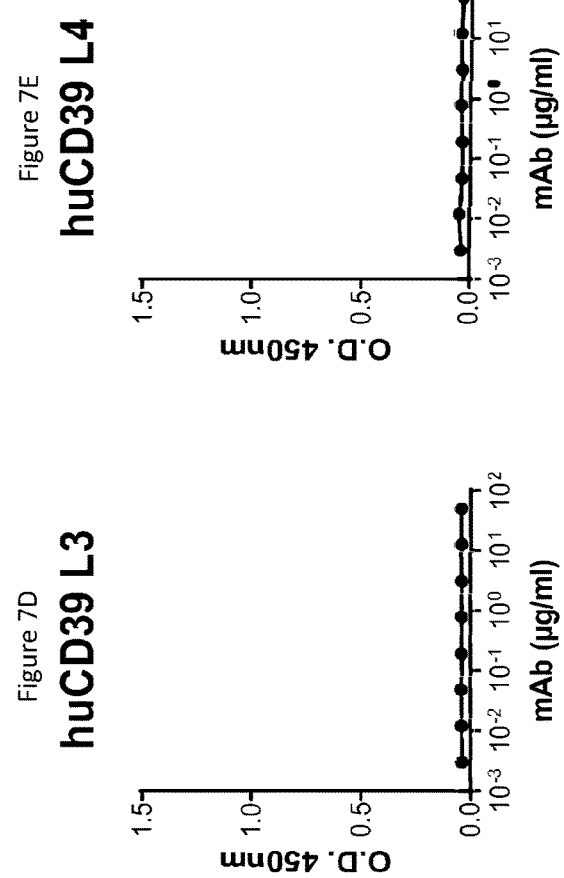

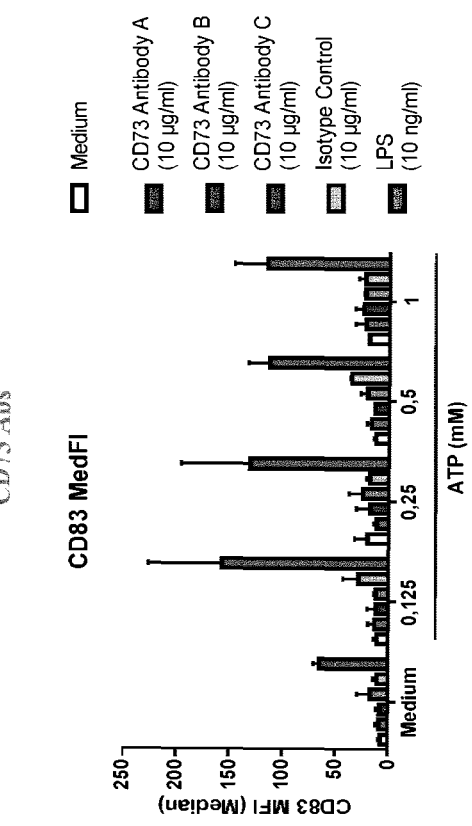
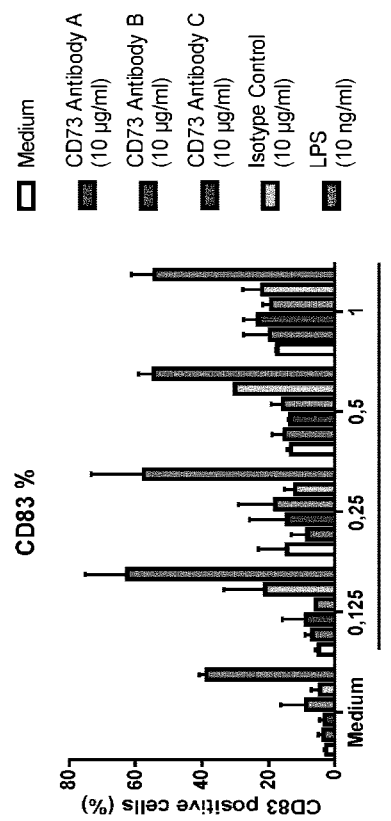
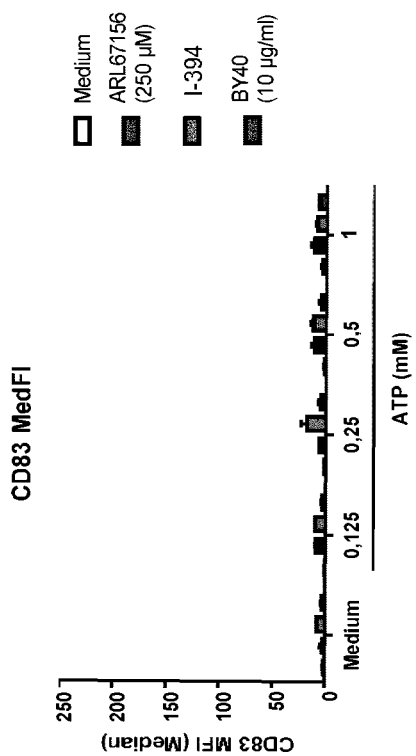
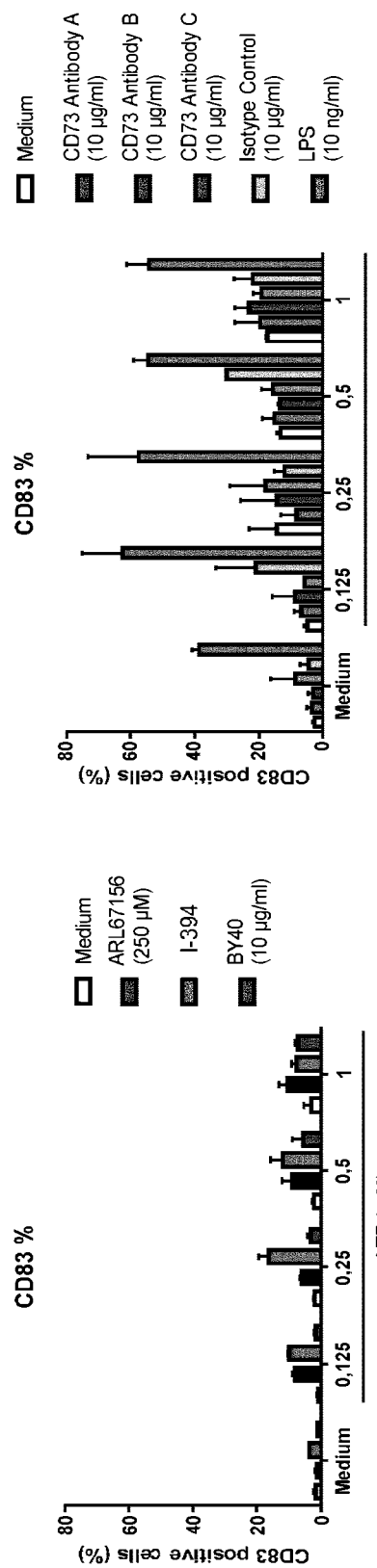
Figure 10A
Figure 10B
Figure 10C
Figure 10D

SEQUENCE LISTING

```
<160> NUMBER OF SEQ ID NOS: 45

<210> SEQ ID NO 1
<211> LENGTH: 510
<212> TYPE: PRT
<213> ORGANISM: HOMO SAPIENS

<400> SEQUENCE: 1

Met Glu Asp Thr Lys Glu Ser Asn Val Lys Thr Phe Cys Ser Lys Asn
1               5                   10                  15

Ile Leu Ala Ile Leu Gly Phe Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60
```

```
Tyr Lys Trp Pro Ala Glu Lys Glu Asn Asp Thr Gly Val Val His Gln
 65                  70                  75                  80

Val Glu Glu Cys Arg Val Lys Gly Pro Gly Ile Ser Lys Phe Val Gln
                 85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480
```

```
Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510

<210> SEQ ID NO 2
<211> LENGTH: 472
<212> TYPE: PRT
<213> ORGANISM: HOMO SAPIENS

<400> SEQUENCE: 2

Met Ala Gly Lys Val Arg Ser Leu Leu Pro Leu Leu Leu Ala Ala
1               5                   10                  15

Ala Gly Leu Ala Gly Leu Leu Leu Cys Val Pro Thr Arg Asp Val
                20                  25                  30

Arg Glu Pro Pro Ala Leu Lys Tyr Gly Ile Val Leu Asp Ala Gly Ser
            35                  40                  45

Ser His Thr Ser Met Phe Ile Tyr Lys Trp Pro Ala Asp Lys Glu Asn
50                  55                  60

Asp Thr Gly Ile Val Gly Gln His Ser Ser Cys Asp Val Pro Gly Gly
65                  70                  75                  80

Gly Ile Ser Ser Tyr Ala Asp Asn Pro Ser Gly Ala Ser Gln Ser Leu
                85                  90                  95

Val Gly Cys Leu Glu Gln Ala Leu Gln Asp Val Pro Lys Glu Arg His
                100                 105                 110

Ala Gly Thr Pro Leu Tyr Leu Gly Ala Thr Ala Gly Met Arg Leu Leu
                115                 120                 125

Asn Leu Thr Asn Pro Glu Ala Ser Thr Ser Val Leu Met Ala Val Thr
    130                 135                 140

His Thr Leu Thr Gln Tyr Pro Phe Asp Phe Arg Gly Ala Arg Ile Leu
145                 150                 155                 160

Ser Gly Gln Glu Glu Gly Val Phe Gly Trp Val Thr Ala Asn Tyr Leu
                165                 170                 175

Leu Glu Asn Phe Ile Lys Tyr Gly Trp Val Gly Arg Trp Phe Arg Pro
                180                 185                 190

Arg Lys Gly Thr Leu Gly Ala Met Asp Leu Gly Gly Ala Ser Thr Gln
            195                 200                 205

Ile Thr Phe Glu Thr Thr Ser Pro Ala Glu Asp Arg Ala Ser Glu Val
210                 215                 220

Gln Leu His Leu Tyr Gly Gln His Tyr Arg Val Tyr Thr His Ser Phe
225                 230                 235                 240

Leu Cys Tyr Gly Arg Asp Gln Val Leu Gln Arg Leu Leu Ala Ser Ala
                245                 250                 255

Leu Gln Thr His Gly Phe His Pro Cys Trp Pro Arg Gly Phe Ser Thr
                260                 265                 270

Gln Val Leu Leu Gly Asp Val Tyr Gln Ser Pro Cys Thr Met Ala Gln
            275                 280                 285

Arg Pro Gln Asn Phe Asn Ser Ser Ala Arg Val Ser Leu Ser Gly Ser
290                 295                 300

Ser Asp Pro His Leu Cys Arg Asp Leu Val Ser Gly Leu Phe Ser Phe
305                 310                 315                 320

Ser Ser Cys Pro Phe Ser Arg Cys Ser Phe Asn Gly Val Phe Gln Pro
                325                 330                 335

Pro Val Ala Gly Asn Phe Val Ala Phe Ser Ala Phe Phe Tyr Thr Val
                340                 345                 350
```

Asp Phe Leu Arg Thr Ser Met Gly Leu Pro Val Ala Thr Leu Gln Gln
                355                 360                 365

Leu Glu Ala Ala Val Asn Val Cys Asn Gln Thr Trp Ala Gln Gln
370                 375                 380

Leu Leu Ser Arg Gly Tyr Gly Phe Asp Glu Arg Ala Phe Gly Gly Val
385                 390                 395                 400

Ile Phe Gln Lys Lys Ala Ala Asp Thr Ala Val Gly Trp Ala Leu Gly
                405                 410                 415

Tyr Met Leu Asn Leu Thr Asn Leu Ile Pro Ala Asp Pro Gly Leu
                420                 425                 430

Arg Lys Gly Thr Asp Phe Ser Ser Trp Val Val Leu Leu Leu Phe
        435                 440                 445

Ala Ser Ala Leu Leu Ala Leu Val Leu Leu Arg Gln Val His
    450                 455                 460

Ser Ala Lys Leu Pro Ser Thr Ile
465                 470

<210> SEQ ID NO 3
<211> LENGTH: 484
<212> TYPE: PRT
<213> ORGANISM: HOMO SAPIENS

<400> SEQUENCE: 3

Met Lys Lys Gly Ile Arg Tyr Glu Thr Ser Arg Lys Thr Ser Tyr Ile
1               5                   10                  15

Phe Gln Gln Pro Gln His Gly Pro Trp Gln Thr Arg Met Arg Lys Ile
                20                  25                  30

Ser Asn His Gly Ser Leu Arg Val Ala Lys Val Ala Tyr Pro Leu Gly
            35                  40                  45

Leu Cys Val Gly Val Phe Ile Tyr Val Ala Tyr Ile Lys Trp His Arg
50                  55                  60

Ala Thr Ala Thr Gln Ala Phe Phe Ser Ile Thr Arg Ala Ala Pro Gly
65                  70                  75                  80

Ala Arg Trp Gly Gln Gln Ala His Ser Pro Leu Gly Thr Ala Ala Asp
                85                  90                  95

Gly His Glu Val Phe Tyr Gly Ile Met Phe Asp Ala Gly Ser Thr Gly
            100                 105                 110

Thr Arg Val His Val Phe Gln Phe Thr Arg Pro Pro Arg Glu Thr Pro
        115                 120                 125

Thr Leu Thr His Glu Thr Phe Lys Ala Leu Lys Pro Gly Leu Ser Ala
    130                 135                 140

Tyr Ala Asp Asp Val Glu Lys Ser Ala Gln Gly Ile Arg Glu Leu Leu
145                 150                 155                 160

Asp Val Ala Lys Gln Asp Ile Pro Phe Asp Phe Trp Lys Ala Thr Pro
                165                 170                 175

Leu Val Leu Lys Ala Thr Ala Gly Leu Arg Leu Leu Pro Gly Glu Lys
            180                 185                 190

Ala Gln Lys Leu Leu Gln Lys Val Lys Glu Val Phe Lys Ala Ser Pro
        195                 200                 205

Phe Leu Val Gly Asp Asp Cys Val Ser Ile Met Asn Gly Thr Asp Glu
    210                 215                 220

Gly Val Ser Ala Trp Ile Thr Ile Asn Phe Leu Thr Gly Ser Leu Lys
225                 230                 235                 240

Thr Pro Gly Gly Ser Ser Val Gly Met Leu Asp Leu Gly Gly Gly Ser
                245                 250                 255

```
Thr Gln Ile Ala Phe Leu Pro Arg Val Glu Gly Thr Leu Gln Ala Ser
            260                 265                 270

Pro Pro Gly Tyr Leu Thr Ala Leu Arg Met Phe Asn Arg Thr Tyr Lys
        275                 280                 285

Leu Tyr Ser Tyr Ser Tyr Leu Gly Leu Gly Leu Met Ser Ala Arg Leu
    290                 295                 300

Ala Ile Leu Gly Gly Val Gly Gln Pro Ala Lys Asp Gly Lys Glu
305                 310                 315                 320

Leu Val Ser Pro Cys Leu Ser Pro Ser Phe Lys Gly Glu Trp Glu His
                325                 330                 335

Ala Glu Val Thr Tyr Arg Val Ser Gly Gln Lys Ala Ala Ser Leu
            340                 345                 350

His Glu Leu Cys Ala Ala Arg Val Ser Glu Val Leu Gln Asn Arg Val
        355                 360                 365

His Arg Thr Glu Glu Val Lys His Val Asp Phe Tyr Ala Phe Ser Tyr
    370                 375                 380

Tyr Tyr Asp Leu Ala Ala Gly Val Gly Leu Ile Asp Ala Glu Lys Gly
385                 390                 395                 400

Gly Ser Leu Val Val Gly Asp Phe Glu Ile Ala Ala Lys Tyr Val Cys
                405                 410                 415

Arg Thr Leu Glu Thr Gln Pro Gln Ser Ser Pro Phe Ser Cys Met Asp
            420                 425                 430

Leu Thr Tyr Val Ser Leu Leu Leu Gln Glu Phe Gly Phe Pro Arg Ser
        435                 440                 445

Lys Val Leu Lys Leu Thr Arg Lys Ile Asp Asn Val Glu Thr Ser Trp
    450                 455                 460

Ala Leu Gly Ala Ile Phe His Tyr Ile Asp Ser Leu Asn Arg Gln Lys
465                 470                 475                 480

Ser Pro Ala Ser

<210> SEQ ID NO 4
<211> LENGTH: 529
<212> TYPE: PRT
<213> ORGANISM: HOMO SAPIENS

<400> SEQUENCE: 4

Met Phe Thr Val Leu Thr Arg Gln Pro Cys Glu Gln Ala Gly Leu Lys
1               5                   10                  15

Ala Leu Tyr Arg Thr Pro Thr Ile Ile Ala Leu Val Val Leu Leu Val
            20                  25                  30

Ser Ile Val Val Leu Val Ser Ile Thr Val Ile Gln Ile His Lys Gln
        35                  40                  45

Glu Val Leu Pro Pro Gly Leu Lys Tyr Gly Ile Val Leu Asp Ala Gly
    50                  55                  60

Ser Ser Arg Thr Thr Val Tyr Val Tyr Gln Trp Pro Ala Glu Lys Glu
65                  70                  75                  80

Asn Asn Thr Gly Val Val Ser Gln Thr Phe Lys Cys Ser Val Lys Gly
                85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
        115                 120                 125

His Gly Ser Thr Pro Ile His Leu Gly Ala Thr Ala Gly Met Arg Leu
    130                 135                 140
```

```
Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
            180                 185                 190

Leu Met Gly Asn Phe Leu Glu Lys Asn Leu Trp His Met Trp Val His
        195                 200                 205

Pro His Gly Val Glu Thr Thr Gly Ala Leu Asp Leu Gly Gly Ala Ser
    210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
            260                 265                 270

Ala Met Leu Leu Gln Asn Ser Pro Thr Lys Asn His Leu Thr Asn Pro
        275                 280                 285

Cys Tyr Pro Arg Asp Tyr Ser Ile Ser Phe Thr Met Gly His Val Phe
    290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
            340                 345                 350

Cys Ser Phe Asp Gly Val Tyr Gln Pro Lys Ile Lys Gly Pro Phe Val
        355                 360                 365

Ala Phe Ala Gly Phe Tyr Tyr Thr Ala Ser Ala Leu Asn Leu Ser Gly
    370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Leu Pro Lys Phe Asp Glu Val
                405                 410                 415

Tyr Ala Arg Ser Tyr Cys Phe Ser Ala Asn Tyr Ile Tyr His Leu Phe
            420                 425                 430

Val Asn Gly Tyr Lys Phe Thr Glu Glu Thr Trp Pro Gln Ile His Phe
        435                 440                 445

Glu Lys Glu Val Gly Asn Ser Ser Ile Ala Trp Ser Leu Gly Tyr Met
    450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Ala
                485                 490                 495

Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
        515                 520                 525

Asp

<210> SEQ ID NO 5
<211> LENGTH: 428
<212> TYPE: PRT
<213> ORGANISM: HOMO SAPIENS
```

<400> SEQUENCE: 5

```
Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
            20                  25                  30

Ile Phe Leu Ser Ser Met Cys Pro Ile Asn Val Ser Ala Ser Thr Leu
        35                  40                  45

Tyr Gly Ile Met Phe Asp Ala Gly Ser Thr Gly Thr Arg Ile His Val
    50                  55                  60

Tyr Thr Phe Val Gln Lys Met Pro Gly Gln Leu Pro Ile Leu Glu Gly
65                  70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
    210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270

Leu Pro Arg Trp Leu Glu Ala Glu Trp Ile Phe Gly Gly Val Lys Tyr
        275                 280                 285

Gln Tyr Gly Gly Asn Gln Glu Gly Glu Val Gly Phe Glu Pro Cys Tyr
    290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Tyr Asp Arg Ala
                325                 330                 335

Val Asp Thr Asp Met Ile Asp Tyr Glu Lys Gly Gly Ile Leu Lys Val
            340                 345                 350

Glu Asp Phe Glu Arg Lys Ala Arg Glu Val Cys Asp Asn Leu Glu Asn
        355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400
```

```
Leu Thr Lys Lys Val Asn Asn Ile Glu Thr Gly Trp Ala Leu Gly Ala
                405                 410                 415

Thr Phe His Leu Leu Gln Ser Leu Gly Ile Ser His
            420                 425
```

<210> SEQ ID NO 6
<211> LENGTH: 116
<212> TYPE: PRT
<213> ORGANISM: MUS MUSCULUS

<400> SEQUENCE: 6

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Arg Thr Leu Glu Trp Ile
        35                  40                  45

Gly Tyr Ile Val Pro Leu Asn Gly Gly Ser Thr Phe Asn Gln Lys Phe
    50                  55                  60

Lys Gly Arg Ala Thr Leu Thr Val Asn Thr Ser Ser Arg Thr Ala Tyr
65                  70                  75                  80

Met Glu Leu Arg Ser Leu Thr Ser Glu Asp Ser Ala Ala Tyr Tyr Cys
                85                  90                  95

Ala Arg Gly Gly Thr Arg Phe Ala Tyr Trp Gly Gln Gly Thr Leu Val
            100                 105                 110

Thr Val Ser Ala
        115
```

<210> SEQ ID NO 7
<211> LENGTH: 111
<212> TYPE: PRT
<213> ORGANISM: MUS MUSCULUS

<400> SEQUENCE: 7

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Val Ser Phe Met Tyr Trp Phe Gln Gln Lys Pro Gly Gln Pro Pro
        35                  40                  45

Asn Leu Leu Ile Tyr Gly Ala Ser Asn Gln Gly Ser Gly Val Pro Ala
    50                  55                  60

Arg Phe Arg Gly Ser Gly Ser Gly Thr Asp Phe Ser Leu Asn Ile His
65                  70                  75                  80

Pro Met Glu Ala Asp Asp Thr Ala Met Tyr Phe Cys Gln Gln Thr Lys
                85                  90                  95

Glu Val Pro Tyr Thr Phe Gly Gly Gly Thr Lys Leu Glu Ile Lys
            100                 105                 110
```

<210> SEQ ID NO 8
<211> LENGTH: 5
<212> TYPE: PRT
<213> ORGANISM: MUS MUSCULUS

<400> SEQUENCE: 8

```
Asp Tyr Asn Met His
1               5
```

```
<210> SEQ ID NO 9
<211> LENGTH: 17
<212> TYPE: PRT
<213> ORGANISM: Mus musculus

<400> SEQUENCE: 9

Tyr Ile Val Pro Leu Asn Gly Gly Ser Thr Phe Asn Gln Lys Phe Lys
1               5                   10                  15

Gly

<210> SEQ ID NO 10
<211> LENGTH: 7
<212> TYPE: PRT
<213> ORGANISM: Mus musculus

<400> SEQUENCE: 10

Gly Gly Thr Arg Phe Ala Tyr
1               5

<210> SEQ ID NO 11
<211> LENGTH: 15
<212> TYPE: PRT
<213> ORGANISM: Mus musculus

<400> SEQUENCE: 11

Arg Ala Ser Glu Ser Val Asp Asn Phe Gly Val Ser Phe Met Tyr
1               5                   10                  15

<210> SEQ ID NO 12
<211> LENGTH: 7
<212> TYPE: PRT
<213> ORGANISM: Mus musculus

<400> SEQUENCE: 12

Gly Ala Ser Asn Gln Gly Ser
1               5

<210> SEQ ID NO 13
<211> LENGTH: 9
<212> TYPE: PRT
<213> ORGANISM: Mus musculus

<400> SEQUENCE: 13

Gln Gln Thr Lys Glu Val Pro Tyr Thr
1               5

<210> SEQ ID NO 14
<211> LENGTH: 116
<212> TYPE: PRT
<213> ORGANISM: Mus musculus

<400> SEQUENCE: 14

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Asn Met His Trp Val Lys Lys Asn His Gly Lys Gly Leu Glu Trp Ile
        35                  40                  45

Gly Tyr Ile Asn Pro Asn Asn Gly Gly Thr Tyr Asn Gln Lys Phe
    50                  55                  60

Lys Gly Lys Ala Thr Leu Thr Val Asn Thr Ser Ser Lys Thr Ala Tyr
65                  70                  75                  80
```

```
Met Glu Leu Arg Ser Leu Thr Ser Glu Asp Ser Ala Val Tyr Tyr Cys
                85                  90                  95

Thr Arg Gly Gly Thr Arg Phe Ala Ser Trp Gly Gln Gly Thr Leu Val
            100                 105                 110

Thr Val Ser Ala
            115

<210> SEQ ID NO 15
<211> LENGTH: 111
<212> TYPE: PRT
<213> ORGANISM: Mus musculus

<400> SEQUENCE: 15

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Tyr Trp Phe Gln Gln Lys Pro Gly Gln Pro Pro
        35                  40                  45

Lys Leu Leu Ile Tyr Ala Ala Ser Thr Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Phe Thr Phe Gly Ser Gly Thr Lys Leu Glu Ile Lys
            100                 105                 110

<210> SEQ ID NO 16
<211> LENGTH: 5
<212> TYPE: PRT
<213> ORGANISM: Mus musculus

<400> SEQUENCE: 16

Asp Tyr Asn Met His
1               5

<210> SEQ ID NO 17
<211> LENGTH: 17
<212> TYPE: PRT
<213> ORGANISM: Mus musculus

<400> SEQUENCE: 17

Tyr Ile Asn Pro Asn Asn Gly Gly Thr Thr Tyr Asn Gln Lys Phe Lys
1               5                   10                  15

Gly

<210> SEQ ID NO 18
<211> LENGTH: 7
<212> TYPE: PRT
<213> ORGANISM: Mus musculus

<400> SEQUENCE: 18

Gly Gly Thr Arg Phe Ala Ser
1               5

<210> SEQ ID NO 19
<211> LENGTH: 15
<212> TYPE: PRT
<213> ORGANISM: Mus musculus
```

<400> SEQUENCE: 19

Arg Ala Ser Glu Ser Val Asp Asn Tyr Gly Ile Ser Phe Met Tyr
1               5                   10                  15

<210> SEQ ID NO 20
<211> LENGTH: 7
<212> TYPE: PRT
<213> ORGANISM: Mus musculus

<400> SEQUENCE: 20

Ala Ala Ser Thr Gln Gly Ser
1               5

<210> SEQ ID NO 21
<211> LENGTH: 9
<212> TYPE: PRT
<213> ORGANISM: Mus musculus

<400> SEQUENCE: 21

Gln Gln Ser Lys Glu Val Pro Phe Thr
1               5

<210> SEQ ID NO 22
<211> LENGTH: 122
<212> TYPE: PRT
<213> ORGANISM: Mus musculus

<400> SEQUENCE: 22

Glu Val Gln Leu Gln Gln Ser Gly Ala Glu Leu Val Lys Pro Gly Ala
1               5                   10                  15

Ser Val Lys Leu Ser Cys Ile Val Ser Gly Phe Asn Ile Lys Asp Thr
            20                  25                  30

Tyr Ile Asn Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Met Thr Ser Asp Thr Ser Asn Thr Ala Tyr
65                  70                  75                  80

Leu His Leu Ser Ser Leu Thr Ser Asp Asp Ser Ala Val Tyr Tyr Cys
                85                  90                  95

Ala Arg Trp Gly Tyr Asp Asp Glu Glu Ala Asp Tyr Phe Asp Ser Trp
            100                 105                 110

Gly Gln Gly Thr Thr Leu Thr Val Ser Ser
        115                 120

<210> SEQ ID NO 23
<211> LENGTH: 111
<212> TYPE: PRT
<213> ORGANISM: Mus musculus

<400> SEQUENCE: 23

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile Leu
65                  70                  75                  80

Pro Met Glu Glu Val Asp Ala Ala Met Tyr Phe Cys His Gln Ser Lys
                85                  90                  95

Glu Val Pro Trp Thr Phe Gly Gly Gly Thr Lys Leu Glu Ile Lys
            100                 105                 110

<210> SEQ ID NO 24
<211> LENGTH: 5
<212> TYPE: PRT
<213> ORGANISM: Mus musculus

<400> SEQUENCE: 24

Asp Thr Tyr Ile Asn
1               5

<210> SEQ ID NO 25
<211> LENGTH: 17
<212> TYPE: PRT
<213> ORGANISM: Mus musculus

<400> SEQUENCE: 25

Arg Ile Asp Pro Ala Asn Gly Asn Thr Lys Tyr Asp Pro Lys Phe Gln
1               5                   10                  15

Gly

<210> SEQ ID NO 26
<211> LENGTH: 13
<212> TYPE: PRT
<213> ORGANISM: Mus musculus

<400> SEQUENCE: 26

Trp Gly Tyr Asp Asp Glu Glu Ala Asp Tyr Phe Asp Ser
1               5                   10

<210> SEQ ID NO 27
<211> LENGTH: 15
<212> TYPE: PRT
<213> ORGANISM: Mus musculus

<400> SEQUENCE: 27

Arg Ala Ser Glu Ser Val Asp Asn Tyr Gly Ile Ser Phe Met Asn
1               5                   10                  15

<210> SEQ ID NO 28
<211> LENGTH: 7
<212> TYPE: PRT
<213> ORGANISM: Mus musculus

<400> SEQUENCE: 28

Ala Ala Ser Asn Gln Gly Ser
1               5

<210> SEQ ID NO 29
<211> LENGTH: 9
<212> TYPE: PRT
<213> ORGANISM: Mus musculus

<400> SEQUENCE: 29

His Gln Ser Lys Glu Val Pro Trp Thr
1               5

```
<210> SEQ ID NO 30
<211> LENGTH: 118
<212> TYPE: PRT
<213> ORGANISM: Mus musculus

<400> SEQUENCE: 30

Pro Val Gln Leu Gln Gln Pro Gly Ala Glu Val Val Met Pro Gly Ala
1               5                   10                  15

Ser Val Lys Leu Ser Cys Lys Ala Ser Gly Tyr Thr Phe Thr Ser Phe
            20                  25                  30

Trp Met Asn Trp Met Arg Gln Arg Pro Gly Gln Gly Leu Glu Trp Ile
        35                  40                  45

Gly Glu Ile Asp Pro Ser Asp Phe Tyr Thr Asn Ser Asn Gln Arg Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asp Phe Gly Trp Tyr Phe Asp Val Trp Gly Thr Gly Thr
            100                 105                 110

Ser Val Thr Val Ser Ser
            115

<210> SEQ ID NO 31
<211> LENGTH: 108
<212> TYPE: PRT
<213> ORGANISM: Mus musculus

<400> SEQUENCE: 31

Glu Ile Val Leu Thr Gln Ser Pro Thr Thr Met Thr Ser Ser Pro Gly
1               5                   10                  15

Glu Lys Ile Thr Phe Thr Cys Ser Ala Ser Ser Ser Ile Asn Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Thr Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Leu Pro
                85                  90                  95

Arg Thr Phe Gly Gly Gly Thr Lys Leu Glu Ile Lys
            100                 105

<210> SEQ ID NO 32
<211> LENGTH: 5
<212> TYPE: PRT
<213> ORGANISM: Mus musculus

<400> SEQUENCE: 32

Ser Phe Trp Met Asn
1               5

<210> SEQ ID NO 33
<211> LENGTH: 17
<212> TYPE: PRT
<213> ORGANISM: Mus musculus
```

```
<400> SEQUENCE: 33

Glu Ile Asp Pro Ser Asp Phe Tyr Thr Asn Ser Asn Gln Arg Phe Lys
1               5                   10                  15

Gly

<210> SEQ ID NO 34
<211> LENGTH: 9
<212> TYPE: PRT
<213> ORGANISM: Mus musculus

<400> SEQUENCE: 34

Gly Asp Phe Gly Trp Tyr Phe Asp Val
1               5

<210> SEQ ID NO 35
<211> LENGTH: 12
<212> TYPE: PRT
<213> ORGANISM: Mus musculus

<400> SEQUENCE: 35

Ser Ala Ser Ser Ser Ile Asn Ser Asn Tyr Leu His
1               5                   10

<210> SEQ ID NO 36
<211> LENGTH: 7
<212> TYPE: PRT
<213> ORGANISM: Mus musculus

<400> SEQUENCE: 36

Arg Thr Ser Asn Leu Ala Ser
1               5

<210> SEQ ID NO 37
<211> LENGTH: 9
<212> TYPE: PRT
<213> ORGANISM: Mus musculus

<400> SEQUENCE: 37

Gln Gln Gly Ser Ser Leu Pro Arg Thr
1               5

<210> SEQ ID NO 38
<211> LENGTH: 330
<212> TYPE: PRT
<213> ORGANISM: HOMO SAPIENS

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Ala Glu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 39
<211> LENGTH: 330
<212> TYPE: PRT
<213> ORGANISM: HOMO SAPIENS

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Ser Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 330
<212> TYPE: PRT
<213> ORGANISM: HOMO SAPIENS

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 330
<212> TYPE: PRT
<213> ORGANISM: HOMO SAPIENS

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 42
<211> LENGTH: 45
<212> TYPE: DNA
<213> ORGANISM: HOMO SAPIENS

<400> SEQUENCE: 42
tacgactcac aagcttgccg ccaccatgga agatacaaag gagtc            45

<210> SEQ ID NO 43
<211> LENGTH: 64
<212> TYPE: DNA
<213> ORGANISM: HOMO SAPIENS

<400> SEQUENCE: 43
ccgccccgac tctagatcac ttgtcatcgt catctttgta atcgacatag gtggagtggg   60
agag                                                                64

<210> SEQ ID NO 44
<211> LENGTH: 478
<212> TYPE: PRT
<213> ORGANISM: HOMO SAPIENS

<400> SEQUENCE: 44

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ala Val Ile Ala Leu
            20                  25                  30

Leu Ala Val Gly Leu Thr Gln Asn Lys Ala Leu Pro Glu Asn Val Lys
            35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
            85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175
```

Tyr Gly Trp Ile Thr Ile Asn Tyr Leu Leu Gly Lys Phe Ser Gln Lys
                180                 185                 190

Thr Arg Trp Phe Ser Ile Val Pro Tyr Glu Thr Asn Asn Gln Glu Thr
            195                 200                 205

Phe Gly Ala Leu Asp Leu Gly Gly Ala Ser Thr Gln Val Thr Phe Val
        210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
        450                 455                 460

Glu Gln Pro Leu Ser Thr Pro Leu Ser His Ser Thr Tyr Val
465                 470                 475

<210> SEQ ID NO 45
<211> LENGTH: 486
<212> TYPE: PRT
<213> ORGANISM: HOMO SAPIENS

<400> SEQUENCE: 45

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

-continued

```
Val Glu Glu Cys Arg Val Lys Gly Pro Gly Ile Ser Lys Phe Val Gln
             85                  90                  95
Lys Val Asn Glu Ile Gly Ile Tyr Leu Thr Asp Cys Met Glu Arg Ala
        100                 105                 110
Arg Glu Val Ile Pro Arg Ser Gln His Gln Glu Thr Pro Val Tyr Leu
            115                 120                 125
Gly Ala Thr Ala Gly Met Arg Leu Leu Arg Met Glu Ser Glu Glu Leu
        130                 135                 140
Ala Asp Arg Val Leu Asp Val Val Glu Arg Ser Leu Ser Asn Tyr Pro
145                 150                 155                 160
Phe Asp Phe Gln Gly Ala Arg Ile Ile Thr Gly Gln Glu Glu Gly Ala
                165                 170                 175
Tyr Gly Trp Ile Thr Ile Asn Tyr Leu Leu Gly Lys Phe Ser Gln Lys
            180                 185                 190
Thr Arg Trp Phe Ser Ile Val Pro Tyr Glu Thr Asn Asn Gln Glu Thr
        195                 200                 205
Phe Gly Ala Leu Asp Leu Gly Gly Ala Ser Thr Gln Val Thr Phe Val
210                 215                 220
Pro Gln Asn Gln Thr Ile Glu Ser Pro Asp Asn Ala Leu Gln Phe Arg
225                 230                 235                 240
Leu Tyr Gly Lys Asp Tyr Asn Val Tyr Thr His Ser Phe Leu Cys Tyr
                245                 250                 255
Gly Lys Asp Gln Ala Leu Trp Gln Lys Leu Ala Lys Asp Ile Gln Val
            260                 265                 270
Ala Ser Asn Glu Ile Leu Arg Asp Pro Cys Phe His Pro Gly Tyr Lys
        275                 280                 285
Lys Val Val Asn Val Ser Asp Leu Tyr Lys Thr Pro Cys Thr Lys Arg
290                 295                 300
Phe Glu Met Thr Leu Pro Phe Gln Gln Phe Glu Ile Gln Gly Ile Gly
305                 310                 315                 320
Asn Tyr Gln Gln Cys His Gln Ser Ile Leu Glu Leu Phe Asn Thr Ser
                325                 330                 335
Tyr Cys Pro Tyr Ser Gln Cys Ala Phe Asn Gly Ile Phe Leu Pro Pro
            340                 345                 350
Leu Gln Gly Asp Phe Gly Ala Phe Ser Ala Phe Tyr Phe Val Met Lys
        355                 360                 365
Phe Leu Asn Leu Thr Ser Glu Lys Val Ser Gln Glu Lys Val Thr Glu
    370                 375                 380
Met Met Lys Lys Phe Cys Ala Gln Pro Trp Glu Glu Ile Lys Thr Ser
385                 390                 395                 400
Tyr Ala Gly Val Lys Glu Lys Tyr Leu Ser Glu Tyr Cys Phe Ser Gly
                405                 410                 415
Thr Tyr Ile Leu Ser Leu Leu Leu Gln Gly Tyr His Phe Thr Ala Asp
            420                 425                 430
Ser Trp Glu His Ile His Phe Ile Gly Lys Ile Gln Gly Ser Asp Ala
        435                 440                 445
Gly Trp Thr Leu Gly Tyr Met Leu Asn Leu Thr Asn Met Ile Pro Ala
    450                 455                 460
Glu Gln Pro Leu Ser Thr Pro Leu Ser His Ser Thr Tyr Val Asp Tyr
465                 470                 475                 480
Lys Asp Asp Asp Asp Lys
                485
```

COMPOSITIONS AND METHODS FOR TREATING CANCER

CROSS-REFERENCE TO RELATED APPLICATIONS

This application claims the benefit of U.S. Provisional Application Nos. U.S. 62/471,994 filed 16 Mar. 2017 and U.S. 62/586,220 filed 15 Nov. 2017; both of which are incorporated herein by reference in their entireties; including any drawings.

REFERENCE TO SEQUENCE LISTING

The present application is being filed along with a Sequence Listing in electronic format. The Sequence Listing is provided as a file entitled "CD39-6_ST25", created 15 Mar. 2018, which is 53 KB in size. The information in the electronic format of the Sequence Listing is incorporated herein by reference in its entirety.

FIELD OF THE INVENTION

The present invention relates to antigen-binding compounds (e.g., antibodies) that inhibit the enzymatic activity of soluble human CD39. The invention also relates to cells producing such compounds; methods of making such compounds, and antibodies, fragments, variants, and derivatives thereof; pharmaceutical compositions comprising the same; methods of using the compounds to diagnose, treat or prevent diseases, e.g., cancer.

BACKGROUND

Eight different ENTPD genes encode members of the NTPDase protein family. The individual NTPDase subtypes differ in cellular location and functional properties. Plasma membrane-bound nucleoside triphosphate diphosphohydrolases control nucleotide levels at the cell surface by hydrolyzing the c and b phosphates of nucleotides.

NTPDase 1 (ectonucleoside triphosphate diphosphohydrolase1), also known as CD39/ENTPD1 or vascular CD39, functions together with another enzyme, CD73 (ecto-5'-nucleotidase), to hydrolyze extracellular adenosine triphosphate (ATP) and adenosine diphosphate (ADP) to generate adenosine, which binds to adenosine receptors and inhibits T-cell and natural killer (NK)-cell responses, thereby suppressing the immune system. The generation of adenosine via the CD73/CD39 pathway is recognized as a major mechanism of regulatory T cell (Treg) immunosuppressive function. The number of $CD39^+$ Tregs is increased in some human cancers, and the importance of $CD39^+$ Tregs in promoting tumor growth and metastasis has been demonstrated using several in vivo models. However, CD39 is also expressed by tumor cells and $CD39^+$ tumor cells can mediate immunosuppression via the adenosine pathway. CD39 in cancer cells displays ATPase activity and, together with CD73, generates adenosine. $CD73^+CD39^+$ cancer cells inhibited the proliferation of CD4 and CD8 T cells and the generation of cytotoxic effector CD8 T cells (CTL) in a CD39- and adenosine-dependent manner. CD39 has been reported to be increased in several solid tumors (colorectal cancer, head and neck cancer, pancreatic cancer) as well as in chronic lymphocytic leukemia. Antibodies that bind and inhibit CD39 in CD39-expressing cells are disclosed in WO2009/095478. Antibody "A1" (eBiosciences, Inc.) is used for staining applications and does not exhibit the ability to neutralize CD39 activity in cells. Hayes et al. (2015) Am. J. Transl. Res. 7(6):1181-1188 makes use of an anti-CD39 that binds FcγR and has effector function but it is stated to also be blocking. CD39 expression on different cell types, including leukocytes and tumor cells, combined with use of antibodies that either do not actually block CD39 or are not pure blockers, create a complex setting for evaluation of the underlying activity of antibodies. To date, the only reported inhibitor of the CD39 active site remains small molecule non-hydrolysable ATP analogues exemplified by ARL67156, suggesting that direct inhibition of the active site is required. ARL67156 however, is not specific for CD39 and also inhibits other NTPDases such as NTPDase1, NTPDase3, NPP1 or mouse NTPDase8, and furthermore only as a weak competitive inhibitor (Levesque et al. (2007) Br. J. Pharmacol. 152:141-150).

CD39 has two transmembrane domains near the N- and C-terminal ends, short cytoplasmic N- and C-terminal segments, and a large extracellular domain containing the active site. However, while CD39 is typically anchored to the membrane by the two transmembrane domains at the two ends of the molecule, it has recently also been reported that a soluble catalytically active form of CD39 can be found in circulation in human and mice (Yegutkin et al., (2012) FASEB J. 26(9): 3875-3883). Despite various anti-CD39 antibodies described, no antibody has been reported to be able to inhibit the ATPase activity of soluble extracellular CD39 protein.

SUMMARY OF THE INVENTION

The inventors have obtained antibodies that inhibit the enzymatic (ATPase activity) activity of soluble (extracellular domain) human CD39 protein. The antibodies additionally bind an epitope present on human CD39 protein expressed at the surface of cells, including tumor cells and potently inhibit the enzymatic (ATPase activity) activity of the cell membrane bound CD39 enzyme (CD39 as expressed at the surface of cells). The antibodies can be used advantageously to achieve greater neutralization of CD39 activity in an individual by neutralizing both membrane-bound and soluble CD39 protein (an extracellular domain protein in solution), thereby reducing immunosuppression, e.g., for the treatment of cancer and/or infectious disease. While other anti-CD39 antibodies have been previously described that inhibit the enzymatic (ATPase activity) activity of the membrane bound CD39 enzyme, those antibodies do not inhibit soluble CD39 protein which is not bound to the cell membrane.

Accordingly, provided in one embodiment is an antigen binding domain or a protein comprising such, optionally an antibody or antibody fragment, that binds to and inhibits or neutralizes the ATPase activity of a soluble CD39 protein (sCD39). In one embodiment the sCD39 protein lacks the two transmembrane domains (i.e. the transmembrane domains near the N- and C-terminal ends) found in membrane bound CD39. In one embodiment, sCD39 is a non-membrane bound sCD39 protein found in circulation, e.g., in a human individual. In one embodiment, sCD39 comprises or consists of the amino acid sequence of SEQ ID NO: 44 (optionally further comprising a C-terminal tag or another non-CD39-derived amino acid sequence). In one embodiment, the protein, antibody or antibody fragment inhibits the ATPase activity of sCD39 when incubated with sCD39 in solution, e.g., according to the methods or assays conducted in the absence of cells as disclosed herein (see, e.g. Examples, Methods). In one embodiment, the protein, antibody or antibody fragment specifically binds the human CD39 protein, both in soluble (extracellular domain protein) and in membrane-bound form.

Without wishing to be bound by theory, some antibodies may neutralize membrane-bound CD39 by inhibiting the domain motion of membrane-bound CD39 (memCD39), however without similarly affecting the activity of the soluble CD39 protein (sCD39). It has been reported that memCD39 occurs as a homo-multimer while sCD39 is a monomer, and moreover that the transmembrane domains in memCD39 undergo dynamic motions that underlie a functional relationship with the active site. Consequently, unlike sCD39, memCD39 may present a setting that makes antibody-mediated neutralization possible. One possibility is that use of a bivalent antibody that binds simultaneously to two memCD39 molecules (e.g., within a memCD39 homo-multimer) is required for functional neutralization.

The present antibodies that neutralize the activity of sCD39 (and memCD39) may, in addition to use as bivalent binders, also be effective as monovalent binders, whether they are targeting memCD39 in addition to sCD39. Consequently, in one embodiment, provided is an antigen binding protein that binds monovalently to a human CD39 protein (sCD39 and/or memCD39) and neutralizes the enzymatic (ATPase) activity thereof. The antigen binding protein can optionally be specified as binding to a single CD39 protein and/or bearing a single antigen binding domain capable of binding to a CD39 protein. In one embodiment, provided is an antibody fragment, optionally a F(ab) fragment, a single chain antibody, a scFv, a multispecific antibody, that binds monovalently to a human CD39 protein (sCD39 and/or memCD39) and neutralizes the enzymatic (ATPase) activity thereof. In one embodiment, a CD39-neutralizing antigen binding protein that binds monovalently to a human CD39 protein is a multi-specific antigen binding protein, e.g., a multi-specific antibody, a bi-specific antibody, a tri-specific antibody, etc. In one embodiment, a CD39-neutralizing antigen binding protein that binds monovalently to a human CD39 protein comprises a first (or a single) antigen binding domain that binds CD39 (sCD39 and/or memCD39) and a second antigen binding domain that binds a protein other than CD39.

Advantageously, in one embodiment the antibody comprises a human Fc domain that is modified to have decreased or substantially lack binding to a human Fcγ receptor, e.g., one or more (or all of) human CD16, CD32a, CD32b and CD64. In one aspect, the antibodies do not depend on ADCC-, CDC- or toxin-mediated depletion of CD39-expressing cells for their CD39 inhibitory activity. These antibodies can be used as "pure" CD39 blockers, permitting immunomodulatory activity.

In alternative embodiment, the binding molecule can be produced such that it retains and/or mediates effector function via its Fc domain. In one embodiment the antibody comprises a human Fc domain that binds to a human Fcγ receptor, e.g., one or more (or all of) human CD16, CD32a, CD32b and CD64.

In another embodiment, the Fc domain can be modified to reduce Fcγ receptor binding, optionally by retaining binding to one or more human Fcγ receptor(s) but having decreased binding to one or more other human Fcγ receptor(s).

In one aspect, the antibodies specifically bind vascular CD39, e.g., the antibody binds a polypeptide having the sequence of SEQ ID NO: 1 but not does bind a secreted CD39 isoform polypeptide, e.g., a CD39-L2 and/or -L4 polypeptide. Optionally, the anti-CD39 antibody specifically binds vascular CD39, e.g., the antibody binds a polypeptide having the sequence of SEQ ID NO: 1 but not does bind a membrane bound CD39 isoform, e.g., CD39-L1 and/or -L3 polypeptide.

The antibodies of the disclosure can inhibit the enzymatic activity of membrane-bound CD39 protein expressed at the surface of cells.

In one aspect, the antibodies do not depend on CD39 down-modulation for their CD39 inhibitory activity.

The antibodies of the disclosure can in addition to inhibiting soluble CD39 be capable of inhibiting the enzymatic activity of membrane-bound CD39 protein expressed at the surface of cells, with or without induction of CD39 internalization, and with or without binding of CD16 (FcγIII receptor) and/or with or without substantially directing ADCC and/or CDC toward a CD39-expressing cell. Optionally, the antibodies retain an Fc domain and retain binding to human FcRn.

While antibodies that function by inducing ADCC and/or CDC may be efficient even without complete neutralization/inhibition of the ATPase activity of CD39, as long as enough antibody is bound to a CD39-expressing cell to induce ADCC, neutralizing non-depleting antibodies may require stronger inhibition of the enzymatic activity of ATPase. In one embodiment, a non-depleting antibody will provide an at least 50%, 60%, 70%, 80% or 90% reduction in the ATPase activity of a soluble CD39 protein (e.g., as assessed by the methods disclosed herein), optionally further at a concentration compatible with administration of an antibody to a human. In one embodiment, a non-depleting antibody will provide an at least 70%, 80%, 90% reduction in the ATPase activity of a CD39-expressing cell (e.g., as assessed by decrease in AMP generation by a CD39+ cell such as a B cell, a Ramos cell, as measured by the methods disclosed herein), optionally further at a concentration compatible with administration of an antibody to a human.

The epitope on CD39 bound by the antibodies is present on CD39 polypeptides as expressed by a range of cells, e.g., cancer cells, CD4 T cells, CD8 T cells, B cells, transfected cells, and binds with high affinity as determined by flow cytometry.

An antibody can optionally be characterized by an $EC_{50}$, as determined by flow cytometry, of no more than 2 µg/ml, no more than 1 µg/ml, no more than 0.5 µg/ml, no more than 0.1 µg/ml or no more than 0.05 µg/ml, for binding to cells that express at their surface a CD39 polypeptide. In one embodiment the cells are cells that are made to express CD39 at their surface. In one embodiment the cells are cells that endogenously express CD39 at their surface, e.g., regulatory T (TReg) cells, B cells, cancer cells, lymphoma cells (e.g., Ramos cells), leukemia cells, bladder cancer cells, glioma cells, glioblastoma cells, ovarian cancer cells, melanoma cells, prostate cancer cells, thyroid cancer cells, esophageal cancer cells or breast cancer cells.

In one aspect, provided is an anti-CD39 antibody capable of: (a) inhibiting the enzymatic activity of membrane-bound CD39 protein (e.g., comprising an amino acid sequence of SEQ ID NO: 1) expressed at the surface of cells, and (b) inhibiting the enzymatic activity of soluble CD39 protein (e.g., comprising an amino acid sequence of SEQ ID NO: 44). In one embodiment, the antibodies do not substantially bind (e.g., via their Fc domain) to human Fcγ receptors (e.g., CD16, CD32a, CD32b, CD64) and/or C1q, and/or do not substantially directing ADCC and/or CDC toward a CD39-expressing cell. Optionally, the antibodies retain an Fc domain and retain binding to human FcRn.

In one embodiment, the antibodies are administered in an amount effective to neutralize the enzymatic activity of sCD39 and/or memCD39 for a desired period of time, e.g., 1 week, 2 weeks, a month, until the next successive administration of anti-CD39 antibody.

In one embodiment, the antibodies are administered at a dosage and/or frequency that provides a blood concentration of antibody equal to at least the $EC_{50}$, $EC_{70}$ or $EC_{100}$ for inhibition of ATPase activity of sCD39 protein, optionally wherein the concentration is maintained for at least 1 week, 2 weeks, a month, or until the next successive administration of the anti-CD39 antibody.

In one aspect, the antibody binds an epitope on CD39 comprising an amino acid residue (e.g., one, two or three of the residues) selected from the group consisting of R138, M139 and E142 (with reference to SEQ ID NO: 1).

In one aspect, an anti-CD39 antibody exhibits reduced binding (e.g. substantially complete loss of binding) to a CD39 polypeptide having a mutation at one, two or three of the residues selected from the group consisting of: R138, M139 and E142 (with reference to SEQ ID NO: 1), compared to a wild-type CD39 polypeptide (a CD39 polypeptide of SEQ ID NO: 1); optionally, the mutant CD39 polypeptide has the mutations: R138A, M139A and E142K. In one optional aspect, the antibody does not have a loss of binding to any of the mutant CD39 polypeptide of Table 1 other than mutant 19. In another optional aspect, the anti-CD39 antibody exhibits reduced binding (optionally reduced but not a substantially complete loss of binding; or optionally a substantially complete loss of binding) to a CD39 polypeptide having a mutation at one, two, three or four of the residues selected from the group consisting of: Q96, N99, E143 and R147 (with reference to SEQ ID NO: 1), compared to a wild-type CD39 polypeptide (a CD39 polypeptide of SEQ ID NO: 1); optionally, the mutant CD39 polypeptide has the mutations: Q96A, N99A, E143A and R147E.

In one aspect, the antibody binds an epitope on CD39 comprising an amino acid residue (e.g., one, two, three or four of the residues) selected from the group consisting of Q96, N99, E143 and R147 (with reference to SEQ ID NO: 1). In one aspect, the antibody has reduced binding (e.g. substantially complete loss of binding) to a mutant CD39 polypeptide comprising a mutation at 1, 2, 3 or 4 residues selected from the group consisting of Q96, N99, E143 and R147 (with reference to SEQ ID NO: 1), in each case relative to binding between the antibody and a wild-type CD39 polypeptide comprising the amino acid sequence of SEQ ID NO: 1

In one aspect, the antibody binds an epitope on CD39 comprising (a) an amino acid residue (e.g., one, two or three of the residues) selected from the group consisting of R138, M139 and E142 (with reference to SEQ ID NO: 1), and (b) an amino acid residue (e.g., one, two, three or four of the residues) selected from the group consisting of Q96, N99, E143 and R147.

In one aspect, an anti-CD39 antibody exhibits reduced (e.g. substantially complete loss of) binding to both (a) a CD39 polypeptide having a mutation at one, two, three or four of the residues selected from the group consisting of: Q96, N99, E143 and R147 (with reference to SEQ ID NO: 1), and (b) a CD39 polypeptide having a mutation at one, two, or three of the residues selected from the group consisting of: R138, M139 and E142 (with reference to SEQ ID NO: 1), in each case compared to a wild-type CD39 polypeptide (a CD39 polypeptide of SEQ ID NO: 1). Optionally, the mutant CD39 polypeptide of (a) has the mutations: Q96A, N99A, E143A and R147E. Optionally, the mutant CD39 polypeptide of (b) has the mutations: R138A, M139A and E142K. Optionally the antibody does not have a loss of binding to any of the mutant CD39 polypeptide of Table 1 other than mutants 5 and 19.

In one aspect, the antibody binds an epitope on CD39 comprising an amino acid residue (e.g., one, two, three or four of the residues) selected from the group consisting of K87, E100 and D107 (with reference to SEQ ID NO: 1).

In one aspect, an anti-CD39 antibody exhibits reduced binding (e.g. substantially complete loss of binding) to a CD39 polypeptide having a mutation at one, two, three or four of the residues selected from the group consisting of: K87, E100 and D107 (with reference to SEQ ID NO: 1), compared to a wild-type CD39 polypeptide (a CD39 polypeptide of SEQ ID NO: 1); optionally, the mutant CD39 polypeptide has the mutations: K87A, E100A and D107A. Optionally the antibody does not have a loss of binding to any of the mutant CD39 polypeptide of Table 1 other than mutant 15.

In one aspect, the antibody binds an epitope on CD39 comprising an amino acid residue (e.g., one, two, three or four of the residues) selected from the group consisting of N371, L372, E375, K376 and V377 (with reference to SEQ ID NO: 1).

In one aspect, an anti-CD39 antibody exhibits reduced (e.g. substantially complete loss of) binding to a CD39 polypeptide having a mutation at one, two, three, four or five of the residues selected from the group consisting of: N371, L372, E375, K376 and V377 (with reference to SEQ ID NO: 1), compared to a wild-type CD39 polypeptide (a CD39 polypeptide of SEQ ID NO: 1); optionally, the mutant CD39 polypeptide has the mutations: N371K, L372K, E375A, K376G and V377S, and an insertion of a valine between residues 376 and 377. Optionally the antibody does not have a loss of binding to any of the mutant CD39 polypeptide of Table 1 other than mutant 11.

In one embodiment, the CD39 neutralizing antibodies can be characterized by being capable, in purified form, of causing a decrease in the ATPase activity of sCD39 protein in a cell-free assay, optionally causing a decrease of AMP generation by sCD39, by at least 70%, 80% or 90%; optionally causing an increase in ATP present (compared to a negative control), e.g., as assessed in the assays disclosed herein. For example sCD39 inhibition can be assessed by quantifying luminescence units which are proportional to the amount of ATP present following incubation with anti-CD39 antibody. In one embodiment, the CD39-neutralizing antibodies can be characterized by an $EC_{50}$ for inhibition of ATPase activity of sCD39 protein of no more than 1 µg/ml, optionally no more than 0.5 µg/ml, optionally no more than 0.1 µg/ml.

Optionally, inhibition of ATPase activity of sCD39 protein is determined by quantifying using the Cell Titer Glo™ (Promega), in a cell-free version of the assay in which dose ranges of test antibody are incubated with soluble recombinant human CD39 protein described in Examples, Methods, for 1 hour at 37° C., where 20 µM ATP is added to the plates for 30 additional minutes at 37° C. before addition of Cell Titer Glo™ (CTG) reagent, and emitted light is quantified using an Enspire™ luminometer after incubation for 5 minutes in the dark (see, e.g., Examples, Methods).

Optionally, the CD39 neutralizing antibodies can further be characterized by being capable, in purified form, of causing a decrease in cells' ATPase activity of CD39, optionally causing a decrease of AMP generation by a CD39-expressing cell, by at least 70%, 80% or 90%. In one embodiment, the CD39-neutralizing antibodies can be characterized by an $EC_{50}$ for inhibition of ATPase activity (e.g., $EC_{50}$ for inhibition of AMP generation by a CD39-expressing cell) of CD39 expressed by a cell of no more than 1 μg/ml, optionally no more than 0.5 μg/ml, optionally no more than 0.1 μg/ml.

Optionally, inhibition of ATPase activity of CD39 expressed by a cell is determined by assessing neutralization of ATPase activity in Ramos cells by quantifying AMP generated by hydrolysis of ATP (see, e.g., Examples, Methods).

In one aspect, neutralization of the ATPase activity by a CD39-expressing cell is determined by bringing CD39-expressing cells (e.g., Ramos lymphoma cells as used herein, available for example from the ATCC, reference CRL-1596) into contact with an antibody, and assessing production of AMP, e.g., by mass spectrometry, wherein a decrease in AMP generated indicates neutralization of ATPase activity. Optionally an antibody causes a decrease of AMP generated by at least 70%, 80% or 90% in this assay. Optionally an antibody causes a decrease of extracellular ATPase activity by a B cell of at least 70%, 80% or 90%.

In one aspect, provided is a neutralizing anti-CD39 antibody that binds an antigenic determinant present on both sCD39 and CD39 expressed at the cell surface (memCD39).

Provided in one aspect provided is a neutralizing anti-CD39 antibody that competes for binding to an epitope on CD39 bound by antibody I-394, (e.g., that competes for binding to an epitope on a CD39 polypeptide with an antibody having the heavy and light chain CDRs or variable regions of any of I-394).

In one aspect of any of the embodiments herein, provided is an antigen-binding compound that binds the same epitope and/or competes for binding to a CD39 polypeptide with monoclonal antibody I-394 (e.g., that binds the same epitope and/or competes for binding to a CD39 polypeptide with an antibody having the heavy and light chain CDRs or variable regions of I-394). In one embodiment, provided is antigen-binding compound binds the same epitope and/or competes for binding to a CD39 polypeptide with an antibody having respectively a VH and VL region of SEQ ID NOS: 6 and 7.

In one embodiment, an anti-CD39 antibody binds an epitope comprising one, two or three amino acid residues selected from the group consisting of the amino acid residues on CD39 bound by I-394.

In one aspect of any of the embodiments herein, provided is an antigen-binding compound (e.g. an antibody or antibody fragment) that binds the same epitope and/or competes for binding to a CD39 polypeptide with monoclonal antibody I-395 (e.g., that binds the same epitope and/or competes for binding to a CD39 polypeptide with an antibody having the heavy and light chain CDRs or variable regions of I-395). In one aspect of any of the embodiments herein, provided is an antigen-binding compound that binds the same epitope and/or competes for binding to a CD39 polypeptide with monoclonal antibody I-396 (e.g., that binds the same epitope and/or competes for binding to a CD39 polypeptide with an antibody having the heavy and light chain CDRs or variable regions of I-396). In one aspect of any of the embodiments herein, provided is an antigen-binding compound that binds the same epitope and/or competes for binding to a CD39 polypeptide with monoclonal antibody I-397 (e.g., that binds the same epitope and/or competes for binding to a CD39 polypeptide with an antibody having the heavy and light chain CDRs or variable regions of I-397). In one aspect of any of the embodiments herein, provided is an antigen-binding compound that binds the same epitope and/or competes for binding to a CD39 polypeptide with monoclonal antibody I-398 (e.g., that binds the same epitope and/or competes for binding to a CD39 polypeptide with an antibody having the heavy and light chain CDRs or variable regions of I-398). In one aspect of any of the embodiments herein, provided is an antigen-binding compound that binds the same epitope and/or competes for binding to a CD39 polypeptide with monoclonal antibody I-399 (e.g., that binds the same epitope and/or competes for binding to a CD39 polypeptide with an antibody having the heavy and light chain CDRs or variable regions of I-399).

In one embodiment, the binding molecule (e.g., antibody or antibody fragment) comprises the variable heavy chain domain ($V_H$) comprising a heavy chain CDR1, 2 and 3 (e.g., as described herein) for antibody I-394, I-395, I-396, I-397, I-398 or I-399, and a variable light chain domain ($V_L$) comprising a light chain CDR1, 2 and 3 (e.g., as described herein) for the respective I-394, I-395, I-396, I-397, I-398 or I-399 antibody, or an amino acid sequence in which the CDR (or set of heavy and/or light chain CDRs) has at least 70%, 80%, 90% or 95% amino acid identity to said CDR (or said set of heavy and/or light chain CDRs). In one aspect of any of the embodiments herein, the antibody may comprise a heavy chain comprising the three CDRs of the heavy chain variable region (VH) of antibody I-394, I-395, I-396, I-397, I-398 or I-399 and a light chain comprising the three CDRs of the light chain variable region (VL) of the respective I-394, I-395, I-396, I-397, I-398 or I-399 antibody, optionally wherein CDRs are determined according to Kabat, Chothia or IMGT numbering schemes.

In one aspect, provided is an antibody comprising an Fc domain that is modified (compared to a wild-type Fc domain of the same isotype) to reduce binding between the Fc domain and human CD16A, CD16B, CD32A, CD32B and/or CD64 polypeptides, wherein the antibody comprises: (i) a heavy chain comprising CDR 1, 2 and 3 of the heavy chain variable region of SEQ ID NO: 6 and (ii) a light chain comprising CDR 1, 2 and 3 of the light chain variable region of SEQ ID NO: 7. In one aspect, the Fc domain is modified (compared to a wild-type Fc domain of the same isotype) to reduce binding between the Fc domain and human C1q polypeptide. In one embodiment, the antibody comprises an amino acid substitution in a heavy chain constant region at any one, two, three, four, five or more of residues selected from the group consisting of: 220, 226, 229, 233, 234, 235, 236, 237, 238, 243, 264, 268, 297, 298, 299, 309, 310, 318, 320, 322, 327, 330 and 331 (Kabat EU numbering). In one embodiment, the antibody has an amino acid substitution in a heavy chain constant region at any three, four, five or more of residues selected from the group consisting of: 234, 235, 237, 322, 330 and 331.

In one embodiment, the antibodies are administered to an individual having a cancer in an amount and frequency sufficient to neutralize the activity of sCD39 in the tumor microenvironment and/or in circulation. In one embodiment, the antibodies are administered in an amount and frequency sufficient to decrease the generation and/or concentration of adenosine in the tumor microenvironment. In one embodiment, the antibodies are administered in an amount and frequency sufficient to decrease the generation and/or concentration of AMP and/or adenosine in the tumor microenvironment. In one embodiment, the antibodies are administered in an amount and frequency sufficient to neutralize the activity of CD39 expressed by tumor cells. In one embodiment, the antibodies are administered in an amount and frequency sufficient to neutralize the activity of CD39 expressed by leukocytes or lymphocytes, e.g., CD4 T cells, CD8 T cells, TReg cells and/or B cells.

The antibodies will be useful in inhibiting CD39-mediated ATP hydrolysis, e.g., thereby leading to a decrease in the concentration of adenosine in the tumor microenvironment and/or in circulation. These antibodies will therefore be useful in reversing the immunosuppressive effect of CD39 and/or adenosine on T cells, B cells and other cells that express adenosine receptors (A2A receptors), for example in the treatment of cancer. In one embodiment, the anti-CD39 antibody neutralizes adenosine-mediated inhibition of proliferation, cytokine production, cytotoxicity and/or NFκB activity in T cells.

The antibodies will be useful in inhibiting the production, amounts and/or concentrations of adenosine into the tumor microenvironment and/or in circulation.

In another aspect provided is a method for treating an individual, the method comprising administering to an individual (e.g., an individual having a disease, a tumor, etc.) a therapeutically active amount of any of the anti-CD39 antigen binding compounds described herein. In one aspect provided is a method for treating an individual, the method comprising, consisting essentially of or consisting of: administering to an individual (e.g., an individual having a disease, a tumor, etc.) a therapeutically active amount of an antigen binding compound of the disclosure that inhibits a CD39 polypeptide. In one embodiment, the anti-CD39 antigen binding compound (e.g., antibody) is administered to an individual in combination with a second therapeutic agent, optionally a therapeutic agent (e.g., antibody) that neutralizes the inhibitory activity of human PD-1, optionally an anti-PD-1 antibody, optionally an anti-PD-L1 antibody. In one embodiment, the anti-CD39 antigen binding compound (e.g., antibody) is administered to an individual having a cancer and who has a poor response, or prognostic for response, to treatment with an agent that neutralizes the inhibitory activity of human PD-1. In one embodiment, the antibody inhibits a CD39 polypeptide in a cellular assay. The compound is in one embodiment a non-depleting antibody (an antibody that does not deplete cells to which it binds, e.g., an Fc silent antibody). Optionally, the compound binds to CD39 polypeptides in bivalent manner. Optionally, the antibody is a chimeric, humanized or human antibody. Optionally, the antibody comprises a heavy chain constant region of IgG (e.g., IgG1) isotype modified to eliminate binding to human Fcγ receptors (e.g., CD16A, CD16B, CD32A, CD32B and/or CD64).

In another aspect, antibodies having increased stability and/or solubility in conventional pharmaceutical formulations can advantageously be combined in pharmaceutical formulations with other antibodies. Provided in one embodiment is a pharmaceutical formulation comprising (i) an antibody that inhibits a CD39 polypeptide and displays increased stability, e.g., an antibody that inhibits a CD39 polypeptide comprising a plurality of aromatic resides in a CDR and a modified human IgG1 Fc domain comprising an amino acid substitution at any three, four, five or more of residues at Kabat positions 234, 235, 237, 322, 330 and 331, and (ii) a second antibody of human IgG isotype, optionally wherein the second antibody has anti-cancer activity. In one embodiment, the second antibody is capable of inducing ADCC toward a cell to which it is bound, optionally the second antibody binds to an antigen present on a tumor cell (a tumor antigen). In one embodiment, the second antibody is capable of a neutralizing the activity of a protein to which its hypervariable region binds. Provided in one embodiment is a pharmaceutical formulation comprising (i) an antibody that inhibits a CD39 polypeptide and displays increased stability, e.g., an antibody that inhibits a CD39 polypeptide comprising a plurality of aromatic resides in a CDR and a modified human IgG1 Fc domain comprising an amino acid substitution at any three, four, five or more of residues at Kabat positions 234, 235, 237, 322, 330 and 331, and (ii) a second antibody of human IgG isotype, wherein the second antibody neutralizes the inhibitory activity of human PD-1, optionally an anti-PD-1 antibody, optionally an anti-PD-L1 antibody. In one embodiment, both the anti-CD39 antibody and the second antibody comprise a modified human IgG1 Fc domain comprising an amino acid substitution at any three, four, five or more of residues at Kabat positions 234, 235, 237, 322, 330 and 331.

In one aspect provided is a method for decreasing ATP hydrolysis by a CD39-expressing cell (e.g., a leukocyte and/or a tumor cell in an individual), or a method for neutralizing of the enzymatic activity of cellular CD39, the method comprising: bringing the CD39-expressing cell into contact with an antibody of the disclosure that inhibits CD39. In one embodiment, the step of bringing the CD39-expressing cell into contact with an antigen binding compound of the disclosure comprises administering to an individual a therapeutically active amount of an antibody that inhibits CD39. In one embodiment the individual has a cancer.

In one aspect provided is a method for decreasing adenosine present in the tumor environment (e.g., in an individual), the method comprising, consisting essentially of or consisting of: administering to an individual a therapeutically active amount of an antibody of the disclosure that inhibits a CD39 polypeptide. In one embodiment the individual has a cancer.

In one embodiment, the active amount of an antibody that inhibits a CD39 polypeptide is an amount effective to achieve and/or maintain (e.g., until the subsequent administration of antigen binding compound) a blood concentration of at least the $EC_{50}$, optionally the $EC_{70}$, optionally substantially the $EC_{100}$, for inhibition of CD39-mediated catabolism of ATP to AMP in an individual. In one embodiment, the active amount of an antigen binding compound that inhibits a CD39 polypeptide is an amount effective to achieve the $EC_{50}$, optionally the $EC_{70}$, optionally substantially the $EC_{100}$, for inhibition of CD39-mediated catabolism of ATP to AMP in an extravascular tissue of an individual. In one embodiment, the active amount an antigen binding compound that inhibits a CD39 polypeptide is an amount effective to achieve the $EC_{50}$, optionally the $EC_{70}$, optionally substantially the $EC_{100}$, for inhibition of CD39-mediated catabolism of ATP to AMP in an individual. In one embodiment, the active amount of an antigen binding compound that inhibits a CD39 polypeptide is between 1 and 20 mg/kg body weight. In one embodiment, the active amount is administered to an individual weekly, every two weeks, monthly or every two months.

Optionally the individual is a human having or who is susceptible to having a cancer. Optionally the individual is a human having or who is susceptible to having a cancer characterized by malignant cells that express CD39 and/or presence (secretion or shedding) or soluble CD39 protein. Optionally the individual is a human having or who is susceptible to having a cancer and who has detectable levels of circulating soluble extracellular CD39 protein or tumor-infiltrating leukocytes that express CD39.

The antibodies are optionally characterized by binding affinity ($K_D$) for a human CD39 polypeptide of less than (better than) $10^{-9}$ M, preferably less than $10^{-10}$ M, or preferably less than $10^{-11}$M, and/or by binding human CD39 with an $EC_{50}$ lower than (better binding than) 1 µg/ml, preferably wherein the antibody has an $EC_{50}$ of no more than 0.5 µg/ml, optionally no more than 0.2 µg/ml, optionally no more than 0.1 µg/ml, for binding to cells (e.g., tumor cells) expressing human CD39 at the cell surface.

The antibodies are optionally chimeric, human or humanized antibodies.

The antibodies are optionally characterized by an $EC_{50}$ for neutralization of the enzymatic activity of CD39 in CD39-expressing cells (e.g., Ramos tumor cells) of less than (better than) 1 µg/ml, optionally less than 0.5 µg/ml.

In one embodiment, the antibody is a monoclonal antibody or a fragment thereof that retains binding specificity and ability to neutralize the enzymatic activity of CD39. In one embodiment, the antibody is an IgG1 antibody. For example, the antibody may be an antibody comprising an Fc domain of human IgG1 isotype modified to reduce binding between the Fc domain and an Fcγ receptor (e.g., CD16). In one embodiment, the antigen-binding compound lacks an Fc domain or comprises an Fc domain that does not induce antibody mediated cellular cytotoxicity (ADCC) and/or CDC; optionally the antigen-binding compound comprises an Fc domain that does not bind to a FcγRIIIA (CD16) polypeptide. In one embodiment, the Fc domain (e.g., of human IgG1, IgG2, IgG3 or IgG4 isotype) comprises an amino acid modification (e.g., substitution) compared to a wild-type Fc domain, wherein the substitution reduces the ability of the Fc domain (or antibodies containing it) to bind to an Fcγ receptor (e.g., CD16) and/or to bind complement. In one embodiment, the antigen-binding compound is not linked to a toxic moiety.

Also provided are nucleic acids encoding the human or humanized antibody or antibody fragment having any of the foregoing properties, a vector comprising such a nucleic acid, a cell comprising such a vector, and a method of producing a human anti-CD39 antibody, comprising culturing such a cell under conditions suitable for expression of the anti-CD39 antibody. The disclosure also relates to compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers). The disclosure further relates various new and useful methods making and using such antibodies, nucleic acids, vectors, cells, organisms, and/or compositions, such as in the modulation of CD39-mediated biological activities, for example in the treatment of diseases related thereto, notably cancers.

The disclosure also provides a method of potentiating the activity of lymphocytes (e.g., T cells) in a subject in need thereof, or for restoring the activity of lymphocytes (e.g., T cells), or a method of relieving the adenosine-mediated inhibition of lymphocytes (e.g., T cells), which method comprises administering to the subject an effective amount of any of the foregoing compositions. In one embodiment, the subject is a patient suffering from cancer. For example, the patient may be suffering from a solid tumor, e.g., colorectal cancer, renal cancer, ovarian cancer, lung cancer, breast cancer or malignant melanoma. Alternatively, the patient may be suffering from a hematopoietic cancer, e.g., acute myeloid leukaemia, chronic myeloid leukaemia, multiple myeloma, or non-Hodgkin's lymphoma.

The disclosure also provides a method for treatment of disease in an individual, the treatment comprising administering to the individual an anti-CD39 antibody that neutralizes the enzymatic activity of CD39 for at least one administration cycle in which the anti-CD39 antibody is administered at least once, optionally at least twice, in an amount effective to achieve, and/or to maintain between two successive administrations of the anti-CD39 antibody, a concentration in blood (serum) or an extravascular tissue (e.g., tumor environment) that corresponds to at least the $EC_{50}$ (e.g., an $EC_{50}$ between 0.01 and 0.5 µg/ml), optionally the $EC_{70}$ or optionally the $EC_{100}$, for neutralization of the enzymatic activity of CD39 (e.g., an $EC_{100}$ between 0.05 and 1 µg/ml, between 0.1 and 1 µg/ml). The antibody can for example be administered in an amount to achieve and/or maintained a concentration in circulation or in an extravascular tissue (e.g., tumor environment) of at least about 0.1 µg/ml, 0.5 µg/ml, 1 µg/ml or 2 µg/ml). For example, to achieve a concentration in an extravascular tissue of between 0.05 and 1 µg/ml, or between 0.1 and 1 µg/ml, the anti-CD39 antibody is administered in amounts effective to achieve a concentration in circulation of the anti-CD39 antibody of between 0.5 and 10 µg/ml, or between 1 and 10 µg/ml. Optionally, the anti-CD39 antibody is administered at least twice and in amounts effective to maintain the concentration of the anti-CD39 antibody at least the aforementioned concentration for at least 1 week, 2 weeks, 3 weeks, 4 weeks, between two successive administrations of the anti-CD39 antibody and/or throughout the administration cycle.

The disclosure also provides a method for treatment of disease in an individual, the treatment comprising administering to the individual an anti-CD39 antibody that neutralizes the enzymatic activity of CD39 for at least one administration cycle in which the anti-CD39 antibody is administered at least once, optionally at least twice, in an amount effective to achieve, and/or to maintain between two successive administrations of the anti-CD39 antibody, a blood or tissue concentration of anti-CD39 antibody of at least 1 µg/ml, optionally at least 10 µg/ml, optionally between 1 and 100 µg/ml. Optionally, the anti-CD39 antibody is administered at least twice and in amounts effective to maintain a continuous blood or tissue concentration of the anti-CD39 antibody of at least 1 µg/ml, optionally at least 10 µg/ml, optionally between 1 and 100 µg/ml, for at least 1 week, 2 weeks, 3 weeks, 4 weeks, between two successive administrations of the anti-CD39 antibody and/or throughout the administration cycle.

These aspects are more fully described in, and additional aspects, features, and advantages will be apparent from, the description provided herein.

BRIEF DESCRIPTION OF THE DRAWINGS

FIG. 3A shows the position of residues mutated in mutants 5 (M5), 15 (M15) and 19 (M19) on the surface of the CD39 protein. FIG. 3B shows results of binding to mutants 5, 15 and 19 for different antibodies.

FIGS. 4A-D show binding of antibody 1-394 to cells expressing human CD39, as assessed by flow cytometry. 1-394 binds cells expressing human CD39 (CHO-huCD39), cells expressing cynomolgus CD39 (CHO-cyCD39) and to Ramos lymphoma cells, but not to cells expressing murine CD39 (CHO-moCD39).

FIGS. 5A-D show antibody 1-394 is highly potent at blocking CD39 enzymatic activity in tumor (Ramos) cells, in cells expressing human CD39 (CHO-huCD39), and in cells expressing cynomolgus CD39 (CHO-cyCD39), as assessed by quantifying luminescence units which are proportional to the amount of ATP present.

FIGS. 7A-E show antibody 1-394 binds to human CD39 but not to any of the human isoforms CD39-L1, -L2, -L3 or -L4, as assessed in an ELISA assay.

FIGS. 9A and 9B show HLA-DR expression on moDC and FIGS. 10A-D show CD83 expression on moDC. These figures show that the anti-CD39 blocking antibody 1-394 and chemical inhibitors of CD39 lead to moDC activation at each of 0.125 mM, 0.25 mM or 0.5 mM. However, anti-CD39 antibody BY40 or anti-CD73 antibodies were not able to favor ATP-induced activation of dendritic cell (DC), suggesting that antibodies are not able to block enzymatic activity sufficiently to avoid ATP catabolism. The legends, top to bottom, correspond to the bars in the graph, from left to right.

DETAILED DESCRIPTION OF THE INVENTION

Definitions

Figure 1:
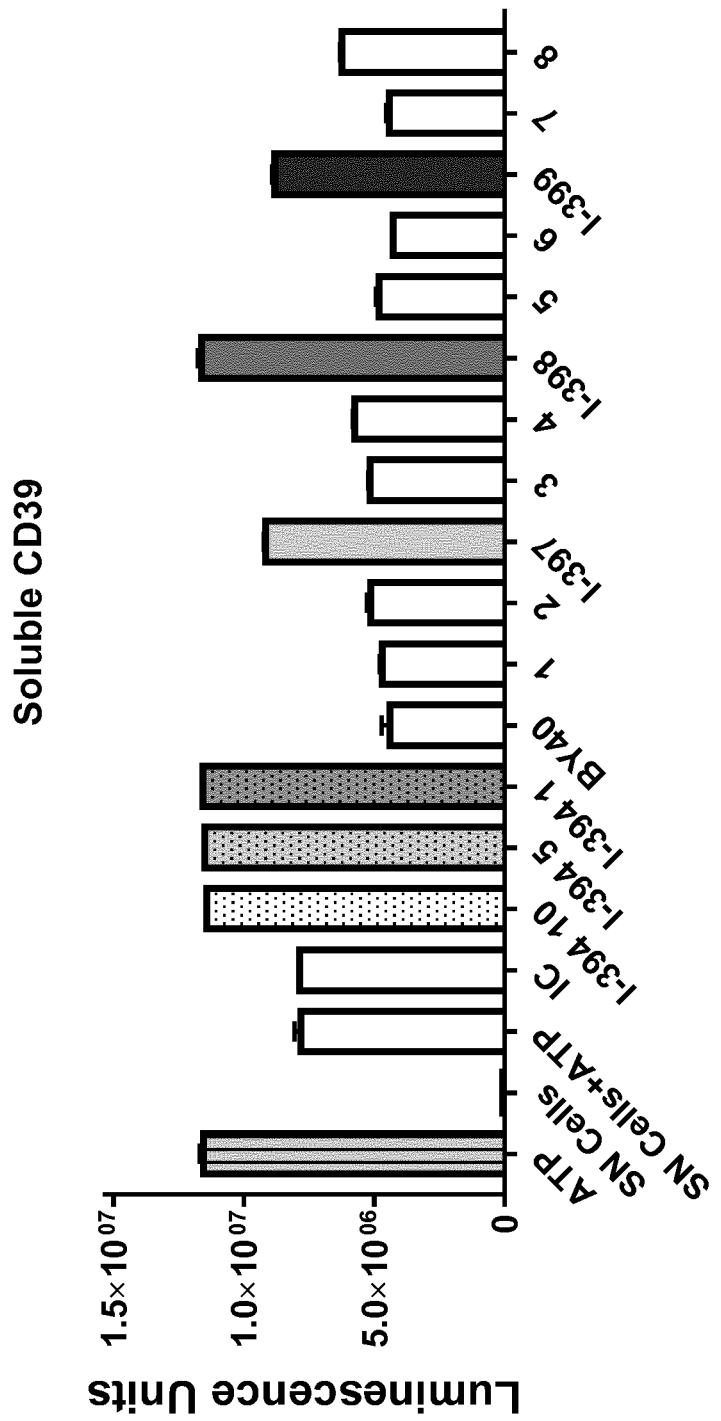
FIG. 1 shows a representative screening result, showing antibodies I-397, I-398 and I-399 compared to positive control I-394 antibody.

Where "comprising" is used, this can optionally be replaced by "consisting essentially of" or by "consisting of".

Human CD39, also known as "vascular" CD39, NTPdase1, ENTPD1, ATPDase and vascular ATP diphosphohydrolase, exhibits ATPase activity. CD39 hydrolyzes extracellular ATP and ADP to AMP, which is further converted to adenosine by another enzyme, 5-prime nucleotidase. The amino acid sequence of the "vascular" human CD39 mature polypeptide chain is shown in Genbank under accession number P49961, the entire disclosure of which is incorporated herein by reference, and as follows:

(SEQ ID NO: 1)

```
  1 MEDTKESNVK TFCSKNILAI LGFSSIIAVI ALLAVGLTQN KALPENVKYG IVLDAGSSHT
 61 SLYIYKWPAE KENDTGVVHQ VEECRVKGPG ISKFVQKVNE IGIYLTDCME RAREVIPRSQ
121 HQETPVYLGA TAGMRLLRME SEELADRVLD VVERSLSNYP FDFQGARIIT GQEEGAYGWI
181 TINYLLGKFS QKTRWFSIVP YETNNQETFG ALDLGGASTQ VTFVPQNQTI ESPDNALQFR
241 LYGKDYNVYT HSFLCYGKDQ ALWQKLAKDI QVASNEILRD PCFHPGYKKV VNVSDLYKTP
301 CTKRFEMTLP FQQFEIQGIG NYQQCHQSIL ELFNTSYCPY SQCAFNGIFL PPLQGDFGAF
361 SAFYFVMKFL NLTSEKVSQE KVTEMMKKFC AQPWEEIKTS YAGVKEKYLS EYCFSGTYIL
421 SLLLQGYHFT ADSWEHIHFI GKIQGSDAGW TLGYMLNLTN MIPAEQPLST PLSHSTYVFL
481 MVLFSLVLFT VAIIGLLIFH KPSYFWKDMV
 45
```

Human CD39-L1, also known as NTPDase2 or ENTPD2, is shown in Genbank under accession number NP_001237, the entire disclosure of which is incorporated herein by reference, and as follows:

(SEQ ID NO: 2)

```
  1 MAGKVRSLLP PLLLAAAGLA GLLLLCVPTR DVREPPALKY GIVLDAGSSH TSMFIYKWPA
 61 DKENDTGIVG QHSSCDVPGG GISSYADNPS GASQSLVGCL EQALQDVPKE RHAGTPLYLG
121 ATAGMRLLNL TNPEASTSVL MAVTHTLTQY PFDFRGARIL SGQEEGVFGW VTANYLLENF
181 IKYGWVGRWF RPRKGTLGAM DLGGASTQIT FETTSPAEDR ASEVQLHLYG QHYRVYTHSF
241 LCYGRDQVLQ RLLASALQTH GFHPCWPRGF STQVLLGDVY QSPCTMAQRP QNFNSSARVS
301 LSGSSDPHLC RDLVSGLFSF SSCPFSRCSF NGVFQPPVAG NFVAFSAFFY TVDFLRTSMG
361 LPVATLQQLE AAAVNVCNQT WAQQLLSRGY GFDERAFGGV IFQKKAADTA VGWALGYMLN
421 LTNLIPADPP GLRKGTDFSS WVVLLLLFAS ALLAALVLLL RQVHSAKLPS TI
```

Human CD39-L2, also known as NTPDase6 or ENTPD6; ENTPD6 isoform 1 is shown in Genbank under accession number NP_001238, the entire disclosure of which is incorporated herein by reference, and as follows:

```
                                                            (SEQ ID NO: 3)
  1 MKKGIRYETS RKTSYIFQQP QHGPWQTRMR KISNHGSLRV AKVAYPLGLC VGVFIYVAYI

61 KWHRATATQA FFSITRAAPG ARWGQQAHSP LGTAADGHEV FYGIMFDAGS TGTRVHVFQF

121 TRPPRETPTL THETFKALKP GLSAYADDVE KSAQGIRELL DVAKQDIPFD FWKATPLVLK

181 ATAGLRLLPG EKAQKLLQKV KEVFKASPFL VGDDCVSIMN GTDEGVSAWI TINFLTGSLK

241 TPGGSSVGML DLGGGSTQIA FLPRVEGTLQ ASPPGYLTAL RMFNRTYKLY SYSYLGLGLM

301 SARLAILGGV EGQPAKDGKE LVSPCLSPSF KGEWEHAEVT YRVSGQKAAA SLHELCAARV

361 SEVLQNRVHR TEEVKHVDFY AFSYYYDLAA GVGLIDAEKG GSLVVGDFEI AAKYVCRTLE

421 TQPQSSPFSC MDLTYVSLLL QEFGFPRSKV LKLTRKIDNV ETSWALGAIF HYIDSLNRQK

481 SPAS
```

Human CD39-L3, also known as NTPDase3 or ENTPD3; ENTPD3 isoform is shown in Genbank under accession number NP_001239, the entire disclosure of which is incorporated herein by reference, and as follows:

```
                                                            (SEQ ID NO: 4)
  1 MFTVLTRQPC EQAGLKALYR TPTIIALVVL LVSIVVLVSI TVIQIHKQEV LPPGLKYGIV

61 LDAGSSRTTV YVYQWPAEKE NNTGVVSQTF KCSVKGSGIS SYGNNPQDVP RAFEECMQKV

121 KGQVPSHLHG STPIHLGATA GMRLLRLQNE TAANEVLESI QSYFKSQPFD FRGAQIISGQ

181 EEGVYGWITA NYLMGNFLEK NLWHMWVHPH GVETTGALDL GGASTQISFV AGEKMDLNTS

241 DIMQVSLYGY VYTLYTHSFQ CYGRNEAEKK FLAMLLQNSP TKNHLTNPCY PRDYSISFTM

301 GHVFDSLCTV DQRPESYNPN DVITFEGTGD PSLCKEKVAS IFDFKACHDQ ETCSFDGVYQ

361 PKIKGPFVAF AGFYYTASAL NLSGSFSLDT FNSSTWNFCS QNWSQLPLLL PKFDEVYARS

421 YCFSANYIYH LFVNGYKFTE ETWPQIHFEK EVGNSSIAWS LGYMLSLTNQ IPAESPLIRL

481 PIEPPVFVGT LAFFTAAALL CLAFLAYLCS ATRRKRHSEH AFDHAVDSD
```

Human CD39-L4, also known as NTPDase5 or ENTPD5, is shown in Genbank under accession number NP_001240 (precursor), the entire disclosure of which is incorporated herein by reference, and as follows:

```
                                                            (SEQ ID NO: 5)
  1 MATSWGTVFF MLVVSCVCSA VSHRNQQTWF EGIFLSSMCP INVSASTLYG IMFDAGSTGT

61 RIHVYTFVQK MPGQLPILEG EVFDSVKPGL SAFVDQPKQG AETVQGLLEV AKDSIPRSHW

121 KKTPVVLKAT AGLRLLPEHK AKALLFEVKE IFRKSPFLVP KGSVSIMDGS DEGILAWVTV

181 NFLTGQLHGH RQETVGTLDL GGASTQITFL PQFEKTLEQT PRGYLTSFEM FNSTYKLYTH

241 SYLGFGLKAA RLATLGALET EGTDGHTFRS ACLPRWLEAE WIFGGVKYQY GGNQEGEVGF

301 EPCYAEVLRV VRGKLHQPEE VQRGSFYAFS YYYDRAVDTD MIDYEKGGIL KVEDFERKAR

361 EVCDNLENFT SGSPFLCMDL SYITALLKDG FGFADSTVLQ LTKKVNNIET GWALGATFHL

421 LQSLGISH
```

In the context herein, "neutralize" or neutralizing" when referring to the CD39 polypeptide (e.g., "neutralize CD39", "neutralize the activity of CD39" or "neutralize the enzymatic activity of CD39"), refers to a process in which the ATP hydrolysis (ATPase) activity of CD39 is inhibited. This comprises, notably the inhibition of CD39-mediated generation of AMP and/or ADP, i.e. the inhibition of CD39-mediated catabolism of ATP to AMP and/or ADP. For membrane-bound CD39, this can be measured for example in a cellular assay that measures the capacity of a test compound to inhibit the conversion of ATP to AMP and/or ADP, either directly or indirectly. For soluble CD39, this can be measured by incubating recombinant soluble CD39 as described herein with a test compound and measuring the conversion of ATP to AMP and/or ADP, either directly or indirectly. For example, disappearance of ATP and/or generation of AMP can be assessed, as described herein. For example disappearance of ATP and/or generation of AMP can be assessed by quantifying luminescence units which are proportional to the amount of ATP present. In one embodiment, an antibody preparation causes at least a 60% decrease in the conversion of ATP to AMP, at least a 70% decrease in the conversion of ATP to AMP, or at least an 80% or 90% decrease in the conversion of ATP to AMP, referring, for example, to the assays described herein (e.g., disappearance of ATP and/or generation of AMP).

Whenever "treatment of cancer" or the like is mentioned with reference to anti-CD39 binding agent (e.g., antibody), this can include: (a) method of treatment of cancer, said method comprising the step of administering (for at least one treatment) an anti-CD39 binding agent, (preferably in a pharmaceutically acceptable carrier material) to an individual, a mammal, especially a human, in need of such treatment, in a dose that allows for the treatment of cancer, (a therapeutically effective amount), preferably in a dose (amount) as specified herein; (b) the use of an anti-CD39 binding agent for the treatment of cancer, or an anti-CD39 binding agent, for use in said treatment (especially in a human); (c) the use of an anti-CD39 binding agent for the manufacture of a pharmaceutical preparation for the treatment of cancer, a method of using an anti-CD39 binding agent for the manufacture of a pharmaceutical preparation for the treatment of cancer, optionally comprising admixing an anti-CD39 binding agent with a pharmaceutically acceptable carrier, or a pharmaceutical preparation comprising an effective dose of an anti-CD39 binding agent that is appropriate for the treatment of cancer; or (d) any combination of a), b), and c), in accordance with the subject matter allowable for patenting in a country where this application is filed.

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise at least one complementarity determining region (CDR) of an antibody chain. In another embodiment, the binding domain may comprise a polypeptide domain from a non-immunoglobulin scaffold.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g., CD39, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. antibody I-394, I-395, I-396, I-397, I-398 or I-399), it means that the antibody competes with the monoclonal antibody in a binding assay using either recombinant CD39 molecules or surface expressed CD39 molecules. For example, if a test antibody reduces the binding of a reference antibody to a CD39 polypeptide or CD39-expressing cell in a binding assay, the antibody is said to "compete" respectively with the reference antibody.

The term "affinity", as used herein, means the strength of the binding of an antibody to an epitope. The affinity of an antibody is given by the dissociation constant Kd, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g., the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "hypervariable region" when used herein refers to the amino acid residues of an antibody that are responsible for antigen binding. The hypervariable region generally comprises amino acid residues from a "complementarity-determining region" or "CDR" (e.g., residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g., residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917), or a similar system for determining essential amino acids responsible for antigen binding. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and µ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Antibodies

The anti-CD39 antigen binding domain, or a protein (e.g., antibody or antibody fragment) that comprises such domain, can be used for the treatment of cancers and/or other diseases (e.g., infectious disease) binds a soluble human CD39 polypeptide, e.g., a human CD39 polypeptide lacking the two transmembrane domains near the N- and C-terminal ends found in membrane bound CD39, for example an extracellular domain protein having the amino acid sequence of SEQ ID NO: 44. In one embodiment the agent inhibits the ATPase activity of CD39. In one embodiment the antibody inhibits CD39-mediated generation of adenosine. In one embodiment the antibody inhibits CD39-mediated catabolism of ATP to AMP. In one embodiment the antibody inhibits adenosine-mediated inhibition of lymphocyte activity (e.g., T cells). In one aspect, the antibody is selected from a full-length antibody, an antibody fragment, and a synthetic or semi-synthetic antibody-derived molecule.

The antibodies that potently inhibit the enzymatic (ATPase activity) activity of the soluble (and optionally the membrane-bound) CD39 protein may, in one embodiment, immobilize or restrict the domain movement of the soluble (and optionally the membrane-bound) CD39 protein in one of its conformations thereby preventing it from hydrolyzing its substrate. The antibodies may achieve this by binding to both C- and N-terminal domains of soluble (and optionally the membrane-bound) CD39 at the same time.

In one embodiment, an anti-CD39 antigen binding domain, or an antigen-binding protein that comprises the antigen binding domain (e.g., an antibody or antibody fragment, a multispecific binding protein, a bispecific antibody, etc.), comprises complementary determining regions (CDR) and framework regions (FR). The antigen binding domains can be designed or modified so as to provide desired and/or improved properties.

In one embodiment, an anti-CD39 antigen-binding protein is capable of binding to and inhibiting the activity of a human CD39 polypeptide, the antigen-binding protein comprising a VH and a VL that each comprise a framework (e.g., a framework having an amino acid sequence of human origin) and a CDR1, CDR2 and CDR3. In one embodiment, the antigen-binding protein restricts the domain movement of CD39 when bound to CD39. Optionally, the VH and/or VL framework (e.g., FR1, FR2, FR3 and/or FR4) is of human origin.

In certain embodiment, the binding molecules and domains can be derived from immunoglobulin variable domains, for example in the form of associated $V_L$ and $V_H$ domains found on two polypeptide chains, or a single chain antigen binding domain such as a scFv, a $V_H$ domain, a $V_L$ domain, a dAb, a V-NAR domain or a $V_H$H domain.

In one aspect, the CD39 binding agent is an antibody selected from a fully human antibody, a humanized antibody, and a chimeric antibody.

In one aspect, the agent is a fragment of an antibody comprising a constant or Fc domain derived from a human IgG1 constant or Fc domain, e.g., modified, as further disclosed herein.

In one aspect, the agent comprises an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent comprises a synthetic or semisynthetic antibody-derived molecule selected from a scFV, a dsFV, a minibody, a diabody, a triabody, a kappa body, an IgNAR; and a multispecific (e.g., bispecific) antibody. The agent can optionally further comprise an Fc domain.

In one aspect, the antibody is in at least partially purified form.

In one aspect, the antibody is in essentially isolated form.

Antibodies may be produced by a variety of techniques known in the art. In one embodiment, antibodies of the disclosure are produced by selection from an antibody library (e.g., as generated from phage display library). In another embodiment, antibodies are produced by immunization of a non-human animal, preferably a mouse, with an immunogen comprising a CD39 polypeptide, preferably a soluble human CD39 extracellular domain polypeptide. The CD39 polypeptide may optionally be or comprise a fragment or derivative of a full-length CD39 polypeptide, typically an immunogenic fragment, i.e., a portion of the polypeptide comprising an epitope exposed on the surface of cells expressing a CD39 polypeptide. Such fragments typically contain at least about 7 consecutive amino acids of the mature polypeptide sequence, even more preferably at least about 10 consecutive amino acids thereof. Fragments typically are essentially derived from the extra-cellular domain of the receptor. In one embodiment, the immunogen comprises a wild-type human CD39 polypeptide in a lipid membrane, typically at the surface of a cell. In a specific embodiment, the immunogen comprises intact cells, particularly intact human cells, optionally treated or lysed. In another embodiment, the polypeptide is a recombinant CD39 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Isolation of hybridomas producing the antibodies is well known and can be carried out in any manner well known in the art.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to CD39, particularly substantially or essentially the same region on CD39 as monoclonal antibody I-394, can be readily determined using any one of a variety of immunological screening assays in which antibody competition can be assessed. Many such assays are routinely practiced and are well known in the art (see, e. g., U.S. Pat. No. 5,660,827, issued Aug. 26, 1997, which is specifically incorporated herein by reference).

For example, where the test antibodies to be examined are obtained from different source animals, or are even of a different Ig isotype, a simple competition assay may be employed in which the control (1-394, for example) and test antibodies are admixed (or pre-adsorbed) and applied to a sample containing CD39 polypeptides. Protocols based upon western blotting and the use of BIACORE analysis are suitable for use in such competition studies.

In certain embodiments, one pre-mixes the control antibodies (1-394, for example) with varying amounts of the test antibodies (e.g., about 1:10 or about 1:100) for a period of time prior to applying to the CD39 antigen sample. In other embodiments, the control and varying amounts of test antibodies can simply be admixed during exposure to the CD39 antigen sample. As long as one can distinguish bound from free antibodies (e. g., by using separation or washing techniques to eliminate unbound antibodies) and I-394 from the test antibodies (e. g., by using species-specific or isotype-specific secondary antibodies or by specifically labelling I-394 with a detectable label) one can determine if the test antibodies reduce the binding of respective I-394 to the antigens. The binding of the (labelled) control antibodies in the absence of a completely irrelevant antibody can serve as the control high value. The control low value can be obtained by incubating the labelled (I-394) antibodies with unlabelled antibodies of exactly the same type (I-394), where competition would occur and reduce binding of the labelled antibodies. In a test assay, a significant reduction in labelled antibody reactivity in the presence of a test antibody is indicative of a test antibody that may recognize the same region or epitope on CD39. A test antibody can be selected that reduces the binding of I-394 to CD39 antigens by at least about 50%, such as at least about 60%, or more preferably at least about 80% or 90% (e. g., about 65-100%), at any ratio of I-394:test antibody between about 1:10 and about 1:100. Preferably, such test antibody will reduce the binding of I-394 to the CD39 antigen by at least about 90% (e.g., about 95%).

Competition can also be assessed by, for example, a flow cytometry test. In such a test, cells bearing a given CD39 polypeptide can be incubated first with I-394, for example, and then with the test antibody labelled with a fluorochrome or biotin. The antibody is said to compete with I-394 if the binding obtained upon preincubation with a saturating amount of the respective I-394 is about 80%, preferably about 50%, about 40% or less (e.g., about 30%, 20% or 10%) of the binding (as measured by mean of fluorescence) obtained by the antibody without preincubation with the respective I-394. Alternatively, an antibody is said to compete with I-394 if the binding obtained with a labelled I-394 antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a CD39 antigen is immobilized may also be employed. The surface in the simple competition assay is preferably a BIACORE chip (or other media suitable for surface plasmon resonance analysis). The control antibody (e.g., I-394) is then brought into contact with the surface at a CD39-saturating concentration and the CD39 and surface binding of the control antibody is measured. This binding of the control antibody is compared with the binding of the control antibody to the CD39-containing surface in the absence of test antibody. In a test assay, a significant reduction in binding of the CD39-containing surface by the control antibody in the presence of a test antibody indicates that the test antibody "cross-reacts" with the control antibody. Any test antibody that reduces the binding of control (such as I-394) antibody to a CD39 antigen by at least about 30% or more, preferably about 40%, can be considered to be an antibody that competes with a control (e.g., I-394). Preferably, such a test antibody will reduce the binding of the control antibody (e.g., I-394) to the CD39 antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the CD39 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

In one embodiment, the antibodies are validated in an immunoassay to test their ability to bind to soluble CD39 and/or CD39-expressing cells, e.g., malignant cells. For example, a blood sample or tumor biopsy is performed and soluble CD39 is isolated and/or tumor cells are collected. The ability of a given antibody to bind to the sCD39 and/or cells is then assessed using standard methods well known to those in the art. Antibodies may bind for example to a substantial proportion (e.g., 20%, 30%, 40%, 50%, 60%, 70%, 80% or more) of cells known to express CD39, e.g., tumor cells, from a significant percentage of individuals or patients (e.g., 10%, 20%, 30%, 40%, 50% or more). Antibodies can be used for diagnostic purposes to determine the presence or level of sCD39 and/or malignant cells in a patient, for example as a biomarker to assess whether a patient is suitable for treatment with an anti-CD39 agent, or for use in the herein-described therapeutic methods. To assess the binding of the antibodies to the sCD39 and/or cells, the antibodies can either be directly or indirectly labelled. When indirectly labelled, a secondary, labelled antibody is typically added.

Determination of whether an antibody binds within an epitope region can be carried out in ways known to the person skilled in the art. As one example of such mapping/characterization methods, an epitope region for an anti-CD39 antibody may be determined by epitope "foot-printing" using chemical modification of the exposed amines/carboxyls in the CD39 protein. One specific example of such a foot-printing technique is the use of HXMS (hydrogen-deuterium exchange detected by mass spectrometry)

wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g., by using trypsin in a ratio of about 1:50 to CD39 or o/n digestion at and pH 7-8, followed by mass spectrometry (MS) analysis for peptide identification. The peptides protected from trypsin cleavage by the anti-CD39 binder can subsequently be identified by comparison of samples subjected to trypsin digestion and samples incubated with antibody and then subjected to digestion by e.g., trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the CD39 polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fagerstam et al., Journal Of Molecular Recognition 1990; 3:208-14; Nice et al., J. Chroma-togr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody that binds the same or substantially the same epitope as an antibody can be identified in one or more of the exemplary competition assays described herein.

Upon immunization and production of antibodies in a vertebrate or cell, particular selection steps may be performed to isolate antibodies as claimed. In this regard, in a specific embodiment, the disclosure also relates to methods of producing such antibodies, comprising: (a) immunizing a non-human mammal with an immunogen comprising a CD39 polypeptide; and (b) preparing antibodies from said immunized animal; and (c) selecting antibodies from step (b) that are capable of binding CD39. Optionally, the antibodies selected that are capable of binding CD39 are then purified and tested for the ability to inhibit the ATPase activity of CD39 (e.g. according to any of the methods herein).

Typically, an anti-CD39 antibody provided herein has an affinity for a CD39 polypeptide (e.g., a monomeric CD39 polypeptide as produced in the Examples herein) in the range of about $10^4$ to about $10^{11}$ $M^{-1}$ (e.g., about $10^8$ to about $10^{10}$ $M^{-1}$). For example, anti-CD39 antibodies can have an average disassociation constant ($K_D$) of less than $1 \times 10^{-9}$ M with respect to CD39, as determined by, e.g., surface plasmon resonance (SPR) screening (such as by analysis with a BIAcore™ SPR analytical device). In a more particular exemplary aspect, the disclosure provides anti-CD39 antibodies that have a KD of about $1 \times 10^{-8}$ M to about $1 \times 10^{-10}$ M, or about $1 \times 10^{-9}$ M to about $1 \times 10^{-11}$ M, for CD39. Antibodies can be characterized for example by a mean $K_D$ of no more than about (i.e. better affinity than) 100, 60, 10, 5, or 1 nanomolar, preferably sub-nanomolar or optionally no more than about 500, 200, 100 or 10 picomolar. $K_D$ can be determined for example for example by immobilizing recombinantly produced human CD39 proteins on a chip surface, followed by application of the antibody to be tested in solution. In one embodiment, the method further comprises a step (d), selecting antibodies from (b) that are capable of competing for binding to CD39 with antibody I-394, I-395, I-396, I-397, I-398 or I-399.

In one aspect of any of the embodiments, the antibodies prepared according to the present methods are monoclonal antibodies. In another aspect, the non-human animal used to produce antibodies according to the methods herein is a mammal, such as a rodent, bovine, porcine, fowl, horse, rabbit, goat, or sheep.

DNA encoding an antibody that binds an epitope present on CD39 polypeptides is isolated from a hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the disclosure, e.g., antibody I-394, can be readily isolated and sequenced using conventional procedures (e. g., by using oligonucleotide probes that are capable of binding specifically to genes encoding the heavy and light chains of murine antibodies). In one aspect, provided is a nucleic acid encoding a heavy chain or a light chain of an anti-CD39 antibody of any embodiment herein. Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. In one embodiment, provided is an isolated nucleic acid sequence encoding a light chain and/or a heavy chain of an antibody (e.g., I-394), as well as a recombinant host cell comprising (e.g., in its genome) such nucleic acid. Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Once antibodies are identified that are capable of binding sCD39 and/or memCD39, and/or having other desired properties, they will also typically be assessed, using methods such as those described herein, for their ability to bind to other polypeptides, including unrelated polypeptides. Ideally, the antibodies bind with substantial affinity only to CD39, and do not bind at a significant level to unrelated polypeptides, or other polypeptides of the NTPDase family, notably CD39-L1, L2, L3 and L4 or NTPDase8. However, it will be appreciated that, as long as the affinity for CD39 is substantially greater (e.g., 10×, 100×, 500×, 1000×, 10,000×, or more) than it is for other, unrelated polypeptides), then the antibodies are suitable for use in the present methods.

In one embodiment, the anti-CD39 antibodies can be prepared such that they do not have substantial specific binding to human Fcγ receptors, e.g., any one or more of CD16A, CD16B, CD32A, CD32B and/or CD64). Such antibodies may comprise constant regions of various heavy chains that are known to lack or have low binding to Fcγ receptors. Alternatively, antibody fragments that do not comprise (or comprise portions of) constant regions, such as F(ab')2 fragments, can be used to avoid Fc receptor binding. Fc receptor binding can be assessed according to methods known in the art, including for example testing binding of an antibody to Fc receptor protein in a BIACORE assay. Also, generally any antibody IgG isotype can be used in which the Fc portion is modified (e.g., by introducing 1, 2, 3, 4, 5 or more amino acid substitutions) to minimize or eliminate binding to Fc receptors (see, e.g., WO 03/101485, the disclosure of which is herein incorporated by reference). Assays such as cell based assays, to assess Fc receptor binding are well known in the art, and are described in, e.g., WO 03/101485.

In one embodiment, the antibody can comprise one or more specific mutations in the Fc region that result in "Fc silent" antibodies that have minimal interaction with effector cells. Silenced effector functions can be obtained by mutation in the Fc region of the antibodies and have been described in the art: N297A mutation, the LALA mutations, (Strohl, W., 2009, Curr. Opin. Biotechnol. Vol. 20(6):685-691); and D265A (Baudino et al., 2008, J. Immunol. 181: 6664-69) see also Heusser et al., WO2012/065950, the disclosures of which are incorporated herein by reference. In one embodiment, an antibody comprises one, two, three or more amino acid substitutions in the hinge region. In one embodiment, the antibody is an IgG1 or IgG2 and comprises one, two or three substitutions at residues 233-236, optionally 233-238 (EU numbering). In one embodiment, the antibody is an IgG4 and comprises one, two or three substitutions at residues 327, 330 and/or 331 (EU numbering). Examples of silent Fc IgG1 antibodies are the LALA mutant comprising L234A and L235A mutation in the IgG1 Fc amino acid sequence. Another example of an Fc silent mutation is a mutation at residue D265, or at D265 and P329 for example as used in an IgG1 antibody as the DAPA (D265A, P329A) mutation (U.S. Pat. No. 6,737,056). Another silent IgG1 antibody comprises a mutation at residue N297 (e.g., N297A, N297S mutation), which results in aglycosylated/non-glycosylated antibodies. Other silent mutations include: substitutions at residues L234 and G237 (L234A/G237A); substitutions at residues S228, L235 and R409 (S228P/L235E/R409K,T,M,L); substitutions at residues H268, V309, A330 and A331 (H268Q/V309L/A330S/A331S); substitutions at residues C220, C226, C229 and P238 (C220S/C226S/C229S/P238S); substitutions at residues C226, C229, E233, L234 and L235 (C226S/C229S/E233P/L234V/L235A; substitutions at residues K322, L235 and L235 (K322A/L234A/L235A); substitutions at residues L234, L235 and P331 (L234F/L235E/P331S); substitutions at residues 234, 235 and 297; substitutions at residues E318, K320 and K322 (L235E/E318A/K320A/K322A); substitutions at residues (V234A, G237A, P238S); substitutions at residues 243 and 264; substitutions at residues 297 and 299; substitutions such that residues 233, 234, 235, 237, and 238 defined by the EU numbering system, comprise a sequence selected from PAAAP, PAAAS and SAAAS (see WO2011/066501).

In one embodiment, the antibody can comprise one or more specific mutations in the Fc region. For example, such an antibody can comprise an Fc domain of human IgG1 origin, comprises a mutation at Kabat residue(s) 234, 235, 237, 330 and/or 331. One example of such an Fc domain comprises substitutions at Kabat residues L234, L235 and P331 (e.g., L234A/L235E/P331S or (L234F/L235E/P331S). Another example of such an Fc domain comprises substitutions at Kabat residues L234, L235, G237 and P331 (e.g., L234A/L235E/G237A/P331S). Another example of such an Fc domain comprises substitutions at Kabat residues L234, L235, G237, A330 and P331 (e.g., L234A/L235E/G237A/A330S/P331S). In one embodiment, the antibody comprises an Fc domain, optionally of human IgG1 isotype, comprising: a L234$X_1$ substitution, a L235$X_2$ substitution, and a P331$X_3$ substitution, wherein $X_1$ is any amino acid residue other than leucine, $X_2$ is any amino acid residue other than leucine, and $X_3$ is any amino acid residue other than proline; optionally wherein $X_1$ is an alanine or phenylalanine or a conservative substitution thereof; optionally wherein $X_2$ is glutamic acid or a conservative substitution thereof; optionally wherein $X_3$ is a serine or a conservative substitution thereof. In another embodiment, the antibody comprises an Fc domain, optionally of human IgG1 isotype, comprising: a L234$X_1$ substitution, a L235$X_2$ substitution, a G237$X_4$ substitution and a P331$X_4$ substitution, wherein $X_1$ is any amino acid residue other than leucine, $X_2$ is any amino acid residue other than leucine, $X_3$ is any amino acid residue other than glycine, and $X_4$ is any amino acid residue other than proline; optionally wherein $X_1$ is an alanine or phenylalanine or a conservative substitution thereof; optionally wherein $X_2$ is glutamic acid or a conservative substitution thereof; optionally, $X_3$ is alanine or a conservative substitution thereof; optionally $X_4$ is a serine or a conservative substitution thereof. In another embodiment, the antibody comprises an Fc domain, optionally of human IgG1 isotype, comprising: a L234$X_1$ substitution, a L235$X_2$ substitution, a G237$X_4$ substitution, G330$X_4$ substitution, and a P331$X_5$ substitution, wherein $X_1$ is any amino acid residue other than leucine, $X_2$ is any amino acid residue other than leucine, $X_3$ is any amino acid residue other than glycine, $X_4$ is any amino acid residue other than alanine, and $X_5$ is any amino acid residue other than proline; optionally wherein $X_1$ is an alanine or phenylalanine or a conservative substitution thereof; optionally wherein $X_2$ is glutamic acid or a conservative substitution thereof; optionally, $X_3$ is alanine or a conservative substitution thereof; optionally, $X_4$ is serine or a conservative substitution thereof; optionally $X_5$ is a serine or a conservative substitution thereof. In the shorthand notation used here, the format is: Wild type residue: Position in polypeptide: Mutant residue, wherein residue positions are indicated according to EU numbering according to Kabat.

In one embodiment, an antibody comprises a heavy chain constant region comprising the amino acid sequence below, or an amino acid sequence at least 90%, 95% or 99% identical thereto but retaining the amino acid residues at Kabat positions 234, 235 and 331 (underlined):

```
                                                  (SEQ ID NO: 38)
A S T K G P S V F P L A P S S K S T S G G T A A L G C L V K D Y F P

E P V T V S W N S G A L T S G V H T F P A V L Q S S G L Y S L S S V

V T V P S S S L G T Q T Y I C N V N H K P S N T K V D K R V E P K S

C D K T H T C P P C P A P E A E G G P S V F L F P P K P K D T L M I

S R T P E V T C V V V D V S H E D P E V K F N W Y V D G V E V H N A

K T K P R E E Q Y N S T Y R V V S V L T V L H Q D W L N G K E Y K C

K V S N K A L P A S I E K T I S K A K G Q P R E P Q V Y T L P P S R

E E M T K N Q V S L T C L V K G F Y P S D I A V E W E S N G Q P E N

N Y K T T P P V L D S D G S F F L Y S K L T V D K S R W Q Q G N V F

S C S V M H E A L H N H Y T Q K S L S L S P G K
```

In one embodiment, an antibody comprises a heavy chain constant region comprising the amino acid sequence below, or an amino acid sequence at least 90%, 95% or 99% identical thereto but retaining the amino acid residues at Kabat positions 234, 235 and 331 (underlined):

```
                                                  (SEQ ID NO: 39)
A S T K G P S V F P L A P S S K S T S G G T A A L G C L V K D Y F P

E P V T V S W N S G A L T S G V H T F P A V L Q S S G L Y S L S S V

V T V P S S S L G T Q T Y I C N V N H K P S N T K V D K R V E P K S

C D K T H T C P P C P A P E F E G G P S V F L F P P K P K D T L M I

S R T P E V T C V V V D V S H E D P E V K F N W Y V D G V E V H N A

K T K P R E E Q Y N S T Y R V V S V L T V L H Q D W L N G K E Y K C

K V S N K A L P A S I E K T I S K A K G Q P R E P Q V Y T L P P S R

E E M T K N Q V S L T C L V K G F Y P S D I A V E W E S N G Q P E N

N Y K T T P P V L D S D G S F F L Y S K L T V D K S R W Q Q G N V F

S C S V M H E A L H N H Y T Q K S L S L S P G K
```

In one embodiment, an antibody comprises a heavy chain constant region comprising the amino acid sequence below, or an amino acid sequence at least 90%, 95% or 99% identical thereto but retaining the amino acid residues at Kabat positions 234, 235, 237, 330 and 331 (underlined):

```
                                                  (SEQ ID NO: 40)
A S T K G P S V F P L A P S S K S T S G G T A A L G C L V K D Y F P

E P V T V S W N S G A L T S G V H T F P A V L Q S S G L Y S L S S V

V T V P S S S L G T Q T Y I C N V N H K P S N T K V D K R V E P K S
```

```
                                    -continued
C D K T H T C P P C P A P E A E G A P S V F L F P P K P K D T L M I
                          ᅳ ᅳ   ᅳ

S R T P E V T C V V V D V S H E D P E V K F N W Y V D G V E V H N A

K T K P R E E Q Y N S T Y R V V S V L T V L H Q D W L N G K E Y K C

K V S N K A L P S S I E K T I S K A K G Q R E P Q V Y T L P P S R
                ᅳ ᅳ

E E M T K N Q V S L T C L V K G F Y P S D I A V E W E S N G Q P E N

N Y K T T P P V L D S D G S F F L Y S K L T V D K S R W Q Q G N V F

S C S V M H E A L H N H Y T Q K S L S L S P G K
```

In one embodiment, an antibody comprises a heavy chain constant region comprising the amino acid sequence below, or a sequence at least 90%, 95% or 99% identical thereto but retaining the amino acid residues at Kabat positions 234, 235, 237 and 331 (underlined):

```
                                                (SEQ ID NO: 41)
A S T K G P S V F P L A P S S K S T S G G T A A L G C L V K D Y F P

E P V T V S W N S G A L T S G V H T F P A V L Q S S G L Y S L S S V

V T V P S S S L G T Q T Y I C N V N H K P S N T K V D K R V E P K S

C D K T H T C P P C P A P E A E G A P S V F L F P P K P K D T L M I
                          ᅳ ᅳ   ᅳ

S R T P E V T C V V V D V S H E D P E V K F N W Y V D G V E V H N A

K T K P R E E Q Y N S T Y R V V S V L T V L H Q D W L N G K E Y K C

K V S N K A L P A S I E K T I S K A K G Q R E P Q V Y T L P P S R
                  ᅳ

E E M T K N Q V S L T C L V K G F Y P S D I A V E W E S N G Q P E N

N Y K T T P P V L D S D G S F F L Y S K L T V D K S R W Q Q G N V F

S C S V M H E A L H N H Y T Q K S L S L S P G K
```

Fc silent antibodies result in no or low ADCC activity, meaning that an Fc silent antibody exhibits an ADCC activity that is below 50% specific cell lysis. Preferably an antibody substantially lacks ADCC activity, e.g., the Fc silent antibody exhibits an ADCC activity (specific cell lysis) that is below 5% or below 1%. Fc silent antibodies can also result in lack of FcγR-mediated cross-linking of CD39 at the surface of a CD39-expression.

In one embodiment, the antibody has a substitution in a heavy chain constant region at any one, two, three, four, five or more of residues selected from the group consisting of: 220, 226, 229, 233, 234, 235, 236, 237, 238, 243, 264, 268, 297, 298, 299, 309, 310, 318, 320, 322, 327, 330, 331 and 409 (numbering of residues in the heavy chain constant region is according to EU numbering according to Kabat). In one embodiment, the antibody comprises a substitution at residues 234, 235 and 322. In one embodiment, the antibody has a substitution at residues 234, 235 and 331. In one embodiment, the antibody has a substitution at residues 234, 235, 237 and 331. In one embodiment, the antibody has a substitution at residues 234, 235, 237, 330 and 331. In one embodiment, the Fc domain is of human IgG1 subtype. Amino acid residues are indicated according to EU numbering according to Kabat.

In one embodiment, the antibody comprises an Fc domain comprising an amino acid substitution that increases binding to human FcRn polypeptides in order to increase the in vivo half-life of the antibody. Exemplary mutations are described in Strohl, W., 2009, Curr. Opin. Biotechnol. vol. 20(6):685-691, the disclosure of which is incorporated herein by reference. Examples of substitutions used in antibodies of human IgG1 isotype are substitutions at residues M252, S254 and T256; substitutions at residues T250 and M428; substitutions at residue N434; substitutions at residues H433 and N434; substitutions at residues T307, E380 and N434; substitutions at residues T307, E380, and N434; substitutions at residues M252, S254, T256, H433, N434 and 436; substitutions at residue 1253; substitutions at residues P257, N434, D376 and N434.

In one embodiment, the antibody comprises an Fc domain comprising an amino acid substitution that confers decreased sensitivity to cleavage by proteases. Matrix metalloproteinases (MMPs) represent the most prominent family of proteinases associated with tumorigenesis. While cancer cells can express MMPs, the bulk of the extracellular MMP is provided by different types of stromal cells that infiltrate the tumor and each produce a specific set of proteinases and proteinase inhibitors, which are released into the extracellular space and specifically alter the milieu around the tumor. The MMPs present in the tumor microenvironment can cleave antibodies within the hinge region and may thus lead to the inactivation of therapeutic antibodies that are designed to function within the tumor site. In one embodiment, the Fc domain comprising an amino acid substitution has decreased sensitivity to cleavage by any one, two, three or more (or all of) of the proteases selected from the group consisting of: GluV8, IdeS, gelatinase A (MMP2), gelatinase B (MMP-9), matrix metalloproteinase-7 (MMP-7), stromelysin (MMP-3), and macrophage elastase (MMP-12). In one embodiment, the antibody decreased sensitivity to cleavage comprises an Fc domain comprising an amino acid substitution at residues E233-L234 and/or L235. In one embodiment, the antibody comprises an Fc domain comprising an amino acid substitution at residues E233, L234, L235 and G236. In one embodiment, the antibody comprises an Fc domain comprising an amino acid substitution at one or more residues 233-238, e.g., such that E233-L234-L235-G236 sequence is replaced by P233-V234-A235 (G236 is deleted). See, e.g., WO99/58572 and WO2012087746, the disclosures of which are incorporated herein by reference.

An antigen-binding compound can at any desired stage be assessed for its ability to inhibit the enzymatic activity of CD39, notably to block the ATPase activity of sCD39 and to reduce the production of ADP and AMP (and, together with CD73, adenosine) by soluble CD39 protein and optionally further by a CD39-expressing cell, and in turn restore the activity of and/or relieve the adenosine-mediated inhibition of lymphocytes.

The inhibitory activity (e.g., immune enhancing potential) of an antibody can be assessed for example, in an assay to detect the disappearance (hydrolysis) of ATP and/or the generation of AMP.

The ability of an antibody to inhibit soluble recombinant human CD39 protein can be tested by detecting ATP after incubating test antibody with soluble CD39 protein (e.g., the protein having the amino acid sequence of SEQ ID NO 44 or 45, as produced in Examples, Methods, optionally further comprising a purification tag or other functional or non-functional non-CD39-derived amino acid sequence). See, e.g., Examples. Methods. Briefly, ATP can be quantified using the Cell Titer Glo™ (Promega), in an assay in which dose ranges of test antibody are incubated with soluble recombinant human CD39 protein described in Example 1, for 1 hour at 37° C. 20 µM ATP are added to the plates for 30 additional minutes at 37° C. before addition of CTG reagent. Emitted light is quantified using an Enspire™ luminometer after a short incubation period of 5 min in the dark.

The ability of an antibody to inhibit cells expressing CD39 protein can be tested by detecting ATP after incubating test antibody with cells (e.g., Ramos cells, cells transfected with CD39, etc.). See, e.g., Examples, Methods. Cells can be incubated for 1 hour at 37° C. with test antibody. Cells are then incubated with 20 µM ATP for 1 additional hour at 37° C. Plates are centrifuged for 2 min at 400 g and cell supernatant are transferred in a luminescence microplate (white wells). CTG is added to the supernatant and emitted light is quantified after a 5 min incubation in the dark using an Enspire™ luminometer. Anti-CD39 antibody efficacy is determined by comparing emitted light in presence of antibody with ATP alone (maximal light emission) and ATP together with cells (minimal light emission).

A decrease in hydrolysis of ATP into AMP, and/or an increase of ATP and/or a decrease in generation of AMP, in the presence of antibody indicate the antibody inhibits CD39. In one embodiment, an antibody preparation is capable of causing at least a 60% decrease in the enzymatic activity of a CD39 polypeptide expressed by a cell, preferably the antibody causes at least a 70%, 80% or 90% decrease in the enzymatic activity of a CD39 polypeptide in a cell, as assessed by detecting ATP using the Cell Titer Glo™ (Promega) after incubating cells expressing CD39 polypeptide (e.g., Ramos cells) with a test antibody, e.g., as in Examples, Methods.

In one embodiment, an antibody preparation is capable of causing at least a 60% decrease in the enzymatic activity of a soluble recombinant CD39 polypeptide (e.g. in the absence of cells), preferably at least a 70%, 80% or 90% decrease in the enzymatic activity of a soluble recombinant CD39 polypeptide, as assessed by detecting ATP using the Cell Titer Glo™ (Promega) after incubating soluble recombinant CD39 polypeptide with a test antibody, e.g., as in Example, Methods.

The activity of an antibody can also be measured in an indirect assay for its ability to modulate the activity of immune cells (e.g., adenosine receptor-expressing immune cells; A2A-receptor expressing cells), for example to relieve the adenosine-mediated inhibition of lymphocyte activity, or to cause the activation of lymphocyte activity. This can be addressed, for example, using a cytokine-release assay. In another example, an antibody can be evaluated in an indirect assay for its ability to modulate the proliferation of lymphocytes.

In one example, provided is a method for producing or identifying an anti-CD39 antibody or antigen binding domain, the method comprising the steps of:
(a) providing a plurality of samples comprising an antibody that bind a human CD39 polypeptide (e.g. cell culture supernatants, hybridoma supernatants),
(b) subjecting the samples to purification step to obtain a plurality of samples each comprising purified monoclonal antibody, bringing each of the antibody samples into contact with soluble extracellular domain CD39 protein (e.g. in the absence of cells) and assessing neutralization of ATPase activity thereof, and
(c) selecting an antibody of step (b) that results in a neutralization of ATPase activity, optionally selecting an antibody that results in neutralization of at least 70%, optionally 80% or optionally 90%. In one embodiment, step (a) comprising immunizing one or more non-human mammal(s) with a CD39 polypeptide, and obtaining from such mammal(s) a plurality samples comprising an antibody that bind a human CD39 polypeptide.

In one example, provided is a method for producing or identifying an anti-CD39 antibody or antigen binding domain, the method comprising the steps of:
(a) providing a plurality of purified antibodies that bind a human CD39 polypeptide,
(b) bringing each of the antibodies into contact with soluble extracellular domain CD39 protein and assessing neutralization of ATPase activity thereof, and
(c) selecting an antibody of step (b) that results in a neutralization of ATPase activity, by at least 70%, optionally 80% or optionally 90%.

Optionally, the methods may further comprises the steps of:
(d) bringing each of the antibodies into contact with CD39-expressing cells, optionally human B cells, optionally Ramos human lymphoma cells and assessing neutralization of ATPase activity; and
(e) selecting an antibody of step (d) that results in a decrease of ATPase activity by at least 70%, optionally 80% or optionally 90%. Steps (b) and (c) can be performed either before or after steps (d) and (e).

Epitopes on CD39

In one aspect, the antibodies bind an antigenic determinant present on CD39 expressed at the cell surface.

In one aspect, the antibodies bind substantially the same epitope as antibody I-394, I-395, I-396, I-397 or I-398. In one embodiment, the antibodies bind to an epitope of CD39 that at least partially overlaps with, or includes at least one residue in, the epitope bound by antibody I-394, I-395, I-396, I-397 or I-398. The residues bound by the antibody can be specified as being present on the surface of the CD39 polypeptide, e.g., in a CD39 polypeptide expressed on the surface of a cell.

Binding of anti-CD39 antibody to cells transfected with CD39 mutants can be measured and compared to the ability of anti-CD39 antibody to bind wild-type CD39 polypeptide (e.g., SEQ ID NO: 1). A reduction in binding between an anti-CD39 antibody and a mutant CD39 polypeptide (e.g., a mutant of Table 1) means that there is a reduction in binding affinity (e.g., as measured by known methods such FACS testing of cells expressing a particular mutant, or by Biacore testing of binding to mutant polypeptides) and/or a reduction in the total binding capacity of the anti-CD39 antibody (e.g., as evidenced by a decrease in Bmax in a plot of anti-CD39 antibody concentration versus polypeptide concentration). A significant reduction in binding indicates that the mutated residue is directly involved in binding to the anti-CD39 antibody or is in close proximity to the binding protein when the anti-CD39 antibody is bound to CD39.

In some embodiments, a significant reduction in binding means that the binding affinity and/or capacity between an anti-CD39 antibody and a mutant CD39 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type CD39 polypeptide. In certain embodiments, binding is reduced below detectable limits.

In some embodiments, a significant reduction in binding is evidenced when binding of an anti-CD39 antibody to a mutant CD39 polypeptide is less than 50% (e.g., less than 45%, 40%, 35%, 30%, 25%, 20%, 15% or 10%) of the binding observed between the anti-CD39 antibody and a wild-type CD39 polypeptide.

In some embodiments, anti-CD39 antibodies are provided that exhibit significantly lower binding for a mutant CD39 polypeptide in which a residue in a segment comprising an amino acid residue bound by antibody I-394, I-395, I-396, I-397, I-398 or I-399 is substituted with a different amino acid, compared to a binding to a wild-type CD39 polypeptide not comprising such substitution(s) (e.g. a polypeptide of SEQ ID NO: 1).

In some embodiments, anti-CD39 antibodies (e.g., other than I-394) are provided that bind the epitope on CD39 bound by antibody I-394.

In any embodiment herein, an antibody can be characterized as an antibody other than BY40, BY12 or BA54 g (or an antibody sharing its CDRs) referenced in PCT publication no. WO2009/095478, the disclosure of which is incorporated herein by reference.

In one aspect, the anti-CD39 antibodies have reduced binding to a CD39 polypeptide having a mutation at a residue selected from the group consisting of: Q96, N99, E143 and R147 (with reference to SEQ ID NO: 1); optionally, the mutant CD39 polypeptide has the mutations: Q96A, N99A, E143A and R147E. In one aspect, the anti-CD39 antibodies bind an epitope on CD39 comprising an amino acid residue (e.g., one, two, three or four of the residues) selected from the group consisting of Q96, N99, E143 and R147 (with reference to SEQ ID NO: 1).

In one embodiment, an antibody has reduced binding to a mutant CD39 polypeptide comprising a mutation at one or more (or all of) residues selected from the group consisting of R138, M139 and E142 (with reference to SEQ ID NO: 1), in each case relative to binding between the antibody and a wild-type CD39 polypeptide comprising the amino acid sequence of SEQ ID NO: 1.

In one embodiment, an antibody has reduced binding to a mutant CD39 polypeptide comprising a mutation at one or more (or all of) residues selected from the group consisting of K87, E100 and D107 (with reference to SEQ ID NO: 1), in each case relative to binding between the antibody and a wild-type CD39 polypeptide comprising the amino acid sequence of SEQ ID NO: 1.

In one embodiment, an antibody has reduced binding to a mutant CD39 polypeptide comprising a mutation at one or more (or all of) residues selected from the group consisting of N371, L372, E375, K376 and V377 (with reference to SEQ ID NO: 1), in each case relative to binding between the antibody and a wild-type CD39 polypeptide comprising the amino acid sequence of SEQ ID NO: 1.

Exemplary Antibody Variable Region Sequences

An exemplary anti-CD39 VH and VL pair according to the disclosure is that of antibody I-394, the amino acid sequence of the heavy chain variable region of which is listed below (SEQ ID NO: 6), and the amino acid sequence of the light chain variable region of which is listed below (SEQ ID NO: 7). The CDRs according to Kabat numbering are underlined in SEQ ID NOS: 6 and 7. Optionally, the VH and VL comprise (e.g., are modified to incorporate) human acceptor frameworks. In one embodiment, an anti-CD39 antibody of the disclosure comprises the VH CDR1, CDR2 and/or CDR3 (e.g., according to Kabat numbering) of the heavy chain variable region having the amino acid sequence of SEQ ID NO: 6. In one embodiment, an anti-CD39 antibody of the disclosure comprise the VL CDR1, CDR2 and/or CDR3 (e.g., according to Kabat numbering) of the light chain variable region having the amino acid sequence of SEQ ID NO: 7. In one embodiment, an anti-CD39 antibody of the disclosure comprises a VH comprising the Kabat CDR1, CDR2 and/or CDR3 of the heavy chain variable region having the amino acid sequence of SEQ ID NO: 6 and a VL comprising a Kabat CDR1, CDR2 and/or CDR3 of the light chain variable region having the amino acid sequence of SEQ ID NO: 7.

```
I-394 VH:
                                            (SEQ ID NO: 6)
EVQLQQSGPELVKPGASVKMSCKASGYTFTDYNMHWVKQSHGRTLEWIG

YIVPLNGGSTFNQKFKGRATLTVNTSSRTAYMELRSLTSEDSAAYYCARG

GTRFAYWGQGTLVTVSA

I-394 VL:
                                            (SEQ ID NO: 7)
DIVLTQSPASLAVSLGQRATISCRASESVDNFGVSFMYWFQQKPGQPPN

LLIYGASNQGSGVPARFRGSGSGTDFSLNIHPMEADDTAMYFCQQTKEVP

YTFGGGTKLEIK
```

An anti-CD39 antibody may for example comprise: a HCDR1 comprising an amino acid sequence: DYNMH (SEQ ID NO: 8), or a sequence of at least 4 contiguous amino acids thereof, optionally wherein one or more of these amino acids may be substituted by a different amino acid; a HCDR2 comprising an amino acid sequence: YIVPLNGG-STFNQKFKG (SEQ ID NO: 9), or a sequence of at least 4, 5, 6, 7, 8, 9 or 10 contiguous amino acids thereof, optionally wherein one or more of these amino acids may be substituted by a different amino acid; a HCDR3 comprising an amino acid sequence: GGTRFAY (SEQ ID NO: 10), or a sequence of at least 4, 5 or 6 contiguous amino acids thereof, optionally wherein one or more of these amino acids may be substituted by a different amino acid; a LCDR1 comprising an amino acid sequence: RASESVDNFGVSFMY (SEQ ID NO: 11), or a sequence of at least 4, 5, 6, 7, 8, 9 or 10 contiguous amino acids thereof, optionally wherein one or more of these amino acids may be substituted by a different amino acid; a LCDR2 region comprising an amino acid sequence: GASNQGS (SEQ ID NO: 12) or a sequence of at least 4, 5 or 6 contiguous amino acids thereof, optionally wherein one or more of these amino acids may be substituted by a different amino acid; and/or a LCDR3 region of I-394 comprising an amino acid sequence: QQTKEVPYT (SEQ ID NO: 13), or a sequence of at least 4, 5, 6, 7 or 8 contiguous amino acids thereof, optionally wherein one or more of these amino acids may be deleted or substituted by a different amino acid. CDR positions may be according to Kabat numbering.

Another exemplary anti-CD39 VH and VL pair according to the disclosure is that of antibody I-395, the amino acid sequence of the heavy chain variable region of which is listed below (SEQ ID NO: 14), and the amino acid sequence of the light chain variable region of which is listed below (SEQ ID NO: 15). The CDRs according to Kabat numbering are underlined in SEQ ID NOS: 14 and 15. Optionally, the VH and VL comprise (e.g., are modified to incorporate) human acceptor frameworks. In one embodiment, an anti-CD39 antibody of the disclosure comprises the VH CDR1, CDR2 and/or CDR3 (e.g., according to Kabat numbering) of the heavy chain variable region having the amino acid sequence of SEQ ID NO: 14. In one embodiment, an anti-CD39 antibody of the disclosure comprise the VL CDR1, CDR2 and/or CDR3 (e.g., according to Kabat numbering) of the light chain variable region having the amino acid sequence of SEQ ID NO: 15. In one embodiment, an anti-CD39 antibody of the disclosure comprises a VH comprising the Kabat CDR1, CDR2 and/or CDR3 of the heavy chain variable region having the amino acid sequence of SEQ ID NO: 14 and a VL comprising a Kabat CDR1, CDR2 and/or CDR3 of the light chain variable region having the amino acid sequence of SEQ ID NO: 15.

```
I-395 VH:
                                         (SEQ ID NO: 14)
EVQLQQSGPELVKPGASVRMSCKASGYTFTDYNMHWVKKNHGKGLEWIG

YINPNNGGTTYNQKFKGKATLTVNTSSKTAYMELRSLTSEDSAVYYCTR

GGTRFASWGQGTLVTVSA

I-395 VL:
                                         (SEQ ID NO: 15)
NIVLTQSPASLAVSLGQRATISCRASESVDNYGISFMYWFQQKPGQPPK

LLIYAASTQGSGVPARFSGSGSGTDFSLNIHPMEEDDTAMYFCQQSKE

VPFTFGSGTKLEIK
```

An anti-CD39 antibody may for example comprise: a HCDR1 comprising an amino acid sequence: DYNMH (SEQ ID NO: 16), or a sequence of at least 4 contiguous amino acids thereof, optionally wherein one or more of these amino acids may be substituted by a different amino acid; a HCDR2 comprising an amino acid sequence: YINPNNGGTTYNQKFKG (SEQ ID NO: 17), or a sequence of at least 4, 5, 6, 7, 8, 9 or 10 contiguous amino acids thereof, optionally wherein one or more of these amino acids may be substituted by a different amino acid; a HCDR3 comprising an amino acid sequence: GGTRFAS (SEQ ID NO: 18), or a sequence of at least 4, 5, 6 contiguous amino acids thereof, optionally wherein one or more of these amino acids may be substituted by a different amino acid; a LCDR1 comprising an amino acid sequence: RASESVDNYGISFMY (SEQ ID NO: 19), or a sequence of at least 4, 5, 6, 7, 8, 9 or 10 contiguous amino acids thereof, optionally wherein one or more of these amino acids may be substituted by a different amino acid; a LCDR2 region comprising an amino acid sequence: AASTQGS (SEQ ID NO: 20) or a sequence of at least 4, 5 or 6 contiguous amino acids thereof, optionally wherein one or more of these amino acids may be substituted by a different amino acid; and/or a LCDR3 region of I-396 comprising an amino acid sequence: QQSKEVPFT (SEQ ID NO: 21), or a sequence of at least 4, 5, 6, 7 or 8 contiguous amino acids thereof, optionally wherein one or more of these amino acids may be deleted or substituted by a different amino acid. CDR positions may be according to Kabat numbering.

Another exemplary anti-CD39 VH and VL pair according to the disclosure is that of antibody I-396, the amino acid sequence of the heavy chain variable region of which is listed below (SEQ ID NO: 22), and the amino acid sequence of the light chain variable region of which is listed below (SEQ ID NO: 23). The CDRs according to Kabat numbering are underlined in SEQ ID NOS: 22 and 23. Optionally, the VH and VL comprise (e.g., are modified to incorporate) human acceptor frameworks. In one embodiment, an anti-CD39 antibody of the disclosure comprises the VH CDR1, CDR2 and/or CDR3 (e.g., according to Kabat numbering) of the heavy chain variable region having the amino acid sequence of SEQ ID NO: 22. In one embodiment, an anti-CD39 antibody of the disclosure comprise the VL CDR1, CDR2 and/or CDR3 (e.g., according to Kabat numbering) of the light chain variable region having the amino acid sequence of SEQ ID NO: 23. In one embodiment, an anti-CD39 antibody of the disclosure comprises a VH comprising the Kabat CDR1, CDR2 and/or CDR3 of the heavy chain variable region having the amino acid sequence of SEQ ID NO: 22 and a VL comprising a Kabat CDR1, CDR2 and/or CDR3 of the light chain variable region having the amino acid sequence of SEQ ID NO: 23.

```
I-396 VH:
                                         (SEQ ID NO: 22)
EVQLQQSGAELVKPGASVKLSCIVSGFNIKDTYINWVKQRPEQGLEWIG

RIDPANGNTKYDPKFQGKATMTSDTSSNTAYLHLSSLTSDDSAVYYCAR

WGYDDEEADYFDSWGQGTTLTV

SS

I-396 VL:
                                         (SEQ ID NO: 23)
DIVLTQSPASLAVSLGQRATISCRASESVDNYGISFMNWFQQKPGQPG

PKLLIYAASNQGSVPARFSGSGSGTDFSLNILPMEEVDAAMYFCHQSKE

VPWTFGGGTKLEIK
```

An anti-CD39 antibody may for example comprise: a HCDR1 comprising an amino acid sequence: DTYIN (SEQ ID NO: 24), or a sequence of at least 4 contiguous amino acids thereof, optionally wherein one or more of these amino acids may be substituted by a different amino acid; a HCDR2 comprising an amino acid sequence: RIDPANGNTKYDPKFQG (SEQ ID NO: 25), or a sequence of at least 4, 5, 6, 7, 8, 9 or 10 contiguous amino acids thereof, optionally wherein one or more of these amino acids may be substituted by a different amino acid; a HCDR3 comprising an amino acid sequence: WGYDDEEADYFDS (SEQ ID NO: 26), or a sequence of at least 4, 5, 6, 7, 8, 9 or 10 contiguous amino acids thereof, optionally wherein one or more of these amino acids may be substituted by a different amino acid; a LCDR1 comprising an amino acid sequence: RASESVDNYGISFMN (SEQ ID NO: 27), or a sequence of at least 4, 5, 6, 7, 8, 9 or 10 contiguous amino acids thereof, optionally wherein one or more of these amino acids may be substituted by a different amino acid; a LCDR2 region comprising an amino acid sequence: AASNQGS (SEQ ID NO: 28) or a sequence of at least 4, 5 or 6 contiguous amino acids thereof, optionally wherein one or more of these amino acids may be substituted by a different amino acid; and/or a LCDR3 region of I-396 comprising an amino acid sequence: HQSKEVPWT (SEQ ID NO: 29), or a sequence of at least 4, 5, 6, 7 or 8 contiguous amino acids thereof, optionally wherein one or more of these amino acids may be deleted or substituted by a different amino acid. CDR positions may be according to Kabat numbering.

Another exemplary anti-CD39 VH and VL pair according to the disclosure is that of antibody I-399, the amino acid sequence of the heavy chain variable region of which is listed below (SEQ ID NO: 30), and the amino acid sequence of the light chain variable region of which is listed below (SEQ ID NO: 31). The CDRs according to Kabat numbering are underlined in SEQ ID NOS: 30 and 31. Optionally, the VH and VL comprise (e.g., are modified to incorporate) human acceptor frameworks. In one embodiment, an anti-CD39 antibody of the disclosure comprises the VH CDR1, CDR2 and/or CDR3 (e.g., according to Kabat numbering) of the heavy chain variable region having the amino acid sequence of SEQ ID NO: 30. In one embodiment, an anti-CD39 antibody of the disclosure comprise the VL CDR1, CDR2 and/or CDR3 (e.g., according to Kabat numbering) of the light chain variable region having the amino acid sequence of SEQ ID NO: 31. In one embodiment, an anti-CD39 antibody of the disclosure comprises a VH comprising the Kabat CDR1, CDR2 and/or CDR3 of the heavy chain variable region having the amino acid sequence of SEQ ID NO: 30 and a VL comprising a Kabat CDR1, CDR2 and/or CDR3 of the light chain variable region having the amino acid sequence of SEQ ID NO: 31.

I-399 VH:
(SEQ ID NO: 30)
PVQLQQPGAEVVMPGASVKLSCKASGYTFTSFWMNWMRQRPGQGLEW

IGEIDPSDFYTNSNQRFKGKATLTVDKSSSTAYMQLSSLTSEDSAVYFC

ARGDFGWYFDVWGTGTSVTSS

I-399 VL:
(SEQ ID NO: 31)
EIVLTQSPTTMTSSPGEKITFTCSASSSINSNYLHWYQQKPGFSPKLL

IYRTSNLASGVPTRFSGSGSGTSYSLTIGTMEAEDVATYYCQQGSSLPR

TFGGGTKLEIK

An anti-CD39 antibody may for example comprise: a HCDR1 comprising an amino acid sequence: SFWMN (SEQ ID NO: 32), or a sequence of at least 4 contiguous amino acids thereof, optionally wherein one or more of these amino acids may be substituted by a different amino acid; a HCDR2 comprising an amino acid sequence: EIDPSDFYTNSNQRFKG (SEQ ID NO: 33), or a sequence of at least 4, 5, 6, 7, 8, 9 or 10 contiguous amino acids thereof, optionally wherein one or more of these amino acids may be substituted by a different amino acid; a HCDR3 comprising an amino acid sequence: GDFGWYFDV (SEQ ID NO: 34), or a sequence of at least 4, 5 or 6 contiguous amino acids thereof, optionally wherein one or more of these amino acids may be substituted by a different amino acid; a LCDR1 comprising an amino acid sequence: SASSSINS-NYLH (SEQ ID NO: 35), or a sequence of at least 4, 5, 6, 7, 8, 9 or 10 contiguous amino acids thereof, optionally wherein one or more of these amino acids may be substituted by a different amino acid; a LCDR2 region comprising an amino acid sequence: RTSNLAS (SEQ ID NO: 36) or a sequence of at least 4, 5 or 6 contiguous amino acids thereof, optionally wherein one or more of these amino acids may be substituted by a different amino acid; and/or a LCDR3 region of I-399 comprising an amino acid sequence: QQGSSLPRT (SEQ ID NO: 37), or a sequence of at least 4, 5, 6, 7 or 8 contiguous amino acids thereof, optionally wherein one or more of these amino acids may be deleted or substituted by a different amino acid. CDR positions may be according to Kabat numbering.

In any of the I-394, I-395, I-396 and I-399 antibodies, the HCDR1, 2, 3 and LCDR1, 2, 3 sequences (each CDR independently, or all CDRs) can be specified as being being those of the Kabat numbering system, (as indicated in in the VH and VL sequences by underlining), those of the Chotia numbering system, or, those of the IMGT numbering system, or any other suitable numbering system.

In any aspect, the specified variable region, FR and/or CDR sequences may comprise one or more sequence modifications, e.g., a substitution (1, 2, 3, 4, 5, 6, 7, 8 or more sequence modifications). In one embodiment the substitution is a conservative modification.

In another aspect, the anti-CD39 compound comprises a $V_H$ domain having at least about 60%, 70% or 80% sequence identity, optionally at least about 85%, 90%, 95%, 97%, 98% or 99% identity, to the VH domain of SEQ ID NO: 6. In another aspect, the anti-CD39 antibody comprises a $V_L$ domain having at least about 60%, 70% or 80% sequence identity, optionally at least about 85%, 90%, 95%, 97%, 98% or 99% identity, to the VL domain of SEQ ID NO: 7.

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific (e.g., bispecific) antibodies formed from antibody fragments. Included, inter alia, are a nanobody, domain antibody, single domain antibody or a "dAb".

In certain embodiments, the DNA of a hybridoma producing an antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Optionally an antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for CD39 and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence. In this way, FR residues can be selected and combined from the consensus and import sequences so that the desired antibody characteristic is achieved.

Another method of making "humanized" monoclonal antibodies is to use a XenoMouse (Abgenix, Fremont, Calif.) as the mouse used for immunization. A XenoMouse is a murine host according that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection from antibody repertoires using phage display methods. Such techniques are known to the skilled person and can be implemented starting from monoclonal antibodies as disclosed in the present application.

An anti-CD39 antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g., freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment.

In a further embodiment, the formulation further comprises a pharmaceutically acceptable preservative. In a further embodiment, the formulation further comprises an isotonic agent. In a further embodiment, the formulation also comprises a chelating agent. In a further embodiment the formulation further comprises a stabilizer. In a further embodiment, the formulation further comprises a surfactant. For convenience reference is made to Remington: *The Science and Practice of Pharmacy*, 19<sup>th</sup> edition, 1995.

It is possible that other ingredients may be present in the peptide pharmaceutical formulation. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation.

Pharmaceutical compositions containing an antibody may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Diagnosis and Treatment of Disease

Methods of treating an individual, notably a human individual, using an anti-CD39 antibody as described herein are also provided for. In one embodiment, the disclosure provides for the use of an antibody as described herein in the preparation of a pharmaceutical composition for administration to a human patient. Typically, the individual suffers from, or is at risk for, cancer or an infectious disease (e.g., a viral infection, bacterial infection). In one embodiment, the individual has detectable soluble (extracellular) CD39 protein in circulation and/or in a tissue sample (e.g., a tumor or tumor-adjacent tissue sample).

For example, in one aspect, provided is a method of restoring or potentiating the activity of lymphocytes in an individual in need thereof, comprising the step of administering to said individual a neutralizing anti-CD39 antibody of the disclosure. The antibody can be for example a human or humanized anti-CD39 antibody that specifically binds and neutralizes the ATPase activity of soluble and membrane forms of "vascular" CD39 without binding CD39-L1, L2, L3 and/or L4, and which optionally is not substantially bound by human CD16 (and optionally further is not bound by other human Fcγ receptors such as CD32a, CD32b or CD64). Such antibodies will have reduced unwanted side effects or toxicity due to lack of binding at isoforms other than vascular CD39, and will have reduced unwanted side effects or toxicity resulting from depletion or other Fc-mediated effects on CD39-expressing endothelial cells in the vasculature.

In one embodiment, the method is directed at increasing the activity of lymphocytes (e.g., T cells) in an individual having a disease in which increased lymphocyte activity is beneficial or which is caused or characterized by immunosuppression, immunosuppressive cells, or, e.g., adenosine generated by CD4 T cells, CD8 T cells, B cells). The methods will be particularly useful for example to treat an individual having a solid tumor in which it is suspected the tumor microenvironment (and CD39-mediated adenosine production therein) may contribute to lack of recognition by the immune system (immune escape). The tumor environment (tumor tissue or tumor adjacent tissue) may, for example, be characterized by the presence of CD39-expressing immune cells, e.g., CD4 T cells, CD8 T cells, B cells.

More specifically, the methods and compositions are utilized for the treatment of a variety of cancers and other proliferative diseases, and infectious diseases. Because these methods operate by reducing adenosine that inhibits the anti-target cell (e.g., anti-tumor) activity of lymphocytes and possibly additionally by increasing ATP that can increase the anti-tumor activity of lymphocytes, they are applicable to a very broad range of cancers and infectious disease. In one embodiment, the anti-CD39 compositions are useful to treat cancer in individuals who are poor responders to (or not sensitive to) treatment with agent that neutralizes the inhibitory activity of human PD-1, e.g., that inhibits the interaction between PD-1 and PD-L1. Representative examples of cancers that can be treated include in particular solid tumors in which adenosine in the tumor microenvironment may play a strong role in suppressing the anti-tumor immune response. In one embodiment, a human patient treated with an anti-CD39 antibody has liver cancer, bone cancer, pancreatic cancer, skin cancer, cancer of the head or neck, including head and neck squamous cell carcinoma (HNSCC), breast cancer, lung cancer, non-small cell lung cancer (NSCLC), castrate resistant prostate cancer (CRPC), melanoma, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present disclosure is also applicable to treatment of metastatic cancers. Patients can be tested or selected for one or more of the above described clinical attributes prior to, during or after treatment.

In one embodiment the anti-CD39 antibody is used in the treatment of a cancer characterized detectable and/or elevated levels of soluble (extracellular) CD39 protein, e.g., in circulation and/or in tissues, for example in tumor or tumor adjacent tissue.

In one embodiment the anti-CD39 antibody is used in the treatment of a cancer characterized by malignant cells expressing CD39.

In one embodiment, the anti-CD39 antibody is administered in an amount effective to achieve and/or maintain in an individual (e.g., for 1, 2, 3, 4 weeks, and/or until the subsequent administration of antigen binding compound) a blood concentration of at least the $EC_{50}$, optionally the $EC_{70}$, optionally substantially the $EC_{100}$, for neutralization of the enzymatic activity of CD39, optionally sCD39, optionally memCD39. In one embodiment, the active amount of anti-CD39 antibody is an amount effective to achieve the $EC_{50}$, optionally the $EC_{70}$, optionally substantially the $EC_{100}$, for neutralization of the enzymatic activity of CD39, optionally sCD39, optionally memCD39, in an extravascular tissue of an individual. In one embodiment, the active amount of anti-CD39 antibody is an amount effective to achieve (or maintain) in an individual the $EC_{50}$, optionally the $EC_{70}$, optionally substantially the $EC_{100}$, for inhibition of neutralize the enzymatic activity of CD39, optionally sCD39, optionally memCD39.

Optionally, in one embodiment, in contrast to some antibodies that are directed to the depletion of CD39-expressing tumor cells by ADCC (which, e.g., can provide full efficacy at concentrations equal or substantially lower than that which provides receptor saturation), the anti-CD39 antibody does not exhibit substantial Fcγ receptor-mediated activity and is administered in an amount effective to neutralize the enzymatic activity of, optionally further CD39, without substantially causing down-modulation of CD39 expression, for a desired period of time, e.g., 1 week, 2 weeks, a month, until the next successive administration of anti-CD39 antibody.

In one embodiment, the anti-CD39 antibody is administered in an amount effective to achieve and/or maintain (e.g., for 1, 2, 3, 4 weeks, and/or until the subsequent administration of anti-CD39 antibody) in an individual a blood concentration of at least the $EC_{50}$, optionally the $EC_{70}$, optionally substantially the $EC_{100}$, for inhibition of CD39-mediated catabolism of ATP to AMP (e.g., by assessing neutralization of ATPase activity of sCD39; by assessing neutralization of ATPase activity of soluble (extracellular) CD39 protein, see Example 5).

In one embodiment, provided is a method for treating or preventing cancer in an individual, the method comprising administering to an individual having disease an anti-CD39 antibody in an amount that achieves or maintains for a specified period of time a concentration in circulation, optionally in an extravascular tissue of interest (e.g., the tumor or tumor environment), that is higher than the concentration required for 50%, 70%, or full (e.g., 90%) receptor saturation CD39-expressing cells in circulation (for example as assessed in PBMC). Optionally the concentration achieved is at least 20%, 50% or 100% higher than the concentration required for the specified receptor saturation.

In one embodiment, provided is a method for treating or preventing cancer in an individual, the method comprising administering to the individual an anti-CD39 antibody in an amount that achieves or maintains for a specified period of time a concentration in circulation, optionally in an extravascular tissue of interest (e.g., the tumor or tumor environment), that is higher than the $EC_{50}$, optionally $EC_{70}$ or optionally $EC_{100}$, for binding to CD39-expressing cells (e.g., as assessed by flow cytometry, by titrating anti-CD39 antibody on CD39-expressing cells, for example Ramos cells as in Examples, Methods). Optionally the concentration achieved is at least 20%, 50% or 100% higher than the $EC_{50}$, optionally $EC_{70}$ or optionally $EC_{100}$, for binding to CD39-expressing cells.

The $EC_{50}$, $EC_{70}$ or the $EC_{100}$ can be assessed for example in a cellular assay for neutralization of the enzymatic activity of CD39 as shown in the Examples herein, e.g., neutralization of ATPase activity in B cells by quantifying hydrolysis of ATP to AMP (or ATP to downstream adenosine), see Examples, Methods. "$EC_{50}$" with respect to neutralization of the enzymatic activity of CD39, refers to the efficient concentration of anti-CD39 antibody which produces 50% of its maximum response or effect with respect to neutralization of the enzymatic activity. "$EC_{70}$" with respect to neutralization of the enzymatic activity of CD39, refers to the efficient concentration of anti-CD39 antibody which produces 70% of its maximum response or effect. "$EC_{100}$" with respect to neutralization of the enzymatic activity of CD39, refers to the efficient concentration of anti-CD39 antibody which produces its substantially maximum response or effect with respect to such neutralization of the enzymatic activity.

In some embodiments, particularly for the treatment of solid tumors, the concentration achieved is designed to lead to a concentration in tissues (outside of the vasculature, e.g., in the tumor or tumor environment) that corresponds to at least the $EC_{50}$ or $EC_{70}$ for neutralization of the enzymatic activity, optionally at about, or at least about, the $EC_{100}$.

In one embodiment, the amount of anti-CD39 antibody is between 1 and 20 mg/kg body weight. In one embodiment, the amount is administered to an individual weekly, every two weeks, monthly or every two months.

In one embodiment provided is a method of treating a human individual having a cancer, comprising administering to the individual an effective amount of an anti-CD39 antibody of the disclosure for at least one administration cycle (optionally at least 2, 3, 4 or more administration cycles), wherein the cycle is a period of eight weeks or less, wherein for each of the at least one cycles, one, two, three or four doses of the anti-CD39 antibody are administered at a dose of 1-20 mg/kg body weight. In one embodiment, the anti-CD39 antibody is administered by intravenous infusion.

Suitable treatment protocols for treating a human include, for example, administering to the patient an amount as disclosed herein of an anti-CD39 antibody, wherein the method comprises at least one administration cycle in which at least one dose of the anti-CD39 antibody is administered. Optionally, at least 2, 3, 4, 5, 6, 7 or 8 doses of the anti-CD39 antibody are administered. In one embodiment, the administration cycle is between 2 weeks and 8 weeks.

In one embodiment, provided is a method for treating or preventing a disease (e.g., a cancer, a solid tumor, a hematological tumor) in an individual, the method comprising administering to an individual having disease (e.g., a cancer, a solid tumor, a hematological tumor) an anti-CD39 antibody that neutralizes the enzymatic activity of CD39 for at least one administration cycle, the administration cycle comprising at least a first and second (and optionally a 3$^{rd}$, 4$^{th}$, 5$^{th}$, 6$^{th}$, 7$^{th}$ and/or 8$^{th}$ or further) administration of the anti-CD39 antibody, wherein the anti-CD39 antibody is administered in an amount effective to achieve, or to maintain between two successive administrations, a blood (serum) concentration of anti-CD39 antibody of at least 0.1 µg/ml, optionally at least 0.2 µg/ml, optionally at least 1 µg/ml, or optionally at least 2 µg/ml (e.g., for treatment of a hematological tumor), or optionally at least about 1 µg/ml, 2 µg/ml, 10 µg/ml, or 20 µg/ml, e.g., between 1-100 µg/ml, 1-50 µg/ml, 1-20 µg/ml, or 1-10 µg/ml (e.g., for treatment of a solid tumor, for treatment of a hematological tumor). In one embodiment, a specified continuous blood concentration is maintained, wherein the blood concentration does not drop substantially below the specified blood concentration for the duration of the specified time period (e.g., between two administrations of antibody, number of weeks, 1 week, 2 weeks, 3 weeks, 4 weeks), i.e. although the blood concentration can vary during the specified time period, the specified blood concentration maintained represents a minimum or "trough" concentration. In one embodiment, a therapeutically active amount of an anti-CD39 antibody is an amount of such antibody capable of providing (at least) the $EC_{50}$ concentration, optionally the $EC_{70}$ concentration optionally the $EC_{100}$ concentration, in blood and/or in a tissue for neutralization of the enzymatic activity of CD39 for a period of at least about 1 week, about 2 weeks, or about one month, following administration of the antibody.

Prior to or during a course of treatment with an anti-CD39 antibody of the disclosure, presence or levels or soluble (extracellular) CD39 protein, CD39-expressing cells, adenosine, ATP, ADP and/or AMP levels can be assessed within and/or adjacent to a patient's tumor to assess whether the patient is suitable for treatment (e.g., to predict whether the patient is likely to respond to treatment). Increased presence or levels or soluble (extracellular) CD39, CD39-expressing cells, levels of adenosine, ATP, ADP and/or AMP may indicate an individual is suitable for treatment with (e.g., likely to benefit from) an anti-CD39 antibody of the disclosure (including but not limited to an antibody that inhibits substrate-bound CD39).

Prior to or during a course of treatment with an anti-CD39 antibody of the disclosure, adenosine, ADP and/or AMP levels can optionally also be assessed within and/or adjacent to a patient's tumor to assess whether the patient is benefitting from treatment with an anti-CD39 antibody. Decreased levels of adenosine, ATP, ADP and/or AMP compared following an administration (or dosing of antibody) compared to levels prior to treatment (or dosing of antibody) may indicate an individual is benefitting from treatment with an anti-CD39 antibody of the disclosure (including but not limited to an antibody that inhibits substrate-bound CD39). Optionally, if a patient is benefitting from treatment with the anti-CD39 antibody, methods can further comprise administering a further dose of the anti-CD39 antibody to the patient (e.g., continuing treatment).

In one embodiment, assessing adenosine, ADP and/or AMP levels within and/or adjacent to a patient's tumor the tissue sample comprises obtaining from the patient a biological sample of a human tissue selected from the group consisting of tissue from a cancer patient, e.g., cancer tissue, tissue proximal to or at the periphery of a cancer, cancer adjacent tissue, adjacent non-tumorous tissue or normal adjacent tissue, and detecting adenosine, ATP, ADP and/or AMP levels within the tissue. The levels from the patient can be comparing the level to a reference level, e.g., corresponding to a healthy individual.

In one embodiment, the disclosure provides a method for the treatment or prevention of a cancer in an individual in need thereof, the method comprising:
a) detecting soluble (extracellular) CD39 protein and/or CD39-expressing cells in circulation or in the tumor environment, optionally within the tumor and/or within adjacent tissue, and
b) upon a determination that soluble (extracellular) CD39 protein and/or CD39-expressing cells are comprised in circulation or the tumor environment, optionally at a level that is increased compared to a reference level (e.g., corresponding to a healthy individual or an individual not deriving substantial benefit from an anti-CD39 antibody), administering to the individual an anti-CD39 antibody. The CD39-expressing cells may comprise tumor cells or leukocytes, for example circulating or tumor infiltrating cells, for example CD4 T cells, CD8 T cells, TReg cells, B cells.

In one embodiment, the disclosure provides a method for the treatment or prevention of a cancer in an individual in need thereof, the method comprising:
a) assessing whether the individual has detectable soluble (extracellular) CD39, optionally in circulation, optionally within the tumor and/or within adjacent tissue, and
b) upon a detection of soluble (extracellular) CD39, optionally at a level that is increased compared to a reference level (e.g., corresponding to a healthy individual or an individual not deriving substantial benefit from an anti-CD39 antibody of the disclosure), administering to the individual an anti-CD39 antibody of the disclosure.

Optionally, in any of the methods, detecting soluble CD39 protein and/or CD39-expressing cells (or adenosine, ATP, ADP and/or AMP) within the tumor environment comprises obtaining from the individual a biological sample that comprises cancer tissue and/or tissue proximal to or at the periphery of a cancer (e.g., cancer adjacent tissue, adjacent non-tumorous tissue or normal adjacent tissue), and detecting levels of sCD39 protein, CD39-expressing cells (or adenosine, ATP, ADP and/or AMP). CD39-expressing cells may comprise, for example, tumor cells, CD4 T cells, CD8 T cells, TReg cells, B cells.

An individual having a cancer can be treated with the anti-CD39 antibody with our without a prior detection step to assess presence of sCD39 and/or expression of CD39 on circulating cells or on cells in the tumor microenvironment (e.g., on tumor cells, CD4 T cells, CD8 T cells, TReg cells, B cells). Optionally, the treatment method can comprise a step of detecting a CD39 nucleic acid or polypeptide in a biological sample from blood or of a tumor from an individual (e.g., in cancer tissue, tissue proximal to or at the periphery of a cancer, cancer adjacent tissue, adjacent non-tumorous tissue or normal adjacent tissue). A determination that a biological sample comprises cells expressing CD39 (e.g., prominently expressing; expressing CD39 at a high level, high intensity of staining with an anti-CD39 antibody, compared to a reference) indicates that the patient has a cancer that may have a strong benefit from treatment with an agent that inhibits CD39. In one embodiment, the method comprises determining the level of expression of a CD39 nucleic acid or polypeptide in a biological sample and comparing the level to a reference level corresponding to a healthy individual. A determination that a biological sample comprises sCD39 protein and/or cells expressing CD39 nucleic acid or polypeptide at a level that is increased compared to the reference level indicates that the patient has a cancer that can be advantageously treated with an anti-CD39 antibody of the disclosure. In one embodiment, detecting a CD39 polypeptide in a biological sample comprises detecting soluble extracellular CD39 protein. In one embodiment, detecting a CD39 polypeptide in a biological sample comprises detecting CD39 polypeptide expressed on the surface of a malignant cell, a CD4 T cell, CD8 T cell, TReg cell, B cell. In one embodiment, a determination that a biological sample comprises cells that prominently expresses CD39 nucleic acid or polypeptide indicates that the patients has a cancer that can be advantageously treated with an anti-CD39 antibody of the disclosure. "Prominently expressed", when referring to a CD39 polypeptide, means that the CD39 polypeptide is expressed in a substantial number of cells taken from a given patient. While the definition of the term "prominently expressed" is not bound by a precise percentage value, in some examples a receptor said to be "prominently expressed" will be present on at least 10%, 20% 30%, 40%, 50%, 60%, 70%, 80%, or more of the tumor cells taken from a patient.

Determining whether an individual has a cancer characterized by cells that express a CD39 polypeptide can for example comprise obtaining a biological sample (e.g., by performing a biopsy) from the individual that comprises cells from the cancer environment (e.g., tumor or tumor adjacent tissue), bringing said cells into contact with an antibody that binds an CD39 polypeptide, and detecting whether the cells express CD39 on their surface. Optionally, determining whether an individual has cells that express CD39 comprises conducting an immunohistochemistry assay.

The antibody compositions may be used in as monotherapy or combined treatments with one or more other therapeutic agents, including agents normally utilized for the particular therapeutic purpose for which the antibody is being administered. The additional therapeutic agent will normally be administered in amounts and treatment regimens typically used for that agent in a monotherapy for the particular disease or condition being treated. Such therapeutic agents include, but are not limited to anti-cancer agents and chemotherapeutic agents, e.g. chemotherapeutic agent capable of causing extracellular release of ATP from tumor cells.

In one embodiment, the anti-CD39 neutralizing antibodies lack binding to human CD16 yet potentiate the activity of CD16-expressing effector cells (e.g., NK or effector T cells). Accordingly, in one embodiment, the second or additional second therapeutic agent is an antibody or other Fc domain-containing protein capable of inducing ADCC toward a cell to which it is bound, e.g., via CD16 expressed by an NK cell. Typically, such antibody or other protein will comprise a domain that binds to an antigen of interest, e.g., an antigen present on a tumor cell (tumor antigen), and an Fc domain or portion thereof, and will exhibit binding to the antigen via the antigen binding domain and to Fcγ receptors (e.g., CD16) via the Fc domain. In one embodiment, its ADCC activity will be mediated at least in part by CD16. In one embodiment, the additional therapeutic agent is an antibody having a native or modified human Fc domain, for example a Fc domain from a human IgG1 or IgG3 antibody. The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils. The term "ADCC-inducing antibody" refers to an antibody that demonstrates ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody. Examples of antibodies that induce ADCC include rituximab (for the treatment of lymphomas, CLL, trastuzumab (for the treatment of breast cancer), alemtuzumab (for the treatment of chronic lymphocytic leukemia) and cetuximab (for the treatment of colorectal cancer, head and neck squamous cell carcinoma). Examples of ADCC-enhanced antibodies include but are not limited to: GA-101 (hypofucosylated anti-CD20), margetuximab (Fc enhanced anti-HER2), mepolizumab, MEDI-551 (Fc engineered anti-CD19), obinutuzumab (glyco-engineered/hypofucosuylated anti-CD20), ocaratuzumab (Fc engineered anti-CD20), XmAb® 5574/MOR208 (Fc engineered anti-CD19).

In one embodiment, the anti-CD39 neutralizing antibodies augment the efficacy of agents that neutralizes the inhibitory activity of human PD-1, e.g., that inhibits the interaction between PD-1 and PD-L1, notably in individuals who are poor responders to (or not sensitive to) treatment with agent that neutralizes the inhibitory activity of human PD-1. Accordingly, in one embodiment, the second or additional second therapeutic agent is an antibody or other agent that neutralizes the inhibitory activity of human PD-1.

Programmed Death 1 (PD-1) (also referred to as "Programmed Cell Death 1") is an inhibitory member of the CD28 family of receptors. The complete human PD-1 sequence can be found under GenBank Accession No. U64863. Inhibition or neutralization the inhibitory activity of PD-1 can involve use of a polypeptide agent (e.g., an antibody, a polypeptide fused to an Fc domain, an immunoadhesin, etc.) that prevents PD-L1-induced PD-1 signalling. There are currently at least six agents blocking the PD-1/PD-L1 pathway that are marketed or in clinical evaluation. One agent is BMS-936558 (Nivolumab/ONO-4538, Bristol-Myers Squibb; formerly MDX-1106). Nivolumab, (Trade name Opdivo®) is an FDA-approved fully human IgG4 anti-PD-L1 mAb that inhibits the binding of the PD-L1 ligand to both PD-1 and CD80 and is described as antibody 5C4 in WO 2006/121168, the disclosure of which is incorporated herein by reference. For melanoma patients, the most significant OR was observed at a dose of 3 mg/kg, while for other cancer types it was at 10 mg/kg. Nivolumab is generally dosed at 10 mg/kg every 3 weeks until cancer progression. The terms "reduces the inhibitory activity of human PD-1", "neutralizes PD-1" or "neutralizes the inhibitory activity of human PD-1" refers to a process in which PD-1 is inhibited in its signal transduction capacity resulting from the interaction of PD-1 with one or more of its binding partners, such as PD-L1 or PD-L2. An agent that neutralizes the inhibitory activity of PD-1 decreases, blocks, inhibits, abrogates or interferes with signal transduction resulting from the interaction of PD-1 with one or more of its binding partners, such as PD-L1, PD-L2. Such an agent can thereby reduce the negative co-stimulatory signal mediated by or through cell surface proteins expressed on T lymphocytes, so as to enhance T-cell effector functions such as proliferation, cytokine production and/or cytotoxicity.

MK-3475 (human IgG4 anti-PD1 mAb from Merck), also referred to as lambrolizumab or pembrolizumab (Trade name Keytruda®) has been approved by the FDA for the treatment of melanoma and is being tested in other cancers.

Pembrolizumab was tested at 2 mg/kg or 10 mg/kg every 2 or 3 weeks until disease progression. MK-3475, also known as Merck 3745 or SCH-900475, is also described in WO2009/114335. MPDL3280A/RG7446 (atezolizumab, trade name Tecentriq™, anti-PD-L1 from Roche/Genentech) is a human anti-PD-L1 mAb that contains an engineered Fc domain designed to optimize efficacy and safety by minimizing FcγR binding and consequential antibody-dependent cellular cytotoxicity (ADCC). Doses of 51, 10, 15, and 25 mg/kg MPDL3280A were administered every 3 weeks for up to 1 year. In phase 3 trial, MPDL3280A is administered at 1200 mg by intravenous infusion every three weeks in NSCLC.

AMP-224 (Amplimmune and GSK) is an immunoadhesin comprising a PD-L2 extracellular domain fused to an Fc domain. Other examples of agents that neutralize PD-1 may include an antibody that binds PD-L2 (an anti-PD-L2 antibody) and blocks the interaction between PD-1 and PD-L2.

Pidlizumab (CT-011; CureTech) (humanized IgG1 anti-PD1 mAb from CureTech/Teva), Pidlizumab (CT-011; CureTech) (see e.g., WO2009/101611) is another example; the agent was tested in thirty patients with rituximab-sensitive relapsed FL were treated with 3 mg/kg intravenous CT-011 every 4 weeks for 4 infusions in combination with rituximab dosed at 375 mg/m2 weekly for 4 weeks, starting 2 weeks after the first infusion of CT-011.

Further known PD-1 antibodies and other PD-1 inhibitors include AMP-224 (a B7-DC/IgG1 fusion protein licensed to GSK), AMP-514 described in WO 2012/145493, antibody MEDI-4736 (durvalumab, trade name Imfinzi™, an anti-PD-L1 developed by AstraZeneca/Medimmune) described in WO2011/066389 and US2013/034559, antibody YW243.55.570 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/014708, WO2009/114335 and WO2013/019906, the disclosures of which are hereby incorporated by reference. Further examples of anti-PD1 antibodies are disclosed in WO2015/085847 (Shanghai Hengrui Pharmaceutical Co. Ltd.), for example antibodies having light chain variable domain CDR1, 2 and 3 of SEQ ID NO: 6, SEQ ID NO: 7 and/or SEQ ID NO: 8, respectively, and antibody heavy chain variable domain CDR1, 2 and 3 of SEQ ID NO: 3, SEQ ID NO: 4 or SEQ ID NO: 5, respectively, wherein the SEQ ID NO references are the numbering according to WO2015/085847, the disclosure of which is incorporated herein by reference. Antibodies that compete with any of these antibodies for binding to PD-1 or PD-L1 also can be used. An exemplary anti-PD-1 antibody is pembrolizumab (commercialized by Merck & Co. as Keytruda™, see, also WO 2009/114335 the disclosure of which is incorporated herein by reference).

In some embodiments, the PD-1 neutralizing agent is an anti-PD-L1 mAb that inhibits the binding of PD-L1 to PD-1. In some embodiments, the PD-1 neutralizing agent is an anti-PD1 mAb that inhibits the binding of PD-1 to PD-L1. In some embodiments, the PD-1 neutralizing agent is an immunoadhesin (e.g., an immunoadhesin comprising an extracellular or PD-1 binding portion of PD-L1 or PD-L2 fused to a constant region (e.g., an Fc region of an immunoglobulin sequence).

In the treatment methods, the CD39-binding compound and the second therapeutic agent can be administered separately, together or sequentially, or in a cocktail. In some embodiments, the antigen-binding compound is administered prior to the administration of the second therapeutic agent. For example, the CD39-binding compound can be administered approximately 0 to 30 days prior to the administration of the second therapeutic agent. In some embodiments, an CD39-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, a CD39-binding compound is administered concurrently with the administration of the therapeutic agents. In some embodiments, a CD39-binding compound is administered after the administration of the second therapeutic agent. For example, a CD39-binding compound can be administered approximately 0 to 30 days after the administration of the second therapeutic agent. In some embodiments, a CD39-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

EXAMPLES

Methods

Generation of CD39 Mutants

CD39 mutants were generated by PCR. The sequences amplified were run on agarose gel and purified using the Macherey Nagel PCR Clean-Up Gel Extraction kit (reference 740609). The purified PCR products generated for each mutant were then ligated into an expression vector, with the ClonTech InFusion system. The vectors containing the mutated sequences were prepared as Miniprep and sequenced. After sequencing, the vectors containing the mutated sequences were prepared as Midiprep using the Promega PureYield™ Plasmid Midiprep System. HEK293T cells were grown in DMEM medium (Invitrogen), transfected with vectors using Invitrogen's Lipofectamine 2000 and incubated at 37° C. in a CO2 incubator for 48 hours prior to testing for transgene expression. Mutants were transfected in Hek-293T cells, as shown in the table below. The targeted amino acid mutations in the table 1 below are shown using numbering of SEQ ID NO: 1.

TABLE 1

| Mutant | Substitutions | | | | |
|---|---|---|---|---|---|
| 1 | V77G | H79Q | Q444K | G445D | |
| 2A | V81S | E82A | R111A | V115A | |
| 2B | E110A | R113T | E114A | | |
| 3 | R118A | S119A | Q120K | Q122H | E123A |
| 4 | D150A | E153S | R154A | S157K | N158A | L278F |
| 5 | Q96A | N99A | E143A | R147E | |
| 6 | K188R | Replacement of the residues 190 to 207 by KTPGGS | | | |
| 7 | A273S | N275A | I277S | R279A | |
| 8 | S294A | K298G | K303A | E306A | T308K | Q312A |
| 9 | K288E | K289A | V290A | E315R | |
| 10A | Q354A | D356S | E435A | H436Q | |
| 10B | H428A | T430A | A431D | D432A | |
| 11 | N371K | L372K | E375A | K376G | Insertion377V | V377S |
| 12 | K388N | Q392K | P393S | E396A | |
| 13 | A402P | G403A | K405A | E406A | |
| 15 | K87A | E100A | D107A | | |
| 16 | Q323A | Q324A | Q327A | E331K | |
| 17 | N334A | S336A | Y337G | N346A | |
| 18 | Q228A | I230S | D234A | Q238A | |
| 19 | R138A | M139A | E142K | | |

Cloning, Production and Purification of Soluble huCD39
Molecular Biology

The huCD39 protein was cloned from human PBMC cDNA using the following primers TACGACT-CACAAGCTTGCCGCCACCATGGAAGATA-CAAAGGAGTC (SEQ ID NO: 42) (Forward), and CCGCCCCGACTCTAGATCACTTGTCATCGT-CATCTTTGTAATCGA CATAGGTGGAGTGGGAGAG (SEQ ID NO: 43) (Reverse). The purified PCR product was then cloned into an expression vector using the InFusion cloning system. A M2 tag (FLAG tag, underlined in SEQ ID NO: 45) was added in the C-terminal part of the protein for the purification step; it will be appreciated that a CD39 extracellular domain protein (e.g., of SEQ ID NO: 45) can in any embodiment optionally be specified to lack the M2 tag.

Expression and Purification of the huCD39 Proteins

After validation of the sequence cloned, CHO cells were nucleofected and the producing pool was then sub-cloned to obtain a cell clone producing the huCD39 protein. Supernatant from the huCD39 clone grown in roller was harvested and purified using M2 chromatography column and eluted using the M2 peptide. The purified proteins were then loaded onto a S200 size exclusion chromatography column. The purified protein corresponding to a monomer was formulated in a TBS PH7.5 buffer. The amino acid sequence of the CD39-M2 extracellular domain recombinant protein without M2 tag was as follows:

(SEQ ID NO: 44)
MEDTKESNVKTFCSKNILAILGFSSIIAVIALLAVGLTQNKALPENVKY

GIVLDAGSSHTSLYIYKWPAEKENDTGVVHQVEECRVKGPGISKFVQKV

NEIGIYLTDCMERAREVIPRSQHQETPVYLGATAGMRLLRMESEELADR

VLDVVERSLSNYPFDFQGARIITGQEEGAYGWITINYLLGKFSQKTRWF

SIVPYETNNQETFGALDLGGASTQVTFVPQNQTIESPDNALQFRLYGKD

YNVYTHSFLCYGKDQALWQKLAKDIQVASNEILRDPCFHPGYKKVVNVS

DLYKTPCTKRFEMTLPFQQFEIQGIGNYQQCHQSILELFNTSYCPYSQC

AFNGIFLPPLQGDFGAFSAFYFVMKFLNLTSEKVSQEKVTEMMKKFCAQ

PWEEIKTSYAGVKEKYLSEYCFSGTYILSLLLQGYHFTADSWEHIHFIG

KIQGSDAGWTLGYMLNLTNMIPAEQPLSTPLSHSTYV.

Inhibition of the Enzymatic Activity of Soluble CD39

The inhibition by antibodies of the enzymatic activity of soluble CD39 protein produced was evaluated using Cell Titer Glo™ (Promega, reference G7571) that allows assessment of ATP hydrolysis through use of a reagent that generates a luminescent signal proportional to the amount of ATP present. In this way, inhibition of the soluble-CD39-meidatd ATP hydrolysis can be assessed. Briefly, dose ranges of anti-CD39 antibodies from 100 μg/ml to 6×10$^{-3}$ μg/ml were incubated with 400 ng/ml of soluble recombinant human CD39 protein having the amino acid sequence described in the Methods section (SEQ ID NO: 45), for 1 h at 37° C. 20 μM ATP was added to the plates for 30 additional minutes at 37° C. before addition of CTG (Cell Titer Glo) reagent. Emitted light was quantified using an Enspire™ luminometer after a short incubation period of 5 min in the dark. Anti-CD39 antibody efficacy was determined by comparing emitted light in presence of antibody with ATP alone (maximal light emission) and ATP together with soluble CD39 protein (minimal light emission).

Inhibition of the Enzymatic Activity of Cellular CD39

The inhibition of the CD39 enzymatic activity in CD39-expressing cells by antibodies was evaluated using Cell Titer Glo™ (Promega, reference G7571) that allows assessment of ATP hydrolysis through use of a reagent that generates a luminescent signal proportional to the amount of ATP present. The assay was thus designed to permit assessment of the inhibition of ATP hydrolyzed by CD39 in the cell culture supernatant. Briefly, 5×10$^4$ Ramos human lymphoma cells, 5×10$^3$ human CD39-, cynomolgus CD39- and mouse CD39-expressing CHO cells, were incubated 1 hour at 37° C. with anti-CD39 antibodies from 30 μg/ml to 5×10 μg/ml. Cells were then incubated with 20 μM ATP for 1 additional hour at 37° C. Plates were centrifuged for 2 min at 400 g and 50 μl cell supernatant are transferred in a luminescence microplate (white wells). 50 μl CellTiter-Glo® Reagent (CTG) was added to the supernatant and emitted light was quantified after a 5 min incubation in the dark using a Enspire™ luminometer. Anti-CD39 antibody efficacy was determined by comparing emitted light in presence of antibody with ATP alone (maximal light emission) and ATP together with cells (minimal light emission).

Generation of Antibodies: Immunization and Screening in Mice

To obtain anti-human CD39 antibodies, Balb/c mice were immunized with the recombinant human CD39-M2 extracellular domain recombinant protein described above. Mice received one primo-immunization with an emulsion of 50 μg CD39 protein and Complete Freund Adjuvant, intraperitoneally, a 2nd immunization with an emulsion of 50 μg CD39 protein and Incomplete Freund Adjuvant, intraperitoneally, and finally a boost with 10 μg CD39 protein, intravenously. Immune spleen cells were fused 3 days after the boost with X63.Ag8.653 immortalized B cells, and cultured in the presence of irradiated spleen cells. Hydridomas were plated in semi-solid methylcellulose-containing medium and growing clones were picked using a clonepix 2 apparatus (Molecular Devices).

Example 1: Epitope Mapping of Known Neutralizing CD39 mAbs

In order to gain insight into how antibodies that are able to inhibit the enzymatic (ATPase) activity of cellular CD39, we investigated the epitopes bound by antibodies that have been reported to inhibit the ATPase activity of CD39 in cellular assays: BY40 disclosed in PCT publication no. WO2009/095478.

In order to define the epitopes of anti-CD39 antibodies, we designed CD39 mutants defined by substitutions of amino acids exposed at the molecular surface over the surface of CD39. Mutants were transfected in Hek-293T cells, as shown in the table 1, using numbering of SEQ ID NO: 1.

Dose-ranges of I-394 (10-2.5-0.625-0.1563-0.0391-0.0098-0.0024-0.0006 μg/ml) are tested on the 20 generated mutants by flow cytometry. BY40 antibodies both had complete loss of binding to cells expressing mutant 5 of CD39, without loss of binding to any other mutant. Mutant 5 contains amino acid substitutions at residues Q96, N99, E143 and R147. The position of Mutant 5 on the surface of CD39 is shown in FIG. 3A.

Example 2: Known Neutralizing CD39 mAbs are Unable to Inhibit the ATPase Activity of Recombinant Soluble CD39 Protein The two antibodies that have been reported to inhibit the ATPase activity of CD39 in cellular assays (BY40 and BY12) were assessed to determine whether are able to inhibit the ATPase activity of recombinant soluble CD39 protein. The inhibition by antibodies of the enzymatic activity of soluble CD39 protein produced as described above was evaluated using Cell Titer Glo™ (Promega, reference G7571). The inhibition by antibodies of of the enzymatic activity of cellular CD39 protein was evaluated as indicated above.

Figure 2B:
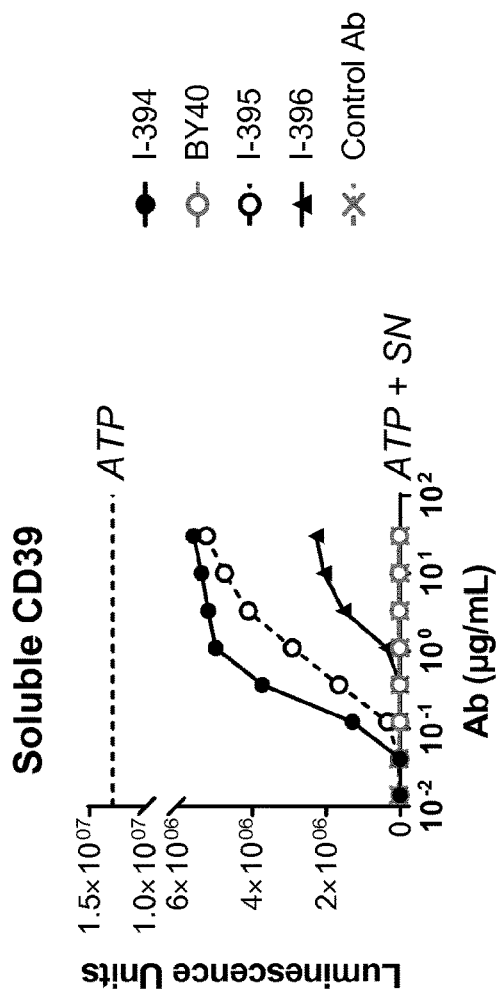
FIG. 2B shows that antibodies I-395 and I-396 both inhibit soluble CD39 in comparison to negative control (BY40) and positive control (I-394) antibodies.

As expected, BY40 inhibited the ATPase activity of CD39 protein in cells. However, BY40 was unable to inhibit the enzymatic activity of soluble CD39 protein. FIG. 2B shows a comparison of BY40 with the new antibodies identified herein.

Example 3: Screening for New mAbs to Block sCD39 Activity

A series of immunizations were carried out in order to seek antibodies that neutralize the ATPase activity of sCD39. To obtain anti-human CD39 antibodies, animals were immunized with the recombinant human CD39-M2 extracellular domain recombinant protein described above. In total, 15 series of immunizations were carried out using different protocols and in different animals. Included were different mice strains, rats and rabbits.

In initial immunization protocols, the primary screen involved testing supernatant (SN) of growing clones by flow cytometry using wild type CHO and CHO expressing huCD39 cell lines. Cells were stained with 0.1 µM and 0.005 µM CFSE, respectively. For the flow cytometry screening, all cells were equally mixed and the presence of reacting antibodies in supernatants was revealed by Goat anti-mouse polyclonal antibody (pAb) labeled with APC. For antibodies that bound huCD39, supernatants were then screened for inhibition of the enzymatic activity of soluble CD39 using the screening assay developed and described above (Methods).

Results showed that while numerous specific CD39-binding antibodies could be obtained, none of the antibodies from any of these immunizations showed any inhibition of the enzymatic activity of soluble CD39. One possibility is that dominant epitopes on CD39 do not include epitope suitably positioned at or near that catalytic site of CD39. In view of the few antibodies available that inhibit cellular CD39 and the known difficulties in inhibiting the catalytic sites of enzymes using antibodies, the absence of antibodies that neutralize sCD39 may indicate that it is not possible to obtain antibodies that inhibit soluble (extracellular domain) CD39. Other possibilities relate to non-functional screening assays and/or improperly folded or functioning soluble CD39 protein, particularly since the lack of any antibody that can inhibit soluble CD39 hampers validation of sCD39 blockade assays.

In view of the absence of antibodies able to inhibit soluble CD39, a further immunization was carried out with a screening protocol designed to favor the generation of antibodies that bind the active site of CD39 as identified by the epitope of antibody BY40. Briefly, the primary screen involved testing supernatant (SN) of growing clones by flow cytometry using wild type CHO and CHO expressing huCD39 cell lines, as in the preceding immunizations, followed by screening for loss of binding Hek-293T cells expressing CD39 mutant 5, compared to wild-type CD39, as shown in Table 1. Mutant 5 has substitutions at residues Q96, N99, E143 and R147. However, again results showed that while numerous specific CD39-binding antibodies could be obtained that showed loss of binding to mutant 5, none of the antibodies from any of the initial immunizations showed any inhibition of the enzymatic activity of soluble CD39.

Example 4: Identification of a First Antibody that Inhibits sCD39 Activity as Part of an Epitope-Directed Screen We sought to identify anti-CD39 antibodies that do not bind the Q96, N99, E143 and R147 region (defined by mutant 5) in order to have antibodies that do not compete with BY40-like antibodies. Such antibodies which need not have any ability to block the ATPase activity of CD39 can be useful for pharmacology studies of antibodies that inhibit cellular CD39 which bind to the BY40 binding site, e.g., to detect and quantify free CD39 proteins on cells in the presence of BY40 or BY40-like antibodies that inhibit cellular CD39.

Starting from the results of the immunization of Example 3 in which hybridomas were screened for loss of binding to CD39 mutant 5, a hybridoma was selected that was not among those that showed loss of binding to CD39 mutant 5. This hybridoma (I-394) was among the broader pool possibly due to partial decrease in binding to mutant 5, but did not lose binding to mutant 5 and was therefore not initially retained.

In the context of ongoing screening of supernatants from further immunizations for inhibition of the enzymatic activity of soluble CD39, the antibody I-394 that had been cloned and produced was included as a control. Surprisingly, despite antibody I-394 not being among the clones retained in the epitope-directed screen, this antibody showed strong inhibition of the enzymatic activity of soluble CD39 in the assay described above (Methods).

I-394 was produced with modification to have a human constant regions with an IgG1 Fc domain having the mutations L234A/L235E/G237A/A330S/P331S (Kabat EU numbering) which results in lack of N-linked glycosylation and lack of binding to human Fcγ receptors CD16A, CD16B, CD32A, CD32B and CD64, Briefly, the VH and Vk sequences of the I-394 antibody (the VH and Vk variable regions shown in SEQ ID NOS 6 and 7, respectively) were cloned into expression vectors containing the hulgG1 constant domains harboring the aforementioned mutations and the huCk constant domain respectively. The two obtained vectors were co-transfected into the CHO cell line. The established pool of cell was used to produce the antibody in the CHO medium. The antibody was then purified using protein A. The amino acid sequences of the respective heavy and light chains of I-394 are shown below (Kabat CDRs underlined).

```
I-394 heavy chain variable domain sequence:
                                  (SEQ ID NO: 6)
EVQLQQSGPELVKPGASVKMSCKASGYTFTDYNMHWVKQSHGRTLEWI

GYIVPLNGGSTFNQKFKGRATLTVNTSSRTAYMELRSLTSEDSAAYYCAR

GGTRFAYWGQGTLVTVSA.

I-394 light chain variable domain sequence:
                                  (SEQ ID NO: 7)
DIVLTQSPASLAVSLGQRATISCRASESVDNFGVSFMYWFQQKPGQPPN

LLIYGASNQGSGVPARFRGSGSGTDFSLNIHPMEADDTAMYFCQQTKEVP

YTFGGGTKLEIK.
```

Antibody I-394 was then tested for loss of binding to CD39 mutants defined by substitutions of amino acids exposed at the molecular surface over the surface of CD39. Mutants were transfected in Hek-293T cells, as shown in the table 1, using numbering of SEQ ID NO: 1. Dose-ranges of antibodies I-394 were tested on the 20 mutants by flow cytometry. As shown in FIG. 3B, I-394 showed complete loss of binding to cells expressing mutant 19 of CD39. Mutant 19 includes substitutions at residues R138, M139 and E142. The core epitope of I-394 thus includes one or more (or all of) residues R138, M139 and E142.

Unlike prior antibody BY40 which loses binding to mutant 5 and has the ability to nhibit cellular CD39 but not soluble CD39, antibody I-394 loses binding to the adjacent mutant 19, with strongly reduced binding to mutant 5 (but with some residual binding to mutant 5). Interestingly, the residues of mutant 19 are in close proximity or adjacent to those of residue 5, such that I-394 may represent a shift in epitope compared to BY40. Antibody I-394 thus presents a valuable new epitope for anti-CD39 antibodies that permits inhibition of the ATPase activity of soluble CD39 protein. It also provides a specific positive control that permits the validation and testing of screening assays for detecting further antibodies that neutralize the ATPase activity of soluble CD39 protein.

Example 5: A Non-Epitope Directed Screen for sCD39-Neutralizing mAbs

Based on the results for Example 4 indicating the antibody-mediated inhibition of soluble CD39 is possible, fusions from the different immunizations using different protocols from Example 3 were revisited in order to seek antibodies that neutralize the ATPase activity of sCD39.

Different approaches for screening for ATPase inhibition were then evaluated. In one experiment, I-394 antibody was used to spike supernatants from hybridomas of an immunization of Example 3 that were found negative for ability to inhibit the ATPase activity of soluble CD39. This addition of I-394 to supernatant did not restore the ability of negative supernatants to inhibit ATPase activity of CD39. Antibody I-394 was then purified from the negative supernatant using a Protein A coated beads, and we observed the purified I-394 was again able to inhibit of ATPase activity was restored.

In view of the foregoing results, new immunization and screening protocols were developed in which growing clones from new and past immunizations were screened by flow cytometry using wild type CHO and CHO expressing huCD39 cell lines without assessment of inhibition of soluble CD39 or cellular CD39 ATPase activity, and without screening bias for epitopes. While data regarding loss of binding to mutant 5 or 19 was available for some hybridomas, such data was not used for clone selection but only retained for purposes of rescuing hybridomas for cloning in the event of negative results in the ATPase blocking assay. Hybridomas that bind CD39 were selected and cloned, and then purified using Protein A according to the following protocol:

Add to 300 µl of hybridomas supernatant 10 µl of protein A beads
Add NaCl to be at a final concentration of 1.5M
Rotate the tubes for 3-4 h at 4° C.
Centrifuge 1 min at 1500 rpm
Eliminate the supernatant and perform three washes with 1 ml of TBS
Eliminate all the TBS after the third wash
Add 50 µl of Citrate 0.1M pH3, homogenize and incubate at RT for 5 min
Centrifuge the beads for 1 min at 1500 rpm
Harvest the 50 µl of elution and add rapidly 450 µl of TBS and store at 4° C.

Figure 2A:
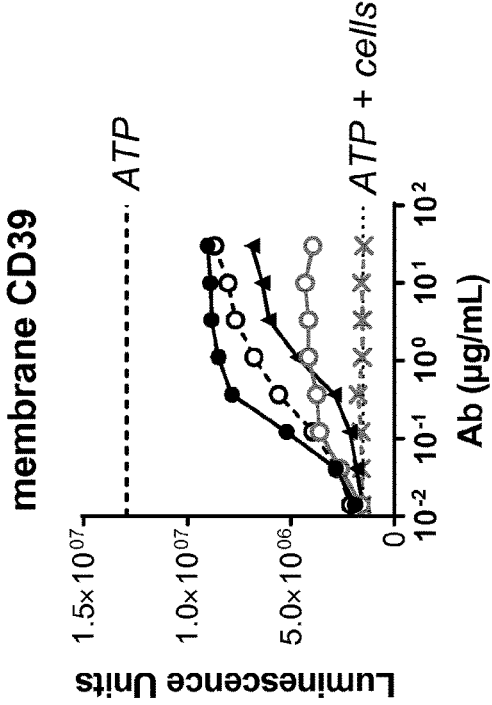
FIG. 2A shows that antibodies BY40, I-394, I-395 and I-396 inhibit cell-membrane bound CD39, with both I-394 and I-395 showing greater potency at all concentrations as well as greater maximal inhibition of cellular CD39 compared to BY40.

The antibodies obtained were then screened in a comparative assay for the ability to inhibit the ATPase activity of CD39 to a similar degree as I-394. Assays used for inhibition of the enzymatic activity of soluble and cellular CD39 were as described above (Methods). Surprisingly, among the exemplary antibodies produced in this way, several showed inhibition of soluble CD39 (as well as inhibition of cellular CD39). FIG. 1 shows a representative screening result, showing antibodies I-397, I-398 and I-399 compared to positive control I-394 antibody. Similarly, antibodies I-395 and I-396 from different immunization inhibited the enzymatic activity of soluble CD39 protein. FIGS. 2A and 2B shows results for antibodies I-395 and I-396 for which greater quantities of antibodies were available for additional experiments for both soluble and cellular CD39 neutralization. FIG. 2A shows that antibodies I-395 and I-396 both inhibit cell-membrane bound CD39 in comparison to BY40 and I-394 antibodies, with both I-394 and I-395 showing greater potency and maximal inhibition of cellular CD39 compared to BY40. FIG. 2B shows that antibodies I-395 and I-396 both inhibit soluble CD39 in comparison to BY40 and I-394 antibodies. While BY40 does not inhibit soluble CD39 at any concentration, I-394, I-395 and I-396 all inhibit soluble CD39 with I-394 showing the greatest potency, followed by I-395 and then I-396 with lower potency.

The results obtained raise the possibility that factor(s) in hybridoma supernatants are rapidly hydrolyzing ATP in both cell culture and in the soluble CD39 assay, such that no signal for ATP is detected in screening of antibodies using conventional methods. The soluble factor may be CD39 or some other enzyme, for example produced by the fusion partner.

Antibodies were then cloned, with modification to have a human constant regions with an IgG1 Fc domain having the mutations L234A/L235E/G237A/A330S/P331S (Kabat EU numbering) which results in lack of N-linked glycosylation and lack of binding to human Fcγ receptors CD16A, CD16B, CD32A, CD32B and CD64, in the same way as shown herein for I-394. The resulting antibodies can then be subjected to titrations and then more detailed activity assessment as shown in Example 7-9 (titration, inhibition of ATPase activity) to assess $EC_{50}$ and $10_{50}$ determinations to rank antibodies according to potency.

Example 6: Epitope Mapping of sCD39 Neutralizing mAbs

As shown in Example 4, I-394 showed complete loss of binding to cells expressing mutant 19 of CD39, but did not lose binding to mutant 5. In order to define the epitopes of the further anti-CD39 antibodies of Example 5, they were tested for loss of binding to the panel of CD39 mutants as described in Example 1 and Table 1. Mutants were transfected in Hek-293T cells, as shown in the table 1, using numbering of SEQ ID NO: 1.Dose-ranges of test antibodies (10-2.5-0.625-0.1563-0.0391-0.0098-0.0024-0.0006 µg/ml) are tested on the 20 generated mutants by flow cytometry.

Results showed that the antibodies selected in Example 5 for ability to inhibit soluble CD39 represented several different epitopes. Among the antibodies that showed inhibition of soluble extracellular CD39 in Example 5, antibody I-395 is an example of an antibody that displayed loss of binding to mutant 5 having substitutions at residues Q96, N99, E143 and R147, and also loss of binding to mutant 19 having substitutions at residues R138, M139 and E142.

Mutant 19 includes substitutions at residues R138, M139 and E142. The core epitope on CD39 of I-395 thus comprises one, two, three or four of residues Q96, N99, E143 and R147 as well as one, two or three of residues R138, M139 and E142.

Antibody I-398 on the other hand, is an example of an antibody that displayed loss of binding to mutant 19 having substitutions at residues R138, M139 and E142, but does not have decreased or loss of binding to mutant 5 having substitutions at residues Q96, N99, E143 and R147.

Other antibodies that showed inhibition of soluble extracellular CD39 in Example 5 had very different epitopes and did not show loss of binding to either of mutants 5 or 19, suggesting that soluble CD39 can also be inhibited by binding to other sites on sCD39. For some antibodies, loss of binding to one of the 20 mutants of Table 1 permitted the localization of binding site on CD39, while for others the binding site remained to be determined as they did not lose binding to any of the 20 mutants. Among the antibodies showing inhibition of ATPase activity of soluble CD39 in Example 5, antibody I-396 showed loss of binding to mutant 15 having substitutions K87A, E100A and D107A, without loss of binding to any of the other 20 mutants. The core epitope on CD39 of this antibody thus comprises one or more (or all of) residues K87, E100 and D107. Antibody I-399 showed loss of binding to mutant 11 having substitutions N371K, L372K, E375A, K376G, V377A and an insertion of a valine between K376 and V377 (referred to in Table 1 as "insertion 377V"), without loss of binding to any of the other 20 mutants. The core epitope on CD39 of this antibody thus comprises one or more (or all of) residues N371, L372, E375, K376 and V377. FIG. 3A shows the position of residues mutated in mutants 5 (M5), 15 (M15) and 19 (M19) on the surface of the CD39 protein. FIG. 3B shows results of binding to mutants 5, 15 and 19 for different antibodies.

The results thus show that antibodies that inhibit soluble CD39 can be obtained against different epitopes. The epitopes include epitopes defined by one or more residues of mutant 19 which are located adjacent to the binding site of the BY40 or BY40-like antibodies that inhibit only cellular CD39 but not soluble CD39 (which lose binding to mutant 5), epitopes that are defined by one or more residues of mutant 19 but also partly by mutant 5, indicating possibly a smaller shift compared to BY40 or BY40-like antibodies, epitopes defined by one or more residues of mutant 19 and not by residues of mutant 5, as well as other epitopes such as those defined by one or more residues of mutant 11 or one or more residues of mutant 15, or further by other antibodies that do not have any reduced binding to any of mutants 5, 15 or 19 for which localization of epitopes remain to be determined.

Example 7: Antibody Titration on CD39 Expressing Cells by Flow Cytometry

Antibody I-394 was tested in two repeated experiments for binding to CHO cells expressing human CD39, CHO cells expressing cynomolgus (*Macaca fascicularis*) CD39, CHO cells expressing murine CD39, and human Ramos lymphoma cells (ATCC™, reference CRL-1596). Cells were incubated with various concentration of unlabeled anti-CD39 antibody from 30 µg/ml to $5 \times 10^{-4}$ µg/ml, for 30 minutes at 4° C. After washes, cells were incubated with Goat anti-mouse H+L labeled secondary antibody for 30 min at 4° C.

Results are shown in FIGS. 4A-D. Antibody I-394 bound to cells expressing human CD39 (CHO-huCD39), cells expressing cynomolgus CD39 (CHO-cyCD39) and to Ramos lymphoma cells, but not to cells expressing murine CD39 (CHO-moCD39). I-394 bound to Ramos cells with $EC_{50}$ values of 0.16 µg/ml and 0.19 µg/ml in the respective first and second set of experiments. Several other anti-CD39 antibodies showed comparable $EC_{50}$ values for binding to Ramos cells.

Example 8: IC50 Determination for Inhibition of Cellular ATPase Activity

The inhibition by antibody I-394 of the ATPase activity of CD39 in CD39-expressing cells was evaluated using the assay used for inhibition of the enzymatic activity of cellular CD39 as described above (Methods).

Results are shown in FIGS. 5A-D. I-394 is highly potent at blocking CD39 enzymatic activity in tumor (Ramos) cells, with greater potency compared to all other antibodies tested. I-394 also blocks CD39 enzymatic activity in cells expressing human CD39 (CHO-huCD39), and in cells expressing cynomolgus CD39 (CHO-cyCD39). Cells expressing murine CD39 (CHO-moCD39) are shown as a negative control. The calculated $IC_{50}$ (inhibition of 50% of the enzymatic activity of CD39 expressed by 50,000 Ramos cells) is 0.05 µg/ml. The maximum inhibition achieved is 81.6%. Isotype control had no effect.

Figure 6:
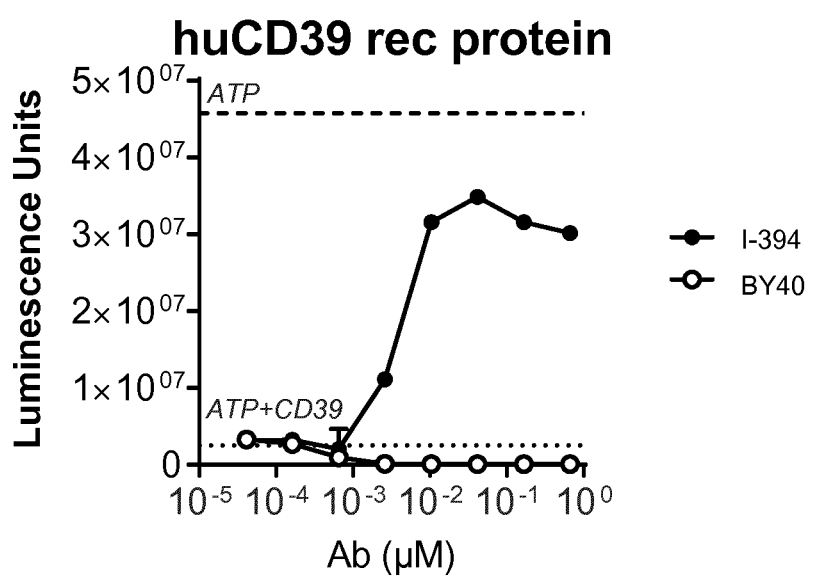
FIG. 6 shows antibody I-394 is highly potent at blocking the enzymatic activity of soluble recombinant human CD39 protein, as assessed by quantifying luminescence units which are proportional to the amount of ATP present.

Example 9: IC50 Determination for Inhibition of the ATPase Activity of Recombinant Soluble CD39 Protein The inhibition by antibody I-394 of the ATPase activity of soluble CD39 protein was evaluated using the assays used for inhibition of the enzymatic activity of soluble CD39 as described above (Methods). Results are shown in FIG. 6. I-394 inhibits the enzymatic activity of soluble CD39 protein. Antibody BY40 in comparison did not inhibit the enzymatic activity of soluble CD39 protein. The calculated $IC_{50}$ is 0.003 µg/ml. The maximum inhibition achieved is 74.9%.

Example 10: ELISA Titration on CD39-L1, L2, L3, L4 Isoforms

Antibody I-394 was tested for binding to recombinant human CD39 isoforms (Rec-huCD39 isoforms) having amino acid sequences shown below were coated in 96-well plate in PBS 1× at 500 ng/ml or 1 µg/ml at 4° C. overnight. Wells were washed in TBS Tween 20, and further saturated 2H at RT in TBS Blocking buffer. Dose range concentration of primary antibody was incubated in TBS blocking buffer for 2 h at RT. Wells were washed in TBS Tween 20. Secondary Antibody (GAM-HRP or GAH-HRP in TBS blocking buffer) was incubated for 1H at RT, and was revealed with TMB. Optical density was measured on Enspire™ at OD=450.

Amino Acid Sequence of the Cloned huCD39 (Vascular Isoform):

```
Human CD39-L1, also known as NTPDase2 or ENTPD2:
                                                                 (SEQ ID NO: 2)
  1 MAGKVRSLLP PLLLAAAGLA GLLLLCVPTR DVREPPALKY GIVLDAGSSH TSMFIYKWPA

61 DKENDTGIVG QHSSCDVPGG GISSYADNPS GASQSLVGCL EQALQDVPKE RHAGTPLYLG
```

-continued

```
121 ATAGMRLLNL TNPEASTSVL MAVTHTLTQY PFDFRGARIL SGQEEGVFGW VTANYLLENF

181 IKYGWVGRWF RPRKGTLGAM DLGGASTQIT FETTSPAEDR ASEVQLHLYG QHYRVYTHSF

241 LCYGRDQVLQ RLLASALQTH GFHPCWPRGF STQVLLGDVY QSPCTMAQRP QNFNSSARVS

301 LSGSSDPHLC RDLVSGLFSF SSCPFSRCSF NGVFQPPVAG NFVAFSAFFY TVDFLRTSMG

361 LPVATLQQLE AAAVNVCNQT WAQQLLSRGY GFDERAFGGV IFQKKAADTA VGWALGYMLN

421 LTNLIPADPP GLRKGTDFSS WVVLLLLFAS ALLAALVLLL RQVHSAKLPS TI.
```

Human CD39-L2, also known as NTPDase6 or ENTPD6:
(SEQ ID NO: 3)

```
  1 MKKGIRYETS RKTSYIFQQP QHGPWQTRMR KISNHGSLRV AKVAYPLGLC VGVFIYVAYI

61 KWHRATATQA FFSITRAAPG ARWGQQAHSP LGTAADGHEV FYGIMFDAGS TGTRVHVFQF

121 TRPPRETPTL THETFKALKP GLSAYADDVE KSAQGIRELL DVAKQDIPFD FWKATPLVLK

181 ATAGLRLLPG EKAQKLLQKV KEVFKASPFL VGDDCVSIMN GTDEGVSAWI TINFLTGSLK

241 TPGGSSVGML DLGGGSTQIA FLPRVEGTLQ ASPPGYLTAL RMFNRTYKLY SYSYLGLGLM

301 SARLAILGGV EGQPAKDGKE LVSPCLSPSF KGEWEHAEVT YRVSGQKAAA SLHELCAARV

361 SEVLQNRVHR TEEVKHVDFY AFSYYYDLAA GVGLIDAEKG GSLVVGDFEI AAKYVCRTLE

421 TQPQSSPFSC MDLTYVSLLL QEFGFPRSKV LKLTRKIDNV ETSWALGAIF HYIDSLNRQK

481 SPAS.
```

Human CD39-L3, also known as NTPDase3 or ENTPD3:
(SEQ ID NO: 4)

```
  1 MFTVLTRQPC EQAGLKALYR TPTIIALVVL LVSIVVLVSI TVIQIHKQEV LPPGLKYGIV

61 LDAGSSRTTV YVYQWPAEKE NNTGVVSQTF KCSVKGSGIS SYGNNPQDVP RAFEECMQKV

121 KGQVPSHLHG STPIHLGATA GMRLLRLQNE TAANEVLESI QSYFKSQPFD FRGAQIISGQ

181 EEGVYGWITA NYLMGNFLEK NLWHMWVHPH GVETTGALDL GGASTQISFV AGEKMDLNTS

241 DIMQVSLYGY VYTLYTHSFQ CYGRNEAEKK FLAMLLQNSP TKNHLTNPCY PRDYSISFTM

301 GHVFDSLCTV DQRPESYNPN DVITFEGTGD PSLCKEKVAS IFDFKACHDQ ETCSFDGVYQ

361 PKIKGPFVAF AGFYYTASAL NLSGSFSLDT FNSSTWNFCS QNWSQLPLLL PKFDEVYARS

421 YCFSANYIYH LFVNGYKFTE ETWPQIHFEK EVGNSSIAWS LGYMLSLTNQ IPAESPLIRL

481 PIEPPVFVGT LAFFTAAALL CLAFLAYLCS ATRRKRHSEH AFDHAVDSD.
```

Human CD39-L4, also known as NTPDase5 or ENTPD5:
(SEQ ID NO: 5)

```
  1 MATSWGTVFF MLVVSCVCSA VSHRNQQTWF EGIFLSSMCP INVSASTLYG IMFDAGSTGT

61 RIHVYTFVQK MPGQLPILEG EVFDSVKPGL SAFVDQPKQG AETVQGLLEV AKDSIPRSHW

121 KKTPVVLKAT AGLRLLPEHK AKALLFEVKE IFRKSPFLVP KGSVSIMDGS DEGILAWVTV

181 NFLTGQLHGH RQETVGTLDL GGASTQITFL PQFEKTLEQT PRGYLTSFEM FNSTYKLYTH

241 SYLGFGLKAA RLATLGALET EGTDGHTFRS ACLPRWLEAE WIFGGVKYQY GGNQEGEVGF

301 EPCYAEVLRV VRGKLHQPEE VQRGSFYAFS YYYDRAVDTD MIDYEKGGIL KVEDFERKAR

361 EVCDNLENFT SGSPPFLCMDL SYITALLKDG FGFADSTVLQ LTKKVNNIET GWALGATFHL

421 LQSLGISH.
```

I-394 bound to the CD39 but not to any of the isoforms CD39-L 1, -L2, -L3 or -L4. Isotype control antibodies (IC) did not bind to any CD39 or CD39-L molecule. Results are shown in FIGS. 7A-E.

Example 11: Activation of Dendritic Cells

While ATP has pro-inflammatory, CD39-mediated catabolism of ATP is believed to be able to impair dendritic cell (DC) activation, in turn altering a broader adaptive immune response against tumor antigen. In order to evaluate whether CD39 blockade using anti-CD39 antibodies could overcome CD39-mediated alteration of dendritic cell (DC) activation in the presence of ATP, we incubated monocyte-derived DC (moDC) with anti-CD39 antibodies in the presence of ATP.

Figure 8:
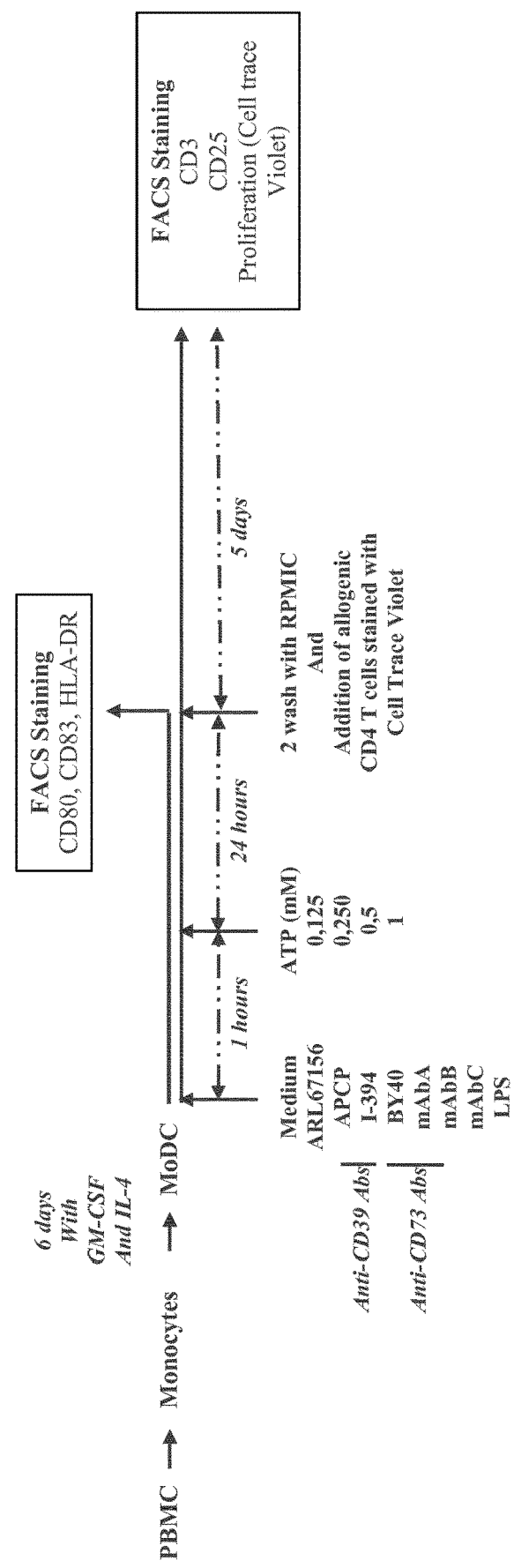
FIG. 8 shows the experimental procedure for assessing the effect of ATP-mediated DC activation on CD4 T cells activation, ATP-activated DC were washed and then incubated with allogenic CD4 T cells (ratio 1 MoDC/4 T cells) for a mixed lymphocytes reaction (MLR) during 5 days. T cells activation and proliferation were analyzed through CD25 expression and Cell Trace Violet dilution by flow cytometry.
Figure 9A:
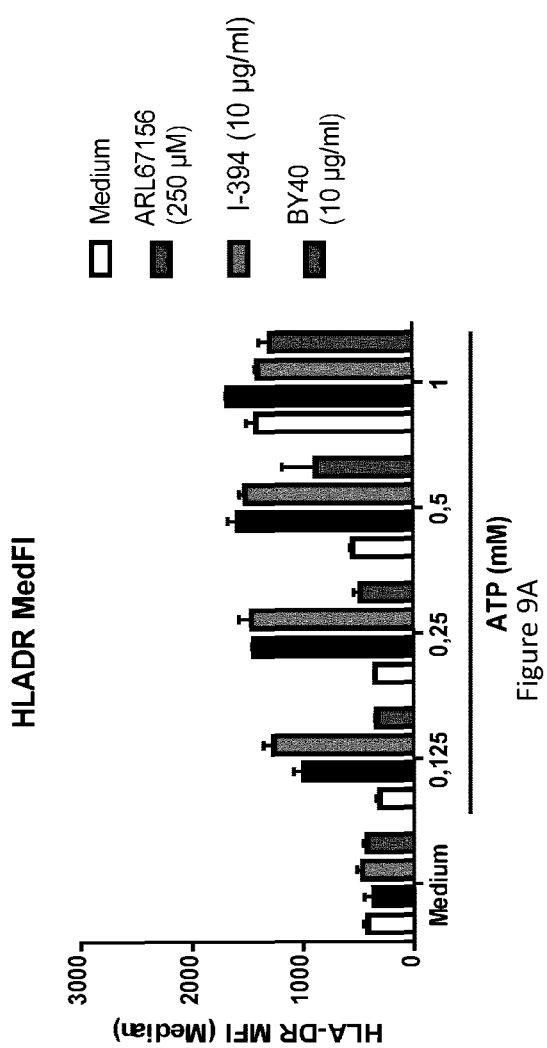
Figure 9B:
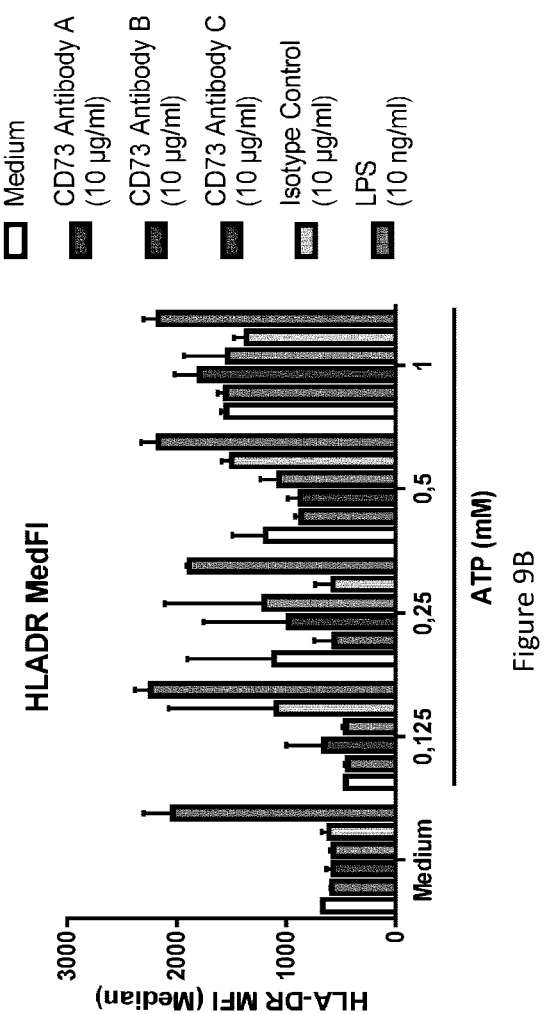
Figure 11A:
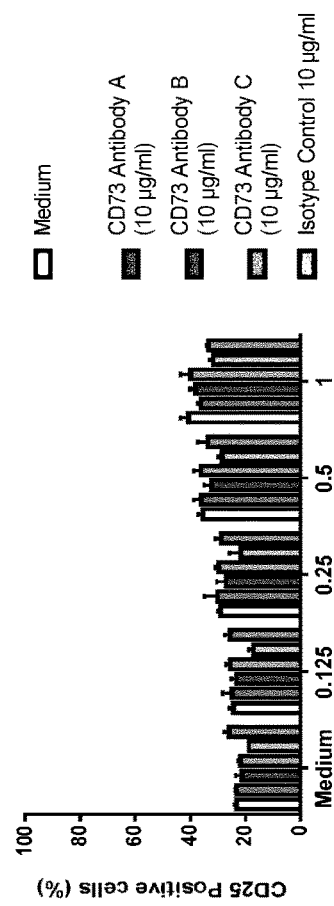
FIGS. 11A-D showing CD25 expression show that MoDC activated in presence of ATP were able to induce T cells activation and proliferation in a MLR assay; the enhancement of ATP-mediated MoDC activation by anti-CD39 blocking antibody I-394 resulted in higher T cells proliferation and activation. The legends, top to bottom, correspond to the bars in the graph, from left to right.
Figure 11B:
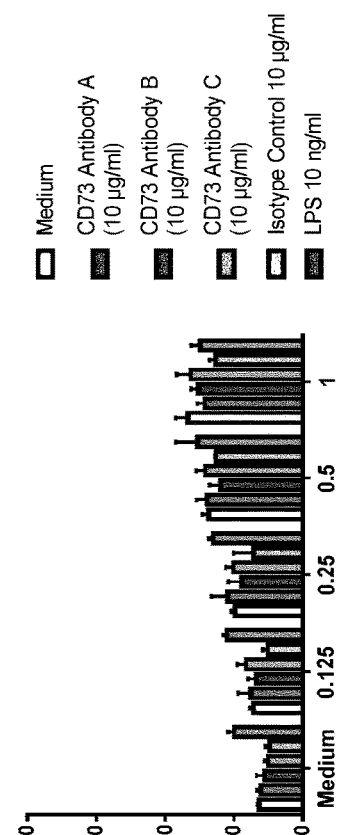
Figure 11C:
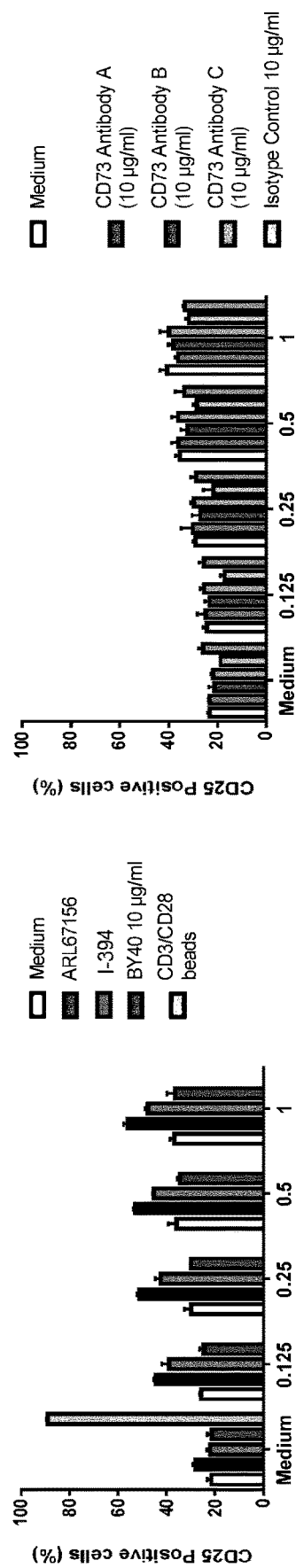
Figure 11D:
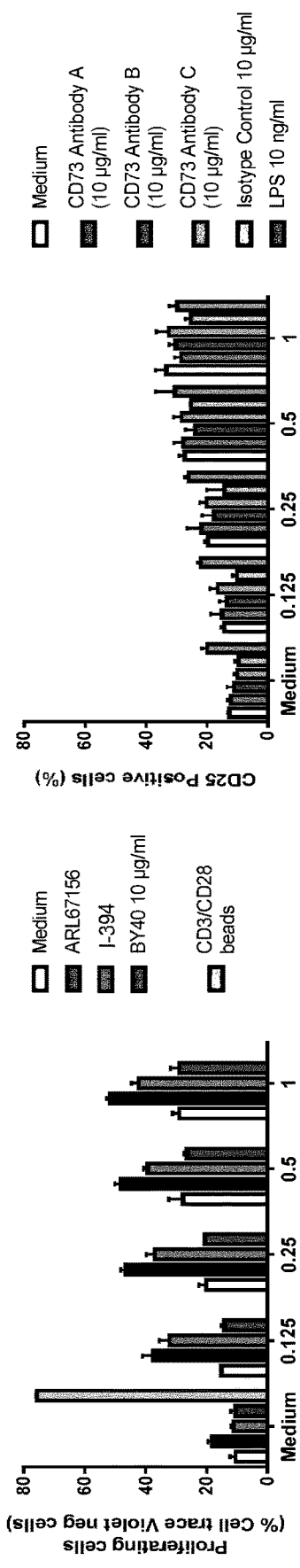

Briefly, human monocytes were purified from human healthy blood and differentiated into MoDC in presence of GM-CSF and IL-4 during 6 days. Then MoDC were activated in presence of ATP (Sigma, 0.25-1 mM) during 24 hours and DC activation were assessed by analyzing CD80, CD83 and HLA-DR expression by flow cytometry. In some cases, MoDC were preincubated during 1 hours in presence of CD39 inhibitor: ARL6716 (Tocris, 250 µM), CD73 inhibitor: APCP (Tocris 50 µM), anti-CD39 blocking antibody I-394 or BY40 (for BY40 see WO2009/095478), or anti-CD73 blocking antibodies. LPS (Invivogen, 10 ng/ml) was used as positive control. To assess resulting effect of ATP-mediated DC activation on CD4 T cells activation, ATP-activated DC were washed and then incubated with allogenic CD4 T cells (ratio 1 MoDC/4 T cells) for a mixed lymphocytes reaction (MLR) during 5 days. T cells activation and proliferation were analyzed through CD25 expression and Cell Trace Violet dilution by flow cytometry (FIG. 8).

Results are shown in FIGS. 9A and 9B, 10A-D and 11A-D. In the presence of negative control (medium), moDC activation was observed in the presence of 1 mM ATP, however ATP at 0.125 mM, 0.25 mM or 0.5 mM did not permit moDC activation. Addition of chemical inhibitors of CD39 which are believed to fully block CD39 enzymatic activity by binding to the active site lead to moDC activation at each of 0.125 mM, 0.25 mM or 0.5 mM. However, antiCD39 antibodies such as BY 40 or anti-CD73 antibodies were not able to favor ATP-induced activation of dendritic cell (DC), suggesting that antibodies are not able to block enzymatic activity sufficiently to avoid ATP catabolism. Surprisingly, the anti-CD39 blocking antibody I-394 (shown in Figures at concentration 10 µg/ml) which substantially fully blocks the ATPase activity of CD39 and can therefore permit accumulation of ATP, permitted moDC activation as assessed by HLA-DR or CD83 expression at each of 0.125 mM, 0.25 mM or 0.5 mM (FIGS. 9A and 9B and 10A-D). Interestingly, the MoDC activated in presence of ATP were able to induce better T cells activation and proliferation in a MLR assay. Moreover, the enhancement of ATP-mediated MoDC activation by anti-CD39 blocking antibody I-394 resulted in higher T cells proliferation and activation (FIGS. 11A-D).

Assessment of the ability to CD39 inhibitors to activate DC in the presence of ATP provides a method to identify and evaluate anti-CD39 antibodies that are able to achieve a high degree of inhibition of CD39.

The possibility of using anti-CD39 antibodies to relieve the immunosuppressive effect exerted by CD39 upon DC can provide for enhancement of the adaptive immune response toward antigens, notably on tumors cells. Furthermore, such anti-CD39 antibodies may be of particular interest when used to enhance the immunogenic effect of chemotherapeutic agents. Numerous chemotherapeutic agents that cause necrosis of tumor cells are able to induce ATP; combined use with anti-CD39 antibodies can be particularly useful to enhance the anti-tumor response in these settings.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar references are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment herein using terms such as "comprising", "having," "including," or "containing" with reference to an element or elements is intended to provide support for a similar aspect or embodiment herein that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. An antibody or antibody fragment that binds and inhibits the ATPase activity of a soluble extracellular domain human CD39 (NTPDase1) protein, wherein the antibody or antibody fragment comprises:
   (a) a HCDR1 comprising the amino acid sequence DYNMH (SEQ ID NO: 8); a HCDR2 comprising the amino acid sequence YIVPLNGGSTFNQKFKG (SEQ ID NO: 9); a HCDR3 comprising the amino acid sequence GGTRFAY (SEQ ID NO: 10; a LCDR1 comprising the amino acid sequence RASESVDNFGVSFMY (SEQ ID NO: 11); a LCDR2 region comprising the amino acid sequence GASNQGS (SEQ ID NO: 12); and a LCDR3 region comprising the amino acid sequence QQTKEVPYT (SEQ ID NO: 13);
   (b) a HCDR1 comprising the amino acid sequence DYNMH (SEQ ID NO: 16); a HCDR2 comprising the amino acid sequence YINPNNGGTTYNQKFKG (SEQ ID NO: 17); a HCDR3 comprising the amino acid sequence GGTRFAS (SEQ ID NO: 18; a LCDR1 comprising the amino acid sequence RASESVDNYGISFMY (SEQ ID NO: 19); a LCDR2 region comprising the amino acid sequence AASTQGS (SEQ ID NO: 20); and a LCDR3 region comprising the amino acid sequence QQSKEVPFT (SEQ ID NO: 21);
   (c) a HCDR1 comprising the amino acid sequence DTYIN (SEQ ID NO: 24); a HCDR2 comprising the amino acid sequence RIDPANGNTKYDPKFQG (SEQ ID NO: 25); a HCDR3 comprising the amino acid sequence WGYDDEEADYFDS (SEQ ID NO: 26); a LCDR1 comprising the amino acid sequence RASESVDNYGISFMN (SEQ ID NO: 27); a LCDR2 region comprising the amino acid sequence AASNQGS (SEQ ID NO: 28); and a LCDR3 region comprising the amino acid sequence HQSKEVPWT (SEQ ID NO: 29); or
   (d) a HCDR1 comprising the amino acid sequence SFWMN (SEQ ID NO: 32); a HCDR2 comprising the amino acid sequence EIDPSDFYTNSNQRFKG (SEQ ID NO: 33); a HCDR3 comprising the amino acid sequence GDFGWYFDV (SEQ ID NO: 34); a LCDR1 comprising the amino acid sequence SASSSINSNYLH (SEQ ID NO: 35); a LCDR2 region comprising the amino acid sequence RTSNLAS (SEQ ID NO: 36); and a LCDR3 region comprising the amino acid sequence QQGSSLPRT (SEQ ID NO: 37).

2. The antibody or antibody fragment of claim 1, wherein the antibody or antibody fragment inhibits the ATPase activity of the CD39 protein in the presence of exogenously added ATP at a concentration of 20 µM.

3. The antibody or antibody fragment of claim 1, wherein the antibody or antibody fragment is capable of binding human CD39 protein at the surface of a cell and that is capable of inhibiting the ATPase activity of said CD39 protein at the surface of a cell.

4. The antibody or antibody fragment of claim 1, wherein the soluble extracellular domain CD39 is a CD39 protein lacking the transmembrane domains near the N- and C-terminal ends found in membrane bound CD39.

5. The antibody or antibody fragment of claim 1, wherein the antibody comprises an Fc domain comprising an amino acid modification compared to a wild-type Fc domain, and that has reduced or abolished binding to one or more, or all of, the human Fcγ receptors CD16A, CD16B, CD32A, CD32B and/or CD64.

6. A pharmaceutical composition comprising an antibody or antibody fragment according to claim 1, and a pharmaceutically acceptable carrier.

7. A nucleic acid encoding a heavy and/or light chain of an antibody or antibody fragment of claim 1.

8. A recombinant host cell producing the antibody or antibody fragment of claim 1.

9. A method for the treatment of a tumor or cancer in an individual in need thereof, the method comprising administering to the individual an effective amount of an antibody or antibody fragment of claim 1.

10. The method of claim 9, wherein the method comprises administering to said individual an effective amount of an antibody or antibody fragment of claim 1, in combination with an antibody that neutralizes the inhibitory activity of human PD-1.

11. The method of claim 9, wherein the tumor or cancer is a leukemia, bladder cancer, glioma, glioblastoma, ovarian cancer, melanoma, prostate cancer, thyroid cancer, esophageal cancer or a breast cancer.

12. A method for reducing the ATPase activity of soluble CD39 protein in an individual, the method comprising administering to said individual an effective amount of an antibody or antibody fragment of claim 1.

* * * * *